US008778671B2

(12) United States Patent
Pletnev et al.

(10) Patent No.: US 8,778,671 B2
(45) Date of Patent: Jul. 15, 2014

(54) CONSTRUCTION OF WEST NILE VIRUS AND DENGUE VIRUS CHIMERAS FOR USE IN A LIVE VIRUS VACCINE TO PREVENT DISEASE CAUSED BY WEST NILE VIRUS

(75) Inventors: Alexander G. Pletnev, Rockville, MD (US); Joseph R. Putnak, Silver Spring, MD (US); Robert M. Chanock, Bethesda, MD (US); Brian R. Murphy, Bethesda, MD (US); Stephen S. Whitehead, Montgomery Village, MD (US); Joseph E. Blaney, Jr., Frederick, MD (US)

(73) Assignees: The United States of America, as represented by the Secretary of the Department of Health & Human Services, Washington, DC (US); The Walter Reed Army Institute of Research, Silver Spring, MD (US)

( * ) Notice: Subject to any disclaimer, the term of this patent is extended or adjusted under 35 U.S.C. 154(b) by 909 days.

(21) Appl. No.: 10/871,775

(22) Filed: Jun. 18, 2004

(65) Prior Publication Data
US 2005/0100886 A1    May 12, 2005

Related U.S. Application Data

(63) Continuation of application No. PCT/US03/00594, filed on Jan. 9, 2003.

(60) Provisional application No. 60/347,281, filed on Jan. 10, 2002.

(51) Int. Cl.
*C07H 21/04*     (2006.01)
*A61K 39/00*     (2006.01)

(52) U.S. Cl.
USPC .... 435/320.1; 435/325; 435/69.3; 536/23.72; 424/218.1

(58) Field of Classification Search
None
See application file for complete search history.

(56) References Cited

U.S. PATENT DOCUMENTS 7,094,411 B2 * 8/2006 Kinney et al. ............ 424/218.1

FOREIGN PATENT DOCUMENTS

| WO | WO 93/06214 | 4/1993 |
| WO | WO 00/57910 | 10/2000 |
| WO | WO 01/60847 | 8/2001 |

OTHER PUBLICATIONS

Davis et al. Journal of Virology, 2001, vol. 75, p. 4040-4047.*
Dauphin et al. Vaccine, 2007, vol. 25; p. 5563-5576.*
Men et al. Journal of Virology, 1996, vol. 70, p. 3930-3937.*
Anderson, J.F. et al. 1999 "Isolation of west nile virus from mosquitoes, crows, and a cooper's hawk in connecticut" *Science* 286:2331-2333.
Blaney, Jr. J.E. et al. 2001 "Chemical mutagenesis of dengue virus type 4 yields mutant viruses which are temperature sensitive in veno cells or human liver cells and attenuated in mice" *J. Virol.* 75:9731-9740.
Bray, M. et al. 1991 "Construction of intertypic chimeric dengue viruses by substitution of structural protein genes" *PNAS USA* 88:10342-10346.
Bray, M. et al. 1996 "Monkeys immunized with intertypic chimeric dengue viruses are protected against wild-type virus challenge" *J. Virol.* 70:4162-4166.
Calisher, C.H. et al. 1989 "Antigenic relationships between flaviviruses as determined by cross-neutralization tests with polyclonal antisera" *J. Gen. Virol.* 70:37-43.
Caufour, P.S. et al. 2001 "Construction, characterization and immunogenicity of recombinant yellow fever 17D-dengue yype 2 viruses" *Virus Res.* 79:1-14.
Chambers, T.J. et al. 1999 "Yellow fever/japanese encephalitis chimeric viruses: construction and biological properties" *J. Virol.* 73:3095-3101.
Davis, B.S. et al. 2001 "West nile virus recombinant DNA vaccine protects mouse and horse from virus challenge and expresses in vitro a noninfectious recombinant antigen that can be used in enzyme-linked immunosorbent assays" *J. Virol.* 75:4040-4047.
Durbin, A.P. et al. 2001 "Attenuation and immunogenicity in humans of a live dengue virus type-4 vaccine candidate with a 30 nucleotide deletion in its 3'-untranslated region" *Am. J. Trop. Med. Hyg.* 65:405-413.
Guirakhoo, F. et al. 2000 "Recombinant chimeric yellow fever-dengue type 2 virus is mmunogenic and protective in nonhuman primates" *J. Virol.* 74:5477-5485.
Halevy, M. et al. 1994 "Loss of active neuroinvasiveness in attenuated strains of west nile virus: pathogenicity in immunocompetent and SCID mice" *Arch. Virol.* 137:355-370.
Huang, C.Y. et al. 2000 "Chimeric dengue type 2 (vaccine strain PDK-53)/dengue type 1 virus as a potential candidate dengue type 1 virus vaccine" *J. Virol.* 74:3020-3028.
Lanciotti, R.S. et al. 1999 "Origin of the west nile virus responsible for an outbreak of encephalitis in the northeastern united states" *Science* 286:2333-2337.
Lee, E. et al. 2000 "Mutagenesis of the signal sequence of yellow fever virus prM protein: enhancement of signalase cleavage in vitro is lethal for virus production" *J. Virol.* 74:24-32.
Pletnev, A.G. et al. 1992 "Construction and characterization of chimeric tick-borne encephalitis/ dengue type 4 viruses" *PNAS USA* 89:10532-10536.
Pletnev, A.G. et al. 1993 "Chimeric tick-borne encephalitis and dengue type 4 viruses: effects of mutations on neurovirulence in mice" *J. Virol.* 67:4956-4963.
Pletnev, A.G. et al. 1998 "Attenuation of the langat tick-borne flavivirus by chimerization with mosquito-borne flavivirus dengue type 4" *PNAS USA* 95:1746-1751.
Pletnev, A.G. et al. 2000 "Chimeric langat/dengue viruses protect mice from heterologous challenge with the highly virulent strains of tick-borne encephalitis virus" *Virology* 274:26-31.

(Continued)

*Primary Examiner* — Agnieszka Boesen
(74) *Attorney, Agent, or Firm* — Edwards Wildman Palmer LLP; Peter F. Corless; Richard B. Emmons

(57) ABSTRACT

The present invention relates to attenuated, immunogenic West Nile virus chimeras built on a dengue virus backbone for the production of immunogenic, live, attenuated West Nile virus vaccines.

6 Claims, 6 Drawing Sheets

(56) References Cited

OTHER PUBLICATIONS

Pletnev, A.G. 2001 "Infectious cDNA clone of attenuated langat tick-borne flavivirus (strain E5) and a 3' deletion mutant constructed from it exhibit decreased neuroinvasiveness in immunodeficient mice" *Virology* 282:288-300.

Pletnev, A.G. et al. 2001 "Tick-borne langat/mosquito-borne dengue flavivirus chimera, a candidate live attenuated vaccine for protection against disease caused by members of the tick-borne encephalitis virus complex: evaluation in rhesus monkeys and in mosquitoes" *J. Virol.* 75:8259-8267.

Pletnev, A.G. et al. 2002 "West nile virus/dengue type 4 virus chimeras that are reduced in neurovirulence and peripheral virulence without loss of immunogenicity or protective efficacy" *PNAS USA* 99:3036-3041.

Stocks, C.E. et al. 1998 "Signal peptidase cleavage at the flavivirus C-prM junction: dependence on the viral NS2B-3 protease for efficient processing requires determinants in C, the signal peptide, and prM" *J. Virol.* 72:2141-2149.

Van Der Most, R.G. et al. 2000 "Chimeric yellow fever/dengue virus as a candidate dengue vaccine: quantitation of the dengue virus-specific CD8 T-cell response" *J. Virol.* 74:8094-8101.

Wang, T. et al. 2001 "Immunization of mice against west nile virus with recombinant envelope protein" *J. Immunol.* 167:5273-5277.

Fu, Jianlin, et al. 1992 "Full-Length cDNA Sequence of Dengue Type 1 Virus (Singapore Strain S275/90)", Virology 188, pp. 953-958.

Men, Ruhe, et al. 1996 "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys", Journal of Virology, pp. 3930-3937.

Monath, T.P. et al., "West Nile Virus Vaccine", Current Drug Targets, Bentham Science Publisher, vol. 1, No. 1, 2001, pp. 37-50.

Monath, T. P., "Prospects for Development of a Vaccine against the West Nile Virus", Annals of the N.Y. Academy of Sciences, N.Y. Academy of Sciences, N.Y., 2001, pp. 1-12.

Pletnev, A. G. et al., "Chimeric West Nile/dengue virus vaccine candidate: Preclinical evaluation in mice, geese and monkeys for safety and immunogenicity", Vaccine, vol. 24, No. 40-41, 2006, pp. 6392-6404.

Pletnev, A. G. et al., "Molecularly engineered live-attenuated chimeric West Nile/dengue virus vaccines protect rhesus monkeys from West Nile virus", Virology, vol. 314, No. 1, 2003, pp. 190-195.

F. Guirakhoo et al., "Construction, Safety, and Immunogenicity in Nonhuman Primates of a Chimeric Yellow Fever-Dengue Virus Tetravalent Vaccine", Journal of Virology, 75(16), pp. 7290-7304 (2001).

* cited by examiner

Positive-sense RNA virus:

| Structural | Non-structural protein genes |
|---|---|
| 5' C | prM | E | NS1 | 2A | 2B | NS3 | 4A | 4B | NS5 | 3' |

DEN4

WN

New WN/DEN4 Chimeric Flavivirus:

prM  E

- Infectious RNA transcribed in vitro from cDNA clones
- Infectious RNA transfected into cell culture (C6/36, Vero)
- Progeny virus recovered and evaluated in susceptible animals

*FIG. 1B*

```
                          C          preM              E                   NS1
              5'  -----DEN4----|----------------WN insert----------------|---DEN4---  3'
                              1st                                       2nd
                           junction                                   junction
                           C/preM                                        E No. clones tested/
                                                                                         No. viable virus
                                                                              WN cDNA    recovered K   G   G   R   T   G   I   A                  I   N   A   R   D
WN      AAG AGA GGA AGA ACC GGA ATT GCA  ........  ATC AAT GCT CGT GAT       403-2400    NA**

R   S   T   I   T   L   L   C                  L   N   S   R   N
DEN4    AGG TCA ACG ATA ACA TTG CTG TGC  ........  CTG AAC TCG AGG AAC                   NA

WN/DEN4:
         R   S   A   V*  T   G   I   A                  I   N   S   R   N
group 1 AGG TCT GCA GTG ACC GGA ATT GCA  ........  ATC AAC TCG AGG AAC      419-2390    7/0
                PstI                                        XhoI R   S   A   G*  T   G   I   A                  I   N   S   R   N
group 2 AGG TCT GCA GGG ACC GGA ATT GCA  ........  ATC AAC TCG AGG AAC      419-2390    6/0

R   S   A   D*  T   G   I   A                  I   N   S   R   N
group 3 AGG TCT GCA GAC ACC GGA ATT GCA  ........  ATC AAC TCG AGG AAC      420-2390    3/0

R   S   A   D*  T   G   T   A                  I   N   S   R   N
group 4 AGG TCT GCA GAC ACC GGA ACT GCA  ........  ATC AAC TCG AGG AAC      420-2390    2/2+
```

FIG. 2

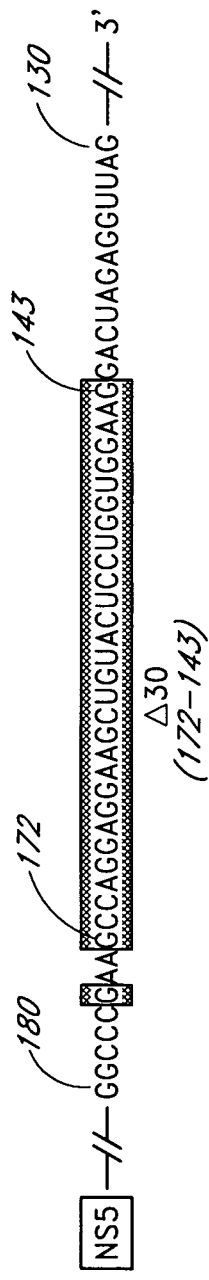

FIG. 4C

SEQUENCE LISTING

<160> NUMBER OF SEQ ID NOS: 37

<210> SEQ ID NO 1
<211> LENGTH: 10
<212> TYPE: PRT
<213> ORGANISM: West Nile virus

<400> SEQUENCE: 1

Lys Lys Arg Gly Gly Arg Thr Gly Ile Ala
1               5                   10

```
<210> SEQ ID NO 2
<211> LENGTH: 30
<212> TYPE: DNA
<213> ORGANISM: West Nile Virus

<400> SEQUENCE: 2
aagaaaagag gaggaaagac cggaattgca                                    30

<210> SEQ ID NO 3
<211> LENGTH: 10
<212> TYPE: PRT
<213> ORGANISM: Dengue 4 virus

<400> SEQUENCE: 3

Arg Lys Arg Ser Thr Ile Thr Leu Leu Cys
1               5                   10

<210> SEQ ID NO 4
<211> LENGTH: 30
<212> TYPE: DNA
<213> ORGANISM: Dengue 4 virus

<400> SEQUENCE: 4
agaaaaaggt caacgataac attgctgtgc                                    30

<210> SEQ ID NO 5
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 5

Arg Lys Arg Ser Ala Val Thr Gly Ile Ala
1               5                   10

<210> SEQ ID NO 6
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 6
agaaaaaggt ctgcagtgac cggaattgca                                    30

<210> SEQ ID NO 7
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 7

Arg Lys Arg Ser Ala Gly Thr Gly Ile Ala
1               5                   10

<210> SEQ ID NO 8
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 8
agaaaaaggt ctgcagggac cggaattgca                                    30
```

```
<210> SEQ ID NO 9
<211> LENGTH: 10
<212> TYPE: PRT
<213> ORGANISM: Artificial Sequence
<220> FEATURE:
<223> OTHER INFORMATION: West Nile/Dengue 4 virus chimera

<400> SEQUENCE: 9

Arg Lys Arg Ser Ala Asp Thr Gly Ile Ala
 1               5                  10

<210> SEQ ID NO 10
<211> LENGTH: 30
<212> TYPE: DNA
<213> ORGANISM: Artificial Sequence
<220> FEATURE:
<223> OTHER INFORMATION: West Nile/Dengue 4 virus chimera

<400> SEQUENCE: 10
agaaaaaggt ctgcagacac cggaattgca                                     30

<210> SEQ ID NO 11
<211> LENGTH: 10
<212> TYPE: PRT
<213> ORGANISM: Artificial Sequence
<220> FEATURE:
<223> OTHER INFORMATION: West Nile/Dengue4 chimera

<400> SEQUENCE: 11

Arg Lys Arg Ser Ala Asp Thr Gly Thr Ala
 1               5                  10

<210> SEQ ID NO 12
<211> LENGTH: 30
<212> TYPE: DNA
<213> ORGANISM: Artificial Sequence
<220> FEATURE:
<223> OTHER INFORMATION: West Nile/Dengue4 chimera

<400> SEQUENCE: 12
agaaaaaggt ctgcagacac cggaactgca                                     30

<210> SEQ ID NO 13
<211> LENGTH: 5
<212> TYPE: PRT
<213> ORGANISM: West Nile Virus

<400> SEQUENCE: 13

Ile Asn Ala Arg Asp
 1               5

<210> SEQ ID NO 14
<211> LENGTH: 15
<212> TYPE: DNA
<213> ORGANISM: West Nile Virus

<400> SEQUENCE: 14
atcaatgctc gtgat                                                     15

<210> SEQ ID NO 15
<211> LENGTH: 5
<212> TYPE: PRT
<213> ORGANISM: Dengue 4 virus

<400> SEQUENCE: 15
```

Leu Asn Ser Arg Asn
1               5

<210> SEQ ID NO 16
<211> LENGTH: 15
<212> TYPE: DNA
<213> ORGANISM: Dengue 4 virus

<400> SEQUENCE: 16
ctgaactcga ggaac                                                          15

<210> SEQ ID NO 17
<211> LENGTH: 5
<212> TYPE: PRT
<213> ORGANISM: Artificial Sequence
<220> FEATURE:
<223> OTHER INFORMATION: West Nile/Dengue 4 virus chimera

<400> SEQUENCE: 17

Ile Asn Ser Arg Asn
1               5

<210> SEQ ID NO 18
<211> LENGTH: 15
<212> TYPE: DNA
<213> ORGANISM: Artificial Sequence
<220> FEATURE:
<223> OTHER INFORMATION: West Nile/Dengue 4 virus chimera

<400> SEQUENCE: 18
atcaactcga ggaac                                                          15

<210> SEQ ID NO 19
<211> LENGTH: 51
<212> TYPE: DNA
<213> ORGANISM: Dengue 4

<400> SEQUENCE: 19
ggcccgaagc caggaggaag cuguacuccu gguggaagga cuagagguua g                  51

<210> SEQ ID NO 20
<211> LENGTH: 47
<212> TYPE: DNA
<213> ORGANISM: Dengue 4

<400> SEQUENCE: 20
ggggcccgaa gccaggagga agcuguacuc cugguggaag gacuaga                       47

<210> SEQ ID NO 21
<211> LENGTH: 16
<212> TYPE: DNA
<213> ORGANISM: Artificial Sequence
<220> FEATURE:
<223> OTHER INFORMATION: Dengue4 delta 30

<400> SEQUENCE: 21
ggggcccaag acuaga                                                         16

<210> SEQ ID NO 22
<211> LENGTH: 46
<212> TYPE: DNA
<213> ORGANISM: Dengue 1

<400> SEQUENCE: 22

```
gggcccaac accaggggaa gcuguacccu ggugguaagg acuaga                    46

<210> SEQ ID NO 23
<211> LENGTH: 16
<212> TYPE: DNA
<213> ORGANISM: Artificial Sequence
<220> FEATURE:
<223> OTHER INFORMATION: Dengue1 delta 30

<400> SEQUENCE: 23
ggggcccaag acuaga                                                    16

<210> SEQ ID NO 24
<211> LENGTH: 46
<212> TYPE: DNA
<213> ORGANISM: Dengue 2

<400> SEQUENCE: 24
ggggcccaag gugagaugaa gcuguagucu cacuggaagg acuaga                   46

<210> SEQ ID NO 25
<211> LENGTH: 47
<212> TYPE: DNA
<213> ORGANISM: Dengue 3

<400> SEQUENCE: 25
ggggcccgag cucugaggga agcuguaccu ccuugcaaag gacuaga                  47

<210> SEQ ID NO 26
<211> LENGTH: 82
<212> TYPE: DNA
<213> ORGANISM: Dengue 1

<400> SEQUENCE: 26
gcagcagcgg ggcccaacac caggggaagc uguacccugg gguaaggac uagagguuag     60 aggagacccc ccgcaacaac aa                                             82

<210> SEQ ID NO 27
<211> LENGTH: 83
<212> TYPE: DNA
<213> ORGANISM: Dengue 4

<400> SEQUENCE: 27
agcaaaaggg ggcccgaagc caggaggaag cuguacuccu gguggaagga cuagagguua    60
gaggagaccc ccccaacaca aaa                                            83

<210> SEQ ID NO 28
<211> LENGTH: 84
<212> TYPE: DNA
<213> ORGANISM: Dengue 2

<400> SEQUENCE: 28
agcaacaaug ggggcccaag gugagaugaa gcuguagucu cacuggaagg acuagagguu    60
agaggagacc ccccaaaaac aaaa                                           84

<210> SEQ ID NO 29
<211> LENGTH: 83
<212> TYPE: DNA
<213> ORGANISM: Dengue 3

<400> SEQUENCE: 29
gcagcagcgg ggcccgagcu cugagggaag cuguaccucc uugcaaagga cuagagguua    60
```
gaggagaccc cccgcaaaua aaa 83

<210> SEQ ID NO 30
<211> LENGTH: 15159
<212> TYPE: DNA
<213> ORGANISM: Artificial Sequence
<220> FEATURE:
<223> OTHER INFORMATION: Dengue2 (Tonga/74) plasmid p2

<400> SEQUENCE: 30
agttgttagt ctacgtggac cgacaaagac agattctttg agggagctaa gctcaacgta 60
gttctaactg tttttgatt agagagcaga tctctgatga ataaccaacg gaaaaaggcg 120
agaaacacgc ctttcaatat gctgaaacgc gagagaaacc gcgtgtcaac tgtacaacag 180
ttgacaaaga gattctcact tggaatgctg cagggacgag gaccactaaa attgttcatg 240
gccctggtgg cattccttcg tttcctaaca atcccaccaa cagcagggat attaaaaaga 300
tggggaacaa ttaaaaaatc aaaggctatt aatgttctga gaggcttcag gaaagagatt 360
ggaaggatgc tgaatatctt aaacaggaga cgtagaactg taggcatgat catcatgctg 420
actccaacag tgatggcgtt tcatctgacc acacgcaacg gagaaccaca catgattgtc 480
agtagacaag aaaaagggaa aagccttctg ttcaagacaa aggatggcac gaacatgtgt 540
accctcatgg ccatggacct tggtgagttg tgtgaagaca caatcacgta taaatgtcct 600
tttctcaagc agaacgaacc agaagacata gattgttggt gcaactccac gtccacatgg 660
gtaacttatg ggacatgtac caccacagga gagcacagaa gagaaaaaag atcagtggcg 720
cttgttccac acgtgggaat gggattggag acacgaactg aaacatggat gtcatcagaa 780
ggggcctgga aacatgccca gagaattgaa acttggattc tgagacatcc aggctttacc 840
ataatggccg caatcctggc atacaccata gggacgacgc atttccaaag agtcctgata 900
ttcatcctac tgacagccat cgctccttca atgacaatgc gctgcatagg aatatcaaat 960
agggactttg tggaaggagt gtcaggaggg agttgggttg acatagtttt agaacatgga 1020
agttgtgtga cgacgatggc aaaaaacaaa ccaacactgg actttgaact gataaaaaca 1080
gaagccaaac aacctgccac cttaaggaag tactgtatag aggccaaact gaccaacacg 1140
acaacagact cgcgctgccc aacacaaggg gaacccaccc tgaatgaaga gcaggacaaa 1200
aggtttgtct gcaaacattc catggtagac agaggatggg gaaatggatg tggattgttt 1260
ggaaaaggag gcatcgtgac ctgtgctatg ttcacatgca aaaagaacat ggaaggaaaa 1320
attgtgcagc cagaaaacct ggaatacact gtcgtgataa cacctcattc aggggaagaa 1380
catgcagtgg gaaatgacac aggaaaacat ggtaaagaag tcaagataac accacagagc 1440
tccatcacag aggcggaact gacaggctat ggcactgtta cgatggagtg ctctccaaga 1500
acgggcctcg acttcaatga gatggtgttg ctgcaaatgg aagacaaagc ctggctggtg 1560
cacagacaat ggttcctaga cctaccgttg ccatggctgc ccggagcaga cacacaagga 1620
tcaaattgga tacagaaaga aacactggtc accttcaaaa atccccatgc gaaaaaacag 1680
gatgttgttg tcttaggatc ccaagagggg gccatgcata cagcactcac aggggctacg 1740
gaaatccaga tgtcatcagg aaacctgctg ttcacaggac atctcaagtg caggctgaga 1800
atggacaaat tacaacttaa agggatgtca tactccatgt gcacaggaaa gtttaaaatt 1860
gtgaaggaaa tagcagaaac acaacatgga acaatagtca ttagagtaca atatgaagga 1920
gacggctctc catgcaagat cccctttgag ataatggatc tggaaaaaag acatgttttg 1980

```
ggccgcctga tcacagtcaa cccaattgta acagaaaagg acagtccagt caacatagaa    2040
gcagaacctc cattcggaga cagctacatc atcataggag tggaaccagg acaattgaag    2100
ctggactggt tcaagaaagg aagttccatc ggccaaatgt ttgagacaac aatgagggga    2160
gcgaaaagaa tggccatttt gggtgacaca gcctgggatt ttggatctct gggaggagtg    2220
ttcacatcaa taggaaaggc tctccaccag ttttttggag caatctacgg ggctgctttc    2280
agtggggtct catggactat gaagatcctc ataggagtta tcatcacatg gataggaatg    2340
aactcacgta gcactagtct gagcgtgtca ctggtgttag tgggaatcgt gacactttac    2400
ttgggagtta tggtgcaggc cgatagtggt tgcgttgtga gctggaagaa caaagaacta    2460
aaatgtggca gtggaatatt cgtcacagat aacgtgcata catggacaga acaatacaag    2520
ttccaaccag aatccccttc aaaactggcc tcagccatcc agaaagcgca tgaagagggc    2580
atctgtggaa tccgctcagt aacaagactg gaaaatctta tgtggaaaca gataacatca    2640
gaattgaatc atattctatc agaaaatgaa gtgaaactga ccatcatgac aggagacatc    2700
aaaggaatca tgcaggtagg aaaacgatct ttgcggcctc aacccactga gttgaggtat    2760
tcatggaaaa catggggtaa agcgaaaatg ctctccacag aactccacaa tcagaccttc    2820
ctcattgatg gtcccgaaac agcagaatgc cccaacacaa acagagcttg gaattcactg    2880
gaagttgagg actacggctt tggagtattc actaccaata tatggctaag attgagagaa    2940
aagcaggatg tattttgtga ctcaaaactc atgtcagcgg ccataaagga caacagagcc    3000
gtccatgctg atatgggtta ttggatagaa agcgcactca atgatacatg gaagatagag    3060
aaagcttctt tcattgaagt caaaagttgc cactggccaa agtcacacac cctatggagt    3120
aatggagtgc tagaaagcga gatggtcatt ccaaagaatt tcgctggacc agtgtcacaa    3180
cataataaca gaccaggcta ttacacacaa acagcaggac cttggcatct aggcaagctt    3240
gagatggact ttgatttctg cgaagggact acagtggtgg taaccgagaa ctgtggaaac    3300 agagggcct ctttaagaac aaccactgcc tcaggaaaaac tcataacgga atggtgttgt    3360
cgatcttgca cactaccacc actaagatac agaggtgagg atggatgttg gtacgggatg    3420
gaaatcagac cattgaaaga aaagaagaa atctggtca gttctctggt tacagccgga    3480
catgggcaga ttgacaattt ctcattagga atcttgggaa tggcactgtt ccttgaagaa    3540
atgctcagga ctcgagtagg aacaaaacat gcaatattac tcgtcgcagt ttctttcgtg    3600
acgctaatca cagggaacat gtcttttaga gacctgggaa gagtgatggt tatggtgggt    3660
gccaccatga cagatgacat aggcatgggt gtgacttatc tcgctctact agcagctttt    3720
agagtcagac caacctttgc agctggactg ctcttgagaa aactgacctc caaggaatta    3780
atgatgacta ccataggaat cgttcttctc tcccagagta gcataccaga gaccattctt    3840
gaactgaccg acgcgttagc tctaggcatg atggtcctca gatggtgag aaacatggaa    3900 aaatatcagc tggcagtgac catcatggct atttttgtgcg tcccaaatgc tgtgatatta    3960
cagaacgcat ggaaagtgag ttgcacaata ttggcagtgg tgtctgtttc ccccctgctc    4020
ttaacatcct cacaacagaa agcggactgg ataccattag cgttgacgat caaaggtctt    4080
aatccaacag ccatttttct aacaaccctc tcaagaacca acaagaaaag gagctggcct    4140
ttaaatgagg ccatcatggc ggttgggatg gtgagtatct tggccagctc tctcttaaag    4200
aatgacatcc ccatgacagg accattagtg gctggagggc tccttactgt gtgctacgtg    4260
ctaactgggc ggtcagccga tctggaatta gagagagcta ccgatgtcaa atgggatgac    4320
caggcagaga tatcaggtag cagtccaatc ctgtcaataa caatatcaga agatggcagc    4380
```

```
atgtcaataa agaatgaaga ggaagagcaa acactgacta tactcattag aacaggattg    4440
cttgtgatct caggactctt tccggtatca ataccaatta cagcagcagc atggtatctg    4500
tgggaagtaa agaaacaacg ggctggagtg ctgtgggatg tcccctcacc accacccgtg    4560
ggaaaagctg aattggaaga tggagcctac agaatcaagc aaaaaggaat ccttggatat    4620
tcccagatcg gagctggagt ttacaaagaa ggaacatttc acacaatgtg gcacgtcaca    4680
cgtggcgctg tcctaatgca taaggggaag aggattgaac catcatgggc ggacgtcaag    4740
aaagacttaa tatcatatgg aggaggttgg aagctagaag gagaatggaa agaaggagaa    4800
gaagtccagg tcttggcatt ggagccaggg aaaaatccaa gagccgtcca aacaaagcct    4860
ggccttttta gaaccaacac tggaaccata ggtgccgtat ctctggactt ttcccctggg    4920
acgtcaggat ctccaatcgt cgacaaaaaa ggaaaagttg taggtctcta tggcaatggt    4980
gtcgttacaa ggagtggagc atatgtgagt gccatagctc agactgaaaa aagcattgaa    5040
gacaatccag agattgaaga tgacatcttt cgaaagagaa gattgactat catggatctc    5100
cacccaggag caggaaagac aaagagatac ctcccggcca tagtcagaga ggccataaaa    5160
agaggcttga gaacactaat cctagccccc actagagtcg tggcagctga atgtgaggaa    5220
gcccttagag gacttccaat aagataccaa actccagcta tcagggctga gcacaccggg    5280
cgggagattg tagacttaat gtgtcatgcc acatttacca tgaggctgct atcaccaatc    5340
agggtgccaa attacaacct gatcatcatg gacgaagccc atttacaga tccagcaagc    5400 atagcagcta ggggatacat ctcaactcga gtggagatgg gggaggcagc tggaattttt    5460
atgacagcca ctcctccggg tagtagagat ccatttcctc agagcaatgc accaattatg    5520
gacgaagaaa gagaaattcc ggaacgttca tggaactctg gcacgagtg ggtcacggat    5580 tttaaggaa agactgtctg gtttgttcca agcataaaaa ccggaaatga catagcagcc    5640
tgcctgagaa agaatggaaa gagggtgata caactcagta ggaagacctt tgattctgaa    5700
tatgtcaaga ctagaaccaa tgactgggat ttcgtggtta caactgacat ctcggaaatg    5760
ggcgccaact ttaaagctga gagggtcata daccccagac gctgcatgaa accagttata    5820
ttgacagacg gcgaagagcg ggtgattctg gcaggaccca tgccagtgac ccactctagt    5880
gcagcacaaa aagagggag aataggaagg aatccaagga atgaaaatga tcaatatata    5940
tatatggggg aaccactgga aaatgatgaa gactgtgcgc actggaagga agctaagatg    6000
ctcctagata tatcaacac acctgaagga atcattccca gcttgttcga gccagagcgt    6060
gaaaaggtgg atgccattga cggtgaatat cgcttgagag agaagcacg gaaaactttt    6120 gtggacctaa tgagaagagg agacctacca gtctggttgg cttataaagt ggcagctgaa    6180
ggtatcaact acgcagacag aagatggtgt tttgacggaa ccagaaacaa tcaaatcttg    6240
gaagaaaatg tggaagtgga atctggaca aaggaagggg aaaggaaaaa attgaaacct    6300
agatggttag atgctaggat ctactccgac ccactggcgc taaagagtt caaggaattt    6360 gcagccggaa gaaagtccct aaccctgaac ctaattacag atgggcag actcccaact    6420 tttatgactc agaaggccag agatgcacta gacaacttgg cggtgctgca cacggctgaa    6480
gcgggtggaa aggcatacaa tcatgctctc agtgaattac cggagaccct ggagacattg    6540
cttttgctga cactgttggc cacagtcacg ggaggaatct tcctattcct gatgagcgga    6600
aggggtatgg ggaagatgac cctgggaatg tgctgcataa tcacggccag catcctctta    6660
tggtatgcac aaatacagcc acattggata gcagcctcaa taatattgga gttctttctc    6720
```

```
atagtcttgc tcattccaga accagaaaag cagaggacac ctcaggataa tcaattgact    6780
tatgtcatca tagccatcct cacagtggtg gccgcaacca tggcaaacga aatgggtttt    6840
ctggaaaaaa caaagaaaga cctcggactg ggaaacattg caactcagca acctgagagc    6900
aacattctgg acatagatct acgtcctgca tcagcatgga cgttgtatgc cgtggctaca    6960
acatttatca caccaatgtt gagacatagc attgaaaatt cctcagtaaa tgtgtcccta    7020
acagccatag ctaaccaagc cacagtgcta atgggtctcg gaaaaggatg gccattgtca    7080
aagatggaca ttggagttcc cctccttgct attgggtgtt actcacaagt caaccctata    7140
accctcacag cggctcttct tttattggta gcacattatg ccatcatagg accgggactt    7200
caagccaaag caactagaga agctcagaaa agagcagcag cgggcatcat gaaaaaccca    7260
actgtggatg gaataacagt gatagatcta gatccaatac cctatgatcc aaagtttgaa    7320
aagcagttgg gacaagtaat gctcctagtc ctctgcgtga cccaagtgct gatgatgagg    7380
actacgtggg ctttgtgtga agccttaact ctagcaactg gacccgtgtc cacattgtgg    7440
gaaggaaatc cagggagatt ctggaacaca accattgcag tgtcaatggc aaacatcttt    7500
agagggagtt acctggctgg agctggactt ctcttttcta tcatgaagaa cacaaccagc    7560
acgagaagag gaactggcaa tataggagaa acgttaggag agaaatggaa aagcagactg    7620
aacgcattgg ggaaaagtga attccagatc tacaaaaaaa gtggaattca agaagtggac    7680
agaaccttag caaagaagg cattaaaaga ggagaaacgg atcatcacgc tgtgtcgcga    7740
ggctcagcaa aactgagatg gttcgttgaa aggaatttgg tcacaccaga agggaaagta    7800
gtggaccttg gttgtggcag aggggggctgg tcatactatt gtggaggatt aaagaatgta    7860
agagaagtta aggcttaac aaaggagga ccaggacacg aagaacctat ccctatgtca    7920
acatatgggt ggaatctagt acgcttacag agcggagttg atgttttttt tgttccacca    7980
gagaagtgtg acacattgtt gtgtgacata ggggaatcat caccaaatcc cacggtagaa    8040
gcgggacgaa cactcagagt cctcaaccta gtggaaaatt ggctgaacaa taacacccaa    8100
ttttgcgtaa aggttcttaa cccgtacatg ccctcagtca ttgaaagaat ggaaacctta    8160
caacggaaat acgaggagc cttggtgaga aatccactct cacggaattc cacacatgag    8220
atgtactggg tgtccaatgc ttccgggaac atagtgtcat cagtgaacat gatttcaaga    8280
atgctgatca acagattcac tatgagacac aagaaggcca cctatgagcc agatgtcgac    8340
ctcggaagcg gaacccgcaa tattggaatt gaaagtgaga caccgaacct agacataatt    8400
gggaaaagaa tagaaaaaat aaaacaagag catgaaacgt catggcacta tgatcaagac    8460
cacccataca aaacatgggc ttaccatggc agctatgaaa caaaacagac tggatcagca    8520
tcatccatgg tgaacggagt agtcagattg ctgacaaaac cctgggacgt tgttccaatg    8580
gtgacacaga tggcaatgac agacacaact ccttttggac aacagcgcgt cttcaaagag    8640
aaggtggata cgagaaccca agaaccaaaa gaaggcacaa aaaaactaat gaaaatcacg    8700
gcagagtggc tctggaaaga actaggaaag aaaaagacac ctagaatgtg taccagagaa    8760
gaattcacaa aaaaggtgag aagcaatgca gccttggggg ccatattcac cgatgagaac    8820
aagtggaaat cggcgcgtga agccgttgaa gatagtaggt ttgggagct ggttgacaag    8880
gaaaggaacc tccatcttga agggaaatgt gaaacatgtg tatacaacat gatggggaaa    8940
agagagaaaa aactaggaga gtttggtaaa gcaaaggca gcagagccat atggtacatg    9000
tggctcggag cacgcttctt agagtttgaa gccctaggat ttttgaatga agaccattgg    9060
ttctccagag agaactccct gagtggagtg gaaggagaag ggctgcataa gctaggttac    9120
```

```
atcttaagag aggtgagcaa gaaagaagga ggagcaatgt atgccgatga caccgcaggc   9180
tgggacacaa gaatcacaat agaggatttg aaaaatgaag aaatgataac gaaccacatg   9240
gcaggagaac acaagaaact tgccgaggcc attttttaaat tgacgtacca aaacaaggtg  9300
gtgcgtgtgc aaagaccaac accaagaggc acagtaatgg acatcatatc gagaagagac   9360
caaaggggta gtggacaagt tggcacctat ggcctcaaca ctttcaccaa catggaagca   9420
caactaatta ggcaaatgga gggggaagga atcttcaaaa gcatccagca cttgacagcc   9480
tcagaagaaa tcgctgtgca agattggcta gtaagagtag ggcgtgaaag gttgtcaaga   9540
atggccatca gtggagatga ttgtgttgtg aaacctttag atgatagatt tgcaagagct   9600
ctaacagctc taaatgacat gggaaaggtt aggaaggaca tacagcaatg ggagccctca   9660
agaggatgga acgactggac gcaggtgccc ttctgttcac accattttca cgagttaatt   9720
atgaaagatg gtcgcacact cgtagttcca tgcagaaacc aagatgaatt gatcggcaga   9780
gcccgaattt cccagggagc tgggtggtct ttacgggaga cggcctgttt ggggaagtct   9840
tacgcccaaa tgtggagctt gatgtacttc cacagacgtg atctcaggct agcggcaaat   9900
gccatctgct cggcagtccc atcacactgg attccaacaa gccggacaac ctggtccata   9960
cacgccagcc atgaatggat gacgacggaa gacatgttga cagtttggaa cagagtgtgg  10020
atcctagaaa atccatggat ggaagacaaa actccagtgg aatcatggga ggaaatccca  10080
tacctgggaa aaagagaaga ccaatggtgc ggctcgctga ttgggctgac aagcagagcc  10140
acctgggcga agaatatcca gacagcaata aaccaagtca gatccctcat ggcaatgag  10200 gaatacacag attacatgcc atccatgaaa agattcagaa gagaagagga agaggcagga  10260
gttttgtggt agaaaaacat gaaacaaaac agaagtcagg tcggattaag ccatagtacg  10320
ggaaaaacta tgctacctgt gagccccgtc aaggacgtt aaaagaagtc aggccatttt   10380
gatgccatag cttgagcaaa ctgtgcagcc tgtagctcca cctgagaagg tgtaaaaaat  10440
ccgggaggcc acaaaccatg gaagctgtac gcatggcgta gtggactagc ggttagagga  10500 gaccctccc ttacagatcg cagcaacaat gggggcccaa ggtgagatga agctgtagtc   10560
tcactggaag gactagaggt tagaggagac ccccccaaaa caaaaaacag catattgacg  10620
ctgggaaaga ccagagatcc tgctgtctcc tcagcatcat tccaggcaca ggacgccaga  10680
aaatggaatg gtgctgttga atcaacaggt tctggtaccg gtaggcatcg tggtgtcacg  10740
ctcgtcgttt ggtatggctt cattcagctc cggttcccaa cgatcaaggc gagttacatg  10800
atcccccatg ttgtgcaaaa aagcggttag ctccttcggt cctccgatcg ttgtcagaag  10860
taagttggcc gcagtgttat cactcatggt tatggcagca ctgcataatt ctcttactgt  10920
catgccatcc gtaagatgct tttctgtgac tggtgagtac tcaaccaagt cattctgaga  10980
atagtgtatg cggcgaccga gttgctcttg cccggcgtca acacgggata ataccgcgcc  11040
acatagcaga actttaaaag tgctcatcat tggaaaacgt tcttcgggc gaaaactctc   11100 aaggatctta ccgctgttga gatccagttc gatgtaaccc actcgtgcac ccaactgatc  11160
ttcagcatct tttactttca ccagcgtttc tgggtgagca aaaacaggaa ggcaaaatgc  11220
cgcaaaaaag ggaataaggg cgacacgaaa atgttgaata ctcatactct ccttttttca  11280
atattattga agcatttatc agggttattg tctcatgagc ggatacatat ttgaatgtat  11340
ttagaaaaat aaacaaatag gggttccgcg cacatttccc cgaaaagtgc cacctgacgt  11400
ctaagaaacc attattatca tgacattaac ctataaaaat aggcgtatca cgaggccctt  11460
```

```
tcgtcttcaa gaattctcat gtttgacagc ttatcatcga taagctttaa tgcggtagtt   11520
tatcacagtt aaattgctaa cgcagtcagg caccgtgtat gaaatctaac aatgcgctca   11580
tcgtcatcct cggcaccgtc accctggatg ctgtaggcat aggcttggtt atgccggtac   11640
tgccgggcct cttgcgggat atcgtccatt ccgacagcat cgccagtcac tatggcgtgc   11700
tgctggcgct atatgcgttg atgcaatttc tatgcgcacc cgttctcgga gcactgtccg   11760
accgctttgg ccgccgccca gtcctgctcg cttcgctact tggagccact atcgactacg   11820
cgatcatggc gaccacaccc gtcctgtgga tcctctacgc cggacgcatc gtggccggca   11880
tcaccggcgc cacaggtgcg gttgctggcg cctatatcgc cgacatcacc gatggggaag   11940
atcgggctcg ccacttcggg ctcatgagcg cttgtttcgg cgtgggtatg gtggcaggcc   12000
ccgtggccgg gggactgttg ggcgccatct ccttgcatgc accattcctt gcggcggcgg   12060
tgctcaacgg cctcaaccta ctactgggct gcttcctaat gcaggagtcg cataagggag   12120
agcgtcgacc gatgcccttg agagccttca acccagtcag ctccttccgg tgggcgcggg   12180
gcatgactat cgtcgccgca cttatgactg tcttctttat catgcaactc gtaggacagg   12240
tgccggcagc gctctgggtc attttcggcg aggaccgctt cgctggagc gcgacgatga   12300
tcggcctgtc gcttgcggta ttcggaatct tgcacgccct cgctcaagcc ttcgtcactg   12360
gtcccgccac caaacgtttc ggcgagaagc aggccattat cgccggcatg gcggccgacg   12420
cgctgggcta cgtcttgctg gcgttcgcga cgcgaggctg gatggccttc cccattatga   12480
ttcttctcgc ttccggcggc atcgggatgc ccgcgttgca ggccatgctg tccaggcagg   12540
tagatgacga ccatcaggga cagcttcaag gatcgctcgc ggctcttacc agcctaactt   12600
cgatcactgg accgctgatc gtcacggcga tttatgccgc ctcggcgagc acatggaacg   12660
ggttggcatg gattgtaggc gccgccctat accttgtctg cctccccgcg ttgcgtcgcg   12720
gtgcatggag ccgggccacc tcgacctgaa tggaagccgg cggcacctcg ctaacggatt   12780
caccactcca agaattggag ccaatcaatt cttgcggaga actgtgaatg cgcaaaccaa   12840
cccttggcag aacatatcca tcgcgtccgc catctccagc agccgcacgc ggcgcatctc   12900
gggcagcgtt gggtcctggc cacgggtgcg catgatcgtg ctcctgtcgt tgaggacccg   12960
gctaggctgg cggggttgcc ttactggtta gcagaatgaa tcaccgatac gcgagcgaac   13020
gtgaagcgac tgctgctgca aaacgtctgc gacctgagca caacatgaa tggtcttcgg   13080
tttccgtgtt tcgtaaagtc tggaaacgcg gaagtcagcg ccctgcacca ttatgttccg   13140
gatctgcatc gcaggatgct gctggctacc ctgtggaaca cctacatctg tattaacgaa   13200
gcgctggcat tgaccctgag tgattttct ctggtcccgc cgcatccata ccgccagttg   13260
tttaccctca caacgttcca gtaaccgggc atgttcatca tcagtaaccc gtatcgtgag   13320
catcctctct cgtttcatcg gtatcattac ccccatgaac agaaatcccc cttacacgga   13380
ggcatcagtg accaaacagg aaaaaaccgc ccttaacatg gcccgcttta tcagaagcca   13440
gacattaacg cttctggaga aactcaacga gctggacgcg gatgaacagg cagacatctg   13500
tgaatcgctt cacgaccacg ctgatgagct ttaccgcagc tgcctcgcgc gtttcggtga   13560
tgacggtgaa aacctctgac acatgcagct cccgagacg gtcacagctt gtctgtaagc   13620
ggatgccggg agcagacaag cccgtcaggg cgcgtcagcg ggtgttggcg ggtgtcgggg   13680
cgcagccatg acccagtcac gtagcgatag cggagtgtat actggcttaa ctatgcggca   13740
tcagagcaga ttgtactgag agtgcaccat atgcggtgtg aaataccgca cagatgcgta   13800
aggagaaaat accgcatcag gcgctcttcc gcttcctcgc tcactgactc gctgcgctcg   13860
```
gtcgttcggc tgcggcgagc ggtatcagct cactcaaagg cggtaatacg gttatccaca 13920
gaatcagggg ataacgcagg aaagaacatg tgagcaaaag gccagcaaaa ggccaggaac 13980
cgtaaaaagg ccgcgttgct ggcgtttttc cataggctcc gcccccctga cgagcatcac 14040
aaaaatcgac gctcaagtca gaggtggcga aacccgacag gactataaag ataccaggcg 14100
tttccccctg gaagctccct cgtgcgctct cctgttccga ccctgccgct taccggatac 14160
ctgtccgcct ttctcccttc gggaagcgtg gcgctttctc atagctcacg ctgtaggtat 14220
ctcagttcgg tgtaggtcgt tcgctccaag ctgggctgtg tgcacgaacc ccccgttcag 14280
cccgaccgct gcgccttatc cggtaactat cgtcttgagt ccaacccggt aagacacgac 14340
ttatcgccac tggcagcagc cactggtaac aggattagca gagcgaggta tgtaggcggt 14400
gctacagagt tcttgaagtg gtggcctaac tacggctaca ctagaaggac agtatttggt 14460
atctgcgctc tgctgaagcc agttaccttc ggaaaaagag ttggtagctc ttgatccggc 14520
aaacaaacca ccgctggtag cggtggtttt tttgtttgca agcagcagat tacgcgcaga 14580
aaaaaaggat ctcaagaaga tcctttgatc ttttctacgg ggtctgacgc tcagtggaac 14640
gaaaactcac gttaagggat tttggtcatg agattatcaa aaaggatctt cacctagatc 14700
cttttaaatt aaaaatgaag ttttaaatca atctaaagta tatatgagta aacttggtct 14760
gacagttacc aatgcttaat cagtgaggca cctatctcag cgatctgtct atttcgttca 14820
tccatagttg cctgactccc cgtcgtgtag ataactacga tacgggaggg cttaccatct 14880
ggccccagtg ctgcaatgat accgcgagac ccacgctcac cggctccaga tttatcagca 14940
ataaaccagc cagccggaag ggccgagcgc agaagtggtc ctgcaacttt atccgcctcc 15000
atccagtcta ttaattgttg ccgggaagct agagtaagta gttcgccagt taatagtttg 15060
cgcaacgttg ttgccattgc tgcaagatct ggctagcgat gaccctgctg attggttcgc 15120
tgaccatttc cgggcgcgcc gatttaggtg acactatag 15159

<210> SEQ ID NO 31
<211> LENGTH: 3391
<212> TYPE: PRT
<213> ORGANISM: Dengue 2 (Tonga/74)

<400> SEQUENCE: 31

Met Asn Asn Gln Arg Lys Lys Ala Arg Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Thr Val Gly Met Ile Ile Met Leu Thr Pro Thr Val
100 105 110

Met Ala Phe His Leu Thr Thr Arg Asn Gly Glu Pro His Met Ile Val
115 120 125

Ser Arg Gln Glu Lys Gly Lys Ser Leu Leu Phe Lys Thr Lys Asp Gly
130 135 140

```
Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
            165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
            195                 200                 205

Leu Val Pro His Val Gly Met Gly Leu Glu Thr Arg Thr Glu Thr Trp
            210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
            245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
            275                 280                 285

Arg Asp Phe Val Glu Gly Val Ser Gly Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
            325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Thr Leu Asn Glu Glu Gln Asp Lys
            355                 360                 365

Arg Phe Val Cys Lys His Ser Met Val Asp Arg Gly Trp Gly Asn Gly
            370                 375                 380

Cys Gly Leu Phe Gly Lys Gly Gly Ile Val Thr Cys Ala Met Phe Thr
385                 390                 395                 400

Cys Lys Lys Asn Met Glu Gly Lys Ile Val Gln Pro Glu Asn Leu Glu
            405                 410                 415

Tyr Thr Val Val Ile Thr Pro His Ser Gly Glu Glu His Ala Val Gly
            420                 425                 430

Asn Asp Thr Gly Lys His Gly Lys Glu Val Lys Ile Thr Pro Gln Ser
            435                 440                 445

Ser Ile Thr Glu Ala Glu Leu Thr Gly Tyr Gly Thr Val Thr Met Glu
            450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
            485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
            515                 520                 525

Asp Val Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560
```

-continued

```
Gly His Leu Lys Cys Arg Leu Arg Met Asp Lys Leu Gln Leu Lys Gly
            565                 570                 575
Met Ser Tyr Ser Met Cys Thr Gly Lys Phe Lys Ile Val Lys Glu Ile
            580                 585                 590
Ala Glu Thr Gln His Gly Thr Ile Val Ile Arg Val Gln Tyr Glu Gly
            595                 600                 605
Asp Gly Ser Pro Cys Lys Ile Pro Phe Glu Ile Met Asp Leu Glu Lys
            610                 615                 620
Arg His Val Leu Gly Arg Leu Ile Thr Val Asn Pro Ile Val Thr Glu
625                 630                 635                 640
Lys Asp Ser Pro Val Asn Ile Glu Ala Glu Pro Pro Phe Gly Asp Ser
            645                 650                 655
Tyr Ile Ile Ile Gly Val Glu Pro Gly Gln Leu Lys Leu Asp Trp Phe
            660                 665                 670
Lys Lys Gly Ser Ser Ile Gly Gln Met Phe Glu Thr Thr Met Arg Gly
            675                 680                 685
Ala Lys Arg Met Ala Ile Leu Gly Asp Thr Ala Trp Asp Phe Gly Ser
            690                 695                 700
Leu Gly Gly Val Phe Thr Ser Ile Gly Lys Ala Leu His Gln Val Phe
705                 710                 715                 720
Gly Ala Ile Tyr Gly Ala Ala Phe Ser Gly Val Ser Trp Thr Met Lys
            725                 730                 735
Ile Leu Ile Gly Val Ile Ile Thr Trp Ile Gly Met Asn Ser Arg Ser
            740                 745                 750
Thr Ser Leu Ser Val Ser Leu Val Leu Val Gly Ile Val Thr Leu Tyr
            755                 760                 765
Leu Gly Val Met Val Gln Ala Asp Ser Gly Cys Val Val Ser Trp Lys
            770                 775                 780
Asn Lys Glu Leu Lys Cys Gly Ser Gly Ile Phe Val Thr Asp Asn Val
785                 790                 795                 800
His Thr Trp Thr Glu Gln Tyr Lys Phe Gln Pro Glu Ser Pro Ser Lys
            805                 810                 815
Leu Ala Ser Ala Ile Gln Lys Ala His Glu Glu Gly Ile Cys Gly Ile
            820                 825                 830
Arg Ser Val Thr Arg Leu Glu Asn Leu Met Trp Lys Gln Ile Thr Ser
            835                 840                 845
Glu Leu Asn His Ile Leu Ser Glu Asn Glu Val Lys Leu Thr Ile Met
            850                 855                 860
Thr Gly Asp Ile Lys Gly Ile Met Gln Val Gly Lys Arg Ser Leu Arg
865                 870                 875                 880
Pro Gln Pro Thr Glu Leu Arg Tyr Ser Trp Lys Thr Trp Gly Lys Ala
            885                 890                 895
Lys Met Leu Ser Thr Glu Leu His Asn Gln Thr Phe Leu Ile Asp Gly
            900                 905                 910
Pro Glu Thr Ala Glu Cys Pro Asn Thr Asn Arg Ala Trp Asn Ser Leu
            915                 920                 925
Glu Val Glu Asp Tyr Gly Phe Gly Val Phe Thr Thr Asn Ile Trp Leu
            930                 935                 940
Arg Leu Arg Glu Lys Gln Asp Val Phe Cys Asp Ser Lys Leu Met Ser
945                 950                 955                 960
Ala Ala Ile Lys Asp Asn Arg Ala Val His Ala Asp Met Gly Tyr Trp
            965                 970                 975
Ile Glu Ser Ala Leu Asn Asp Thr Trp Lys Ile Glu Lys Ala Ser Phe
```

-continued

```
                980             985             990
Ile Glu Val Lys Ser Cys His Trp Pro Lys Ser His Thr Leu Trp Ser
            995                 1000                1005
Asn Gly Val Leu Glu Ser Glu Met Val Ile Pro Lys Asn Phe Ala Gly
    1010                1015                1020
Pro Val Ser Gln His Asn Asn Arg Pro Gly Tyr Tyr Thr Gln Thr Ala
1025                1030                1035                1040
Gly Pro Trp His Leu Gly Lys Leu Glu Met Asp Phe Asp Phe Cys Glu
                1045                1050                1055
Gly Thr Thr Val Val Val Thr Glu Asn Cys Gly Asn Arg Gly Pro Ser
                1060                1065                1070
Leu Arg Thr Thr Thr Ala Ser Gly Lys Leu Ile Thr Glu Trp Cys Cys
            1075                1080                1085
Arg Ser Cys Thr Leu Pro Pro Leu Arg Tyr Arg Gly Glu Asp Gly Cys
        1090                1095                1100
Trp Tyr Gly Met Glu Ile Arg Pro Leu Lys Glu Lys Glu Glu Asn Leu
1105                1110                1115                1120
Val Ser Ser Leu Val Thr Ala Gly His Gly Gln Ile Asp Asn Phe Ser
                1125                1130                1135
Leu Gly Ile Leu Gly Met Ala Leu Phe Leu Glu Glu Met Leu Arg Thr
                1140                1145                1150
Arg Val Gly Thr Lys His Ala Ile Leu Leu Val Ala Val Ser Phe Val
            1155                1160                1165
Thr Leu Ile Thr Gly Asn Met Ser Phe Arg Asp Leu Gly Arg Val Met
        1170                1175                1180
Val Met Val Gly Ala Thr Met Thr Asp Asp Ile Gly Met Gly Val Thr
1185                1190                1195                1200
Tyr Leu Ala Leu Leu Ala Ala Phe Arg Val Arg Pro Thr Phe Ala Ala
                1205                1210                1215
Gly Leu Leu Leu Arg Lys Leu Thr Ser Lys Glu Leu Met Met Thr Thr
                1220                1225                1230
Ile Gly Ile Val Leu Leu Ser Gln Ser Ser Ile Pro Glu Thr Ile Leu
            1235                1240                1245
Glu Leu Thr Asp Ala Leu Ala Leu Gly Met Met Val Leu Lys Met Val
    1250                1255                1260
Arg Asn Met Glu Lys Tyr Gln Leu Ala Val Thr Ile Met Ala Ile Leu
1265                1270                1275                1280
Cys Val Pro Asn Ala Val Ile Leu Gln Asn Ala Trp Lys Val Ser Cys
                1285                1290                1295
Thr Ile Leu Ala Val Val Ser Val Ser Pro Leu Leu Leu Thr Ser Ser
                1300                1305                1310
Gln Gln Lys Ala Asp Trp Ile Pro Leu Ala Leu Thr Ile Lys Gly Leu
            1315                1320                1325
Asn Pro Thr Ala Ile Phe Leu Thr Thr Leu Ser Arg Thr Asn Lys Lys
    1330                1335                1340
Arg Ser Trp Pro Leu Asn Glu Ala Ile Met Ala Val Gly Met Val Ser
1345                1350                1355                1360
Ile Leu Ala Ser Ser Leu Leu Lys Asn Asp Ile Pro Met Thr Gly Pro
                1365                1370                1375
Leu Val Ala Gly Gly Leu Leu Thr Val Cys Tyr Val Leu Thr Gly Arg
                1380                1385                1390
Ser Ala Asp Leu Glu Leu Glu Arg Ala Thr Asp Val Lys Trp Asp Asp
            1395                1400                1405
```

```
Gln Ala Glu Ile Ser Gly Ser Ser Pro Ile Leu Ser Ile Thr Ile Ser
    1410                1415                1420

Glu Asp Gly Ser Met Ser Ile Lys Asn Glu Glu Glu Gln Thr Leu
1425                1430                1435                1440

Thr Ile Leu Ile Arg Thr Gly Leu Leu Val Ile Ser Gly Leu Phe Pro
                1445                1450                1455

Val Ser Ile Pro Ile Thr Ala Ala Trp Tyr Leu Trp Glu Val Lys
            1460                1465                1470

Lys Gln Arg Ala Gly Val Leu Trp Asp Val Pro Ser Pro Pro Val
        1475                1480                1485

Gly Lys Ala Glu Leu Glu Asp Gly Ala Tyr Arg Ile Lys Gln Lys Gly
    1490                1495                1500

Ile Leu Gly Tyr Ser Gln Ile Gly Ala Gly Val Tyr Lys Glu Gly Thr
1505                1510                1515                1520

Phe His Thr Met Trp His Val Thr Arg Gly Ala Val Leu Met His Lys
                1525                1530                1535

Gly Lys Arg Ile Glu Pro Ser Trp Ala Asp Val Lys Lys Asp Leu Ile
            1540                1545                1550

Ser Tyr Gly Gly Gly Trp Lys Leu Glu Gly Glu Trp Lys Glu Gly Glu
        1555                1560                1565

Glu Val Gln Val Leu Ala Leu Glu Pro Gly Lys Asn Pro Arg Ala Val
    1570                1575                1580

Gln Thr Lys Pro Gly Leu Phe Arg Thr Asn Thr Gly Thr Ile Gly Ala
1585                1590                1595                1600

Val Ser Leu Asp Phe Ser Pro Gly Thr Ser Gly Ser Pro Ile Val Asp
                1605                1610                1615

Lys Lys Gly Lys Val Val Gly Leu Tyr Gly Asn Gly Val Val Thr Arg
            1620                1625                1630

Ser Gly Ala Tyr Val Ser Ala Ile Ala Gln Thr Glu Lys Ser Ile Glu
        1635                1640                1645

Asp Asn Pro Glu Ile Glu Asp Asp Ile Phe Arg Lys Arg Arg Leu Thr
    1650                1655                1660

Ile Met Asp Leu His Pro Gly Ala Gly Lys Thr Lys Arg Tyr Leu Pro
1665                1670                1675                1680

Ala Ile Val Arg Glu Ala Ile Lys Arg Gly Leu Arg Thr Leu Ile Leu
                1685                1690                1695

Ala Pro Thr Arg Val Val Ala Ala Glu Met Glu Glu Ala Leu Arg Gly
            1700                1705                1710

Leu Pro Ile Arg Tyr Gln Thr Pro Ala Ile Arg Ala Glu His Thr Gly
        1715                1720                1725

Arg Glu Ile Val Asp Leu Met Cys His Ala Thr Phe Thr Met Arg Leu
    1730                1735                1740

Leu Ser Pro Ile Arg Val Pro Asn Tyr Asn Leu Ile Ile Met Asp Glu
1745                1750                1755                1760

Ala His Phe Thr Asp Pro Ala Ser Ile Ala Ala Arg Gly Tyr Ile Ser
                1765                1770                1775

Thr Arg Val Glu Met Gly Glu Ala Ala Gly Ile Phe Met Thr Ala Thr
            1780                1785                1790

Pro Pro Gly Ser Arg Asp Pro Phe Pro Gln Ser Asn Ala Pro Ile Met
        1795                1800                1805

Asp Glu Glu Arg Glu Ile Pro Glu Arg Ser Trp Asn Ser Gly His Glu
    1810                1815                1820
```

```
Trp Val Thr Asp Phe Lys Gly Lys Thr Val Trp Phe Val Pro Ser Ile
1825                1830                1835                1840

Lys Thr Gly Asn Asp Ile Ala Ala Cys Leu Arg Lys Asn Gly Lys Arg
         1845                1850                1855

Val Ile Gln Leu Ser Arg Lys Thr Phe Asp Ser Glu Tyr Val Lys Thr
         1860                1865                1870

Arg Thr Asn Asp Trp Asp Phe Val Val Thr Thr Asp Ile Ser Glu Met
    1875                1880                1885

Gly Ala Asn Phe Lys Ala Glu Arg Val Ile Asp Pro Arg Arg Cys Met
    1890                1895                1900

Lys Pro Val Ile Leu Thr Asp Gly Glu Glu Arg Val Ile Leu Ala Gly
1905                1910                1915                1920

Pro Met Pro Val Thr His Ser Ser Ala Ala Gln Arg Arg Gly Arg Ile
         1925                1930                1935

Gly Arg Asn Pro Arg Asn Glu Asn Asp Gln Tyr Ile Tyr Met Gly Glu
         1940                1945                1950

Pro Leu Glu Asn Asp Glu Asp Cys Ala His Trp Lys Glu Ala Lys Met
         1955                1960                1965

Leu Leu Asp Asn Ile Asn Thr Pro Glu Gly Ile Ile Pro Ser Leu Phe
    1970                1975                1980

Glu Pro Glu Arg Glu Lys Val Asp Ala Ile Asp Gly Glu Tyr Arg Leu
1985                1990                1995                2000

Arg Gly Glu Ala Arg Lys Thr Phe Val Asp Leu Met Arg Arg Gly Asp
         2005                2010                2015

Leu Pro Val Trp Leu Ala Tyr Lys Val Ala Ala Glu Gly Ile Asn Tyr
         2020                2025                2030

Ala Asp Arg Arg Trp Cys Phe Asp Gly Thr Arg Asn Asn Gln Ile Leu
         2035                2040                2045

Glu Glu Asn Val Glu Val Glu Ile Trp Thr Lys Glu Gly Glu Arg Lys
2050                2055                2060

Lys Leu Lys Pro Arg Trp Leu Asp Ala Arg Ile Tyr Ser Asp Pro Leu
2065                2070                2075                2080

Ala Leu Lys Glu Phe Lys Glu Phe Ala Ala Gly Arg Lys Ser Leu Thr
         2085                2090                2095

Leu Asn Leu Ile Thr Glu Met Gly Arg Leu Pro Thr Phe Met Thr Gln
         2100                2105                2110

Lys Ala Arg Asp Ala Leu Asp Asn Leu Ala Val Leu His Thr Ala Glu
         2115                2120                2125

Ala Gly Gly Lys Ala Tyr Asn His Ala Leu Ser Glu Leu Pro Glu Thr
         2130                2135                2140

Leu Glu Thr Leu Leu Leu Leu Thr Leu Leu Ala Thr Val Thr Gly Gly
2145                2150                2155                2160

Ile Phe Leu Phe Leu Met Ser Gly Arg Gly Met Gly Lys Met Thr Leu
         2165                2170                2175

Gly Met Cys Cys Ile Ile Thr Ala Ser Ile Leu Leu Trp Tyr Ala Gln
         2180                2185                2190

Ile Gln Pro His Trp Ile Ala Ala Ser Ile Ile Leu Glu Phe Phe Leu
         2195                2200                2205

Ile Val Leu Leu Ile Pro Glu Pro Glu Lys Gln Arg Thr Pro Gln Asp
         2210                2215                2220

Asn Gln Leu Thr Tyr Val Ile Ile Ala Ile Leu Thr Val Val Ala Ala
2225                2230                2235                2240

Thr Met Ala Asn Glu Met Gly Phe Leu Glu Lys Thr Lys Lys Asp Leu
```

```
            2245              2250              2255

Gly Leu Gly Asn Ile Ala Thr Gln Gln Pro Glu Ser Asn Ile Leu Asp
            2260              2265              2270

Ile Asp Leu Arg Pro Ala Ser Ala Trp Thr Leu Tyr Ala Val Ala Thr
            2275              2280              2285

Thr Phe Ile Thr Pro Met Leu Arg His Ser Ile Glu Asn Ser Ser Val
            2290              2295              2300

Asn Val Ser Leu Thr Ala Ile Ala Asn Gln Ala Thr Val Leu Met Gly
2305              2310              2315              2320

Leu Gly Lys Gly Trp Pro Leu Ser Lys Met Asp Ile Gly Val Pro Leu
            2325              2330              2335

Leu Ala Ile Gly Cys Tyr Ser Gln Val Asn Pro Ile Thr Leu Thr Ala
            2340              2345              2350

Ala Leu Leu Leu Leu Val Ala His Tyr Ala Ile Ile Gly Pro Gly Leu
            2355              2360              2365

Gln Ala Lys Ala Thr Arg Glu Ala Gln Lys Arg Ala Ala Ala Gly Ile
            2370              2375              2380

Met Lys Asn Pro Thr Val Asp Gly Ile Thr Val Ile Asp Leu Asp Pro
2385              2390              2395              2400

Ile Pro Tyr Asp Pro Lys Phe Glu Lys Gln Leu Gly Gln Val Met Leu
            2405              2410              2415

Leu Val Leu Cys Val Thr Gln Val Leu Met Met Arg Thr Thr Trp Ala
            2420              2425              2430

Leu Cys Glu Ala Leu Thr Leu Ala Thr Gly Pro Val Ser Thr Leu Trp
            2435              2440              2445

Glu Gly Asn Pro Gly Arg Phe Trp Asn Thr Thr Ile Ala Val Ser Met
            2450              2455              2460

Ala Asn Ile Phe Arg Gly Ser Tyr Leu Ala Gly Ala Gly Leu Leu Phe
2465              2470              2475              2480

Ser Ile Met Lys Asn Thr Thr Ser Thr Arg Arg Gly Thr Gly Asn Ile
            2485              2490              2495

Gly Glu Thr Leu Gly Glu Lys Trp Lys Ser Arg Leu Asn Ala Leu Gly
            2500              2505              2510

Lys Ser Glu Phe Gln Ile Tyr Lys Lys Ser Gly Ile Gln Glu Val Asp
            2515              2520              2525

Arg Thr Leu Ala Lys Glu Gly Ile Lys Arg Gly Glu Thr Asp His His
            2530              2535              2540

Ala Val Ser Arg Gly Ser Ala Lys Leu Arg Trp Phe Val Glu Arg Asn
2545              2550              2555              2560

Leu Val Thr Pro Glu Gly Lys Val Val Asp Leu Gly Cys Gly Arg Gly
            2565              2570              2575

Gly Trp Ser Tyr Tyr Cys Gly Gly Leu Lys Asn Val Arg Glu Val Lys
            2580              2585              2590

Gly Leu Thr Lys Gly Gly Pro Gly His Glu Glu Pro Ile Pro Met Ser
            2595              2600              2605

Thr Tyr Gly Trp Asn Leu Val Arg Leu Gln Ser Gly Val Asp Val Phe
            2610              2615              2620

Phe Val Pro Pro Glu Lys Cys Asp Thr Leu Leu Cys Asp Ile Gly Glu
2625              2630              2635              2640

Ser Ser Pro Asn Pro Thr Val Glu Ala Gly Arg Thr Leu Arg Val Leu
            2645              2650              2655

Asn Leu Val Glu Asn Trp Leu Asn Asn Asn Thr Gln Phe Cys Val Lys
            2660              2665              2670
```

-continued

Val Leu Asn Pro Tyr Met Pro Ser Val Ile Glu Arg Met Glu Thr Leu
            2675                2680                2685

Gln Arg Lys Tyr Gly Gly Ala Leu Val Arg Asn Pro Leu Ser Arg Asn
        2690                2695                2700

Ser Thr His Glu Met Tyr Trp Val Ser Asn Ala Ser Gly Asn Ile Val
2705                2710                2715                2720

Ser Ser Val Asn Met Ile Ser Arg Met Leu Ile Asn Arg Phe Thr Met
            2725                2730                2735

Arg His Lys Lys Ala Thr Tyr Glu Pro Asp Val Asp Leu Gly Ser Gly
        2740                2745                2750

Thr Arg Asn Ile Gly Ile Glu Ser Glu Thr Pro Asn Leu Asp Ile Ile
            2755                2760                2765

Gly Lys Arg Ile Glu Lys Ile Lys Gln Glu His Glu Thr Ser Trp His
        2770                2775                2780

Tyr Asp Gln Asp His Pro Tyr Lys Thr Trp Ala Tyr His Gly Ser Tyr
2785                2790                2795                2800

Glu Thr Lys Gln Thr Gly Ser Ala Ser Ser Met Val Asn Gly Val Val
            2805                2810                2815

Arg Leu Leu Thr Lys Pro Trp Asp Val Val Pro Met Val Thr Gln Met
        2820                2825                2830

Ala Met Thr Asp Thr Thr Pro Phe Gly Gln Gln Arg Val Phe Lys Glu
            2835                2840                2845

Lys Val Asp Thr Arg Thr Gln Glu Pro Lys Glu Gly Thr Lys Lys Leu
        2850                2855                2860

Met Lys Ile Thr Ala Glu Trp Leu Trp Lys Glu Leu Gly Lys Lys Lys
2865                2870                2875                2880

Thr Pro Arg Met Cys Thr Arg Glu Glu Phe Thr Lys Lys Val Arg Ser
            2885                2890                2895

Asn Ala Ala Leu Gly Ala Ile Phe Thr Asp Glu Asn Lys Trp Lys Ser
        2900                2905                2910

Ala Arg Glu Ala Val Glu Asp Ser Arg Phe Trp Glu Leu Val Asp Lys
            2915                2920                2925

Glu Arg Asn Leu His Leu Glu Gly Lys Cys Glu Thr Cys Val Tyr Asn
        2930                2935                2940

Met Met Gly Lys Arg Glu Lys Lys Leu Gly Glu Phe Gly Lys Ala Lys
2945                2950                2955                2960

Gly Ser Arg Ala Ile Trp Tyr Met Trp Leu Gly Ala Arg Phe Leu Glu
            2965                2970                2975

Phe Glu Ala Leu Gly Phe Leu Asn Glu Asp His Trp Phe Ser Arg Glu
        2980                2985                2990

Asn Ser Leu Ser Gly Val Glu Gly Glu Gly Leu His Lys Leu Gly Tyr
            2995                3000                3005

Ile Leu Arg Glu Val Ser Lys Lys Glu Gly Gly Ala Met Tyr Ala Asp
        3010                3015                3020

Asp Thr Ala Gly Trp Asp Thr Arg Ile Thr Ile Glu Asp Leu Lys Asn
3025                3030                3035                3040

Glu Glu Met Ile Thr Asn His Met Ala Gly Glu His Lys Lys Leu Ala
            3045                3050                3055

Glu Ala Ile Phe Lys Leu Thr Tyr Gln Asn Lys Val Val Arg Val Gln
        3060                3065                3070

Arg Pro Thr Pro Arg Gly Thr Val Met Asp Ile Ile Ser Arg Arg Asp
            3075                3080                3085

| | | | | | | | | | | | | |
|---|---|---|---|---|---|---|---|---|---|---|---|---|
|Gln|Arg|Gly|Ser|Gly|Gln|Val|Gly|Thr|Tyr|Gly|Leu|Asn|Thr|Phe|Thr|
| 3090| | | | | 3095| | | | 3100| | |

Gln Arg Gly Ser Gly Gln Val Gly Thr Tyr Gly Leu Asn Thr Phe Thr
    3090                3095                3100

Asn Met Glu Ala Gln Leu Ile Arg Gln Met Glu Gly Glu Gly Ile Phe
3105                3110                3115                3120

Lys Ser Ile Gln His Leu Thr Ala Ser Glu Glu Ile Ala Val Gln Asp
        3125                3130                3135

Trp Leu Val Arg Val Gly Arg Glu Arg Leu Ser Arg Met Ala Ile Ser
        3140                3145                3150

Gly Asp Asp Cys Val Val Lys Pro Leu Asp Asp Arg Phe Ala Arg Ala
        3155                3160                3165

Leu Thr Ala Leu Asn Asp Met Gly Lys Val Arg Lys Asp Ile Gln Gln
        3170                3175                3180

Trp Glu Pro Ser Arg Gly Trp Asn Asp Trp Thr Gln Val Pro Phe Cys
3185                3190                3195                3200

Ser His His Phe His Glu Leu Ile Met Lys Asp Gly Arg Thr Leu Val
        3205                3210                3215

Val Pro Cys Arg Asn Gln Asp Glu Leu Ile Gly Arg Ala Arg Ile Ser
        3220                3225                3230

Gln Gly Ala Gly Trp Ser Leu Arg Glu Thr Ala Cys Leu Gly Lys Ser
        3235                3240                3245

Tyr Ala Gln Met Trp Ser Leu Met Tyr Phe His Arg Arg Asp Leu Arg
        3250                3255                3260

Leu Ala Ala Asn Ala Ile Cys Ser Ala Val Pro Ser His Trp Ile Pro
3265                3270                3275                3280

Thr Ser Arg Thr Thr Trp Ser Ile His Ala Ser His Glu Trp Met Thr
        3285                3290                3295

Thr Glu Asp Met Leu Thr Val Trp Asn Arg Val Trp Ile Leu Glu Asn
        3300                3305                3310

Pro Trp Met Glu Asp Lys Thr Pro Val Glu Ser Trp Glu Glu Ile Pro
3315                3320                3325

Tyr Leu Gly Lys Arg Glu Asp Gln Trp Cys Gly Ser Leu Ile Gly Leu
        3330                3335                3340

Thr Ser Arg Ala Thr Trp Ala Lys Asn Ile Gln Thr Ala Ile Asn Gln
3345                3350                3355                3360

Val Arg Ser Leu Ile Gly Asn Glu Glu Tyr Thr Asp Tyr Met Pro Ser
        3365                3370                3375

Met Lys Arg Phe Arg Arg Glu Glu Glu Glu Ala Gly Val Leu Trp
        3380                3385                3390

<210> SEQ ID NO 32
<211> LENGTH: 15053
<212> TYPE: DNA
<213> ORGANISM: Artificial Sequence
<220> FEATURE:
<223> OTHER INFORMATION: Dengue 3 (Sleman/78) plasmid p3

<400> SEQUENCE: 32
agttgttagt ctacgtggac cgacaagaac agtttcgact cggaagcttg c

```
aaacatgctg agcattatca acagacggaa aaagacatcg ctctgtctca tgatgatgtt      420
accagcaaca cttgctttcc acttgacttc acgagatgga gagccgcgca tgattgtggg      480
gaagaatgaa agaggaaaat ccctactttt aagacagcc tctggaatca acatgtgcac       540
actcatagcc atggatttgg gagagatgtg tgatgacacg gtcacctaca aatgccccct      600
cattactgaa gtggagcctg aagacattga ctgctggtgc aaccttacat cgacatgggt     660
gacctacgga acgtgcaatc aagctggaga gcacagacgc gacaaaagat cggtggcgtt      720
agctccccat gtcggcatgg gactggacac acgcacccaa acctggatgt cggctgaagg     780
agcttggaga caggtcgaga aggtagagac atgggccttt aggcacccag ggttcacaat      840
actagcccta tttcttgccc attacatagg cacttccttg acccagaaag tggttatttt     900
catactacta atgctggtca ccccatccat gacaatgaga tgcgtgggag taggaaacag    960
agattttgtg aaggcctat caggagctac gtgggttgac gtggtgctcg agcacggtgg      1020
gtgtgtgact accatggcta agaacaagcc cacgctggat atagagctcc agaagaccga     1080
ggccacccaa ctggcgaccc taaggaaact atgtattgag ggaaaaatta ccaacgtaac    1140
aaccgactca aggtgcccca cccaagggga agcgatttta cctgaggagc aggaccagaa   1200
ccacgtgtgc aagcacacat acgtggacag aggctgggga aacggttgtg gtttgtttgg   1260
caagggaagc ctggtaacat gcgcgaaatt tcaatgtttg gaatcaatag agggaaaagt    1320
ggtgcagcat gagaacctca aatacaccgt catcatcaca gtgcacacag agatcaaca    1380 ccaggtggga aatgaaacgc agggagtcac ggctgagata caccccagg catcaaccgt     1440 tgaagccatc ttacctgaat atggaaccct tgggctagaa tgctcaccac ggacaggttt    1500
agatttcaat gaaatgattt tgttgacaat gaagaacaaa gcatggatgg tacatagaca    1560 atggttttt gacctacctt taccatggac atcaggagct acaacagaaa caccaacctg     1620
gaataagaaa gagcttcttg tgacattcaa aaacgcacat gcaaaaagc aagaagtagt    1680 agtccttgga tcgcaagagg gagcaatgca cacagcactg acaggagcta cagagatcca   1740
aacctcagga ggcacaagta tttttgcggg gcacttaaaa tgtagactca agatggacaa   1800
attggaactc aaggggatga ctatgcaat gtgcttgaat gcctttgtgt tgaagaaaga    1860
agtctccgaa acgcaacatg ggacaatact catcaaggtt gagtacaaag gggaagatgc    1920
accttgcaag attcctttct ccacggagga tggacaaggg aaagcccaca tggcagact   1980 gatcacagct aacccagtgg tgaccaagaa ggaggagcct gtcaatattg aggcagaacc    2040
tccttttggg gaaagcaata tagtaattgg aattggagac aaagccttga aaatcaactg    2100
gtacaagaag ggaagctcga ttgggaagat gttcgaggcc actgccagag gtgcaaggcg   2160
catggccatc ttgggagaca cagcctggga ctttggatca gtaggtggtg ttttaaattc   2220
attaggaaaa atggtgcacc aaatatttgg aagtgcttac acagccctat ttagtggagt    2280
ctcctggata atgaaaattg gaataggtgt ccttttaacc tggataggt tgaattcaaa    2340 aaacactagt atgagcttta gctgcattgt gataggaatc attacactct atctgggagc    2400
cgtggtgcaa gctgacatgg ggtgtgtcat aaactggaaa ggcaaagaac tcaaatgtgg    2460
aagtggaatt ttcgtcacta atgaggtcca cacctggaca gagcaataca atttcaagc     2520 agactccccc aaaagactgg cgacagccat tgcaggcgct tgggagaatg gagtgtgcgg    2580
aatcaggtcg acaaccagaa tggagaacct cttgtggaag caaatagcca atgaactgaa   2640
ctacatatta tgggaaaaca acatcaaatt aacggtagtt gtgggtgata taattggggt   2700
cttagagcaa gggaaagaa cactaacacc acaacccatg gaactaaaat attcatggaa    2760
```

```
aacatgggga aaggcgaaga tagtgacagc tgaaacacaa aattcctctt tcataataga    2820
tgggccaaac acaccagagt gtccaagtgc ctcaagagca tggaatgtgt gggaggtgga    2880
agattacggg ttcggagtct tcacaactaa catatggctg aaactccgag agatgtacac    2940
ccaactatgt gaccacaggc taatgtcggc agccgttaag gatgagaggg ccgtacacgc    3000
cgacatgggc tattggatag aaagccaaaa gaatggaagt tggaagctag aaaaggcatc    3060
cctcatagag gtaaaaacct gcacatggcc aaaatcacac actctttgga gcaatggtgt    3120
gctagagagt gacatgatca tcccaaagag tctggctggt cccatttcgc aacacaacta    3180
caggcccgga taccacaccc aaacggcagg accctggcac ttaggaaaat ggagctgga    3240 cttcaactat tgtgaaggaa caacagttgt catcacagaa aattgtggga caagaggccc    3300
atcactgaga acaacaacag tgtcaggaa gttgatacac gaatggtgtt gccgctcgtg    3360
tacacttcct cccctgcgat acatgggaga agacggctgc tggtatggca tggaaattag    3420
acccattaat gagaaagaag agaacatggt aaagtcttta gtctcagcag ggagtggaaa    3480
ggtggataac ttcacaatgg gtgtcttgtg tttggcaatc cttttgaag aggtgatgag    3540 aggaaaattt gggaaaaagc acatgattgc aggggttctc ttcacgtttg tactccttct    3600
ctcagggcaa ataacatgga gagacatggc gcacacactc ataatgattg gtccaacgc    3660 ctctgacaga atgggaatgg gcgtcactta cctagcattg attgcaacat ttaaaattca    3720
gccatttttg gctttgggat tcttcctgag gaaactgaca tctagagaaa atttattgtt    3780
gggagttggg ttggccatgg caacaacgtt acaactgcca gaggacattg aacaaatggc    3840
gaatggaata gctttagggc tcatggctct taaattaata acacaatttg aaacatacca    3900 actatgacg gcattagtct ccctaatgtg ttcaaataca atttcacgt tgactgttgc    3960 ctggagaaca gccaccctga ttttggccgg aatttctctt ttgccagtgt gccagtcttc    4020
gagcatgagg aaaacagatt ggctcccaat ggctgtggca gctatgggag ttccaccct    4080 accactttt attttcagtt tgaaagatac gctcaaaagg agaagctggc cactgaatga    4140
gggggtgatg gctgttggac ttgtgagtat tctagctagt tctctcctta ggaatgacgt    4200
gcccatggct ggaccattag tggctggggg cttgctgata gcgtgctacg tcataactgg    4260
cacgtcagca gacctcactg tagaaaaagc agcagatgtg acatgggagg aagaggctga    4320
gcaaacagga gtgtcccaca atttaatgat cacagttgat gacgatgaa caatgagaat    4380 aaaagatgat gagactgaga acatcttaac agtgcttttg aaaacagcat tactaatagt    4440
gtcaggcatt tttccatact ccataccgc aacactgttg gtctggcaca cttggcaaaa    4500
gcaaacccaa agatccggtg tcctatggga cgttcccagc cccccagaga cacagaaagc    4560
agaactggaa gaggggttt ataggatcaa gcagcaagga atttttggga aacccaagt    4620 gggggttgga gtacaaaaag aaggagtttt ccacaccatg tggcacgtca agaggagc    4680 agtgttgaca cacaatggga aaagactgga accaaactgg gctagcgtga aaaagatct    4740 gatttcatac ggaggaggat ggaaattgag tgcacaatgg caaaaggag aggaggtgca    4800 ggttattgcc gtagagcctg ggaagaaccc aaagaacttt caaaccatgc caggcatttt    4860
ccagacaaca cagggggaga taggagcgat tgcactggac ttcaagcctg gaacttcagg    4920
atctcccatc ataaacagag agggaaggt actgggattg tatggcaatg gagtggtcac    4980
aaagaatggt ggctatgtca gtggaatagc acaaacaaat gcagaaccag acggaccgac    5040
accagagttg gaagaagaga tgttcaaaaa gcgaaatcta accataatgg atctccatcc    5100
```

```
cgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca cagggagaga    5280
gattgttgat ctaatgtgcc acgcaacgtt cacaatgcgt ttgctgtcac cagtcagggt    5340
tccaaactac aacttgataa taatggatga ggctcatttc acagacccag ccagtatagc    5400
ggctagaggg tacatatcaa ctcgtgtagg aatgggagag gcagccgcaa ttttcatgac    5460
agccacaccc cctggaacag ctgatgcctt tcctcagagc aacgctccaa ttcaagatga    5520
agaaagagac ataccagaac gctcatggaa ttcaggcaat gaatggatta ccgactttgc    5580
cgggaagacg gtgtggtttg tccctagcat caaagctgga aatgacatag caaactgctt    5640
gcggaaaaat ggaaaaaagg tcattcaact tagtaggaag acttttgaca cagaatatca    5700
aaagactaaa ctaaatgatt gggactttgt ggtgacaaca gacatttcag aaatgggagc    5760
caatttcaaa gcagacagag tgatcgaccc aagaagatgt ctcaagccag tgattttgac    5820
agacggaccc gagcgcgtga tcctggcggg accaatgcca gtcaccgtag cgagcgctgc    5880
gcaaaggaga gggagagttg gcaggaaccc acaaaaagaa aatgaccaat acatattcat    5940
gggccagccc ctcaataatg atgaagacca tgctcactgg acagaagcaa aaatgctgct    6000
agacaacatc aacacaccag aagggatcat accagctctc tttgaaccag aaagggagaa    6060
gtcagccgcc atagacggcg aataccgcct gaagggtgag tccaggaaga ccttcgtgga    6120
actcatgagg aggggtgacc tcccagtttg gctagcccat aaagtagcat cagaagggat    6180
caaatataca gatagaaagt ggtgttttga tggagaacgc aacaatcaaa ttttagagga    6240
gaatatggat gtggaaatct ggacaaagga aggagaaaag aaaaaattga gacctaggtg    6300
gcttgatgcc cgcacttatt cagatccctt agcgctcaag gaattcaagg actttgcggc    6360
tggtagaaag tcaattgccc ttgatcttgt gacagaaata ggaagagtgc cttcacactt    6420
agctcacaga acgagaaacg ccctggacaa tctggtgatg ttgcacacgt cagaacatgg    6480
cgggagggcc tacaggcatg cagtggagga actaccagaa acaatggaaa cactcttact    6540
cctgggactc atgatcctgt taacaggtgg agcaatgctt ttcttgatat caggtaaagg    6600
gattggaaag acttcaatag gactcatttg tgtagctgct tccagcggta tgttatggat    6660
ggctgatgtc ccactccaat ggatcgcgtc tgccatagtc ctggagtttt ttatgatggt    6720
gttacttata ccagaaccag aaaagcagag aactccccaa gacaatcaac tcgcatatgt    6780
cgtgataggc atactcacac tggctgcaat agtagcagcc aatgaaatgg gactgttgga    6840
aaccacaaag agagatttag gaatgtccaa agaaccaggt gttgtttctc caaccagcta    6900
tttggatgtg gacttgcacc cagcatcagc ctggacattg tacgctgtgg ccacaacagt    6960
aataacacca atgttgagac ataccataga gaattccaca gcaaatgtgt ccctggcagc    7020
tatagccaac caggcagtgg tcctgatggg tttagacaaa ggatggccga tatcgaaaat    7080
ggacttaggc gtgccactat ggcactgggt tgttattca caagtgaacc cactaactct    7140
cacagcggca gttctcctgc tagtcacgca ttatgctatt ataggtccag gattgcaggc    7200
aaaagccact cgtgaagctc aaaaaaggac agctgctgga ataatgaaga atcccacggt    7260
ggatgggata atgacaatag acctagatcc tgtaatatac gattcaaaat ttgaaaagca    7320
actaggacag ttatgctcc tggttctgtg tgcagttcaa cttttgttaa tgagaacatc    7380
atgggctttt gtgaagctc taaccctagc cacaggacca ataacaacac tctgggaagg    7440
atcacctggg aagttctgga acaccacgat agctgttttcc atggcgaaca tctttagagg    7500
```

```
gagctattta gcaggagctg ggcttgcttt ttctatcatg aaatcagttg aacaggaaa    7560 gagagggaca gggtcacagg gtgaaacctt gggagaaaag tggaaaaaga aattgaatca    7620
attaccccgg aaagagtttg acctttacaa gaaatccgga atcactgaag tggatagaac    7680
agaagccaaa gaagggttga aaagaggaga ataacacac catgccgtgt ccagaggcag    7740
cgcaaaactt caatggttcg tggagagaaa catggtcatc cccgaaggaa gagtcataga    7800
cttaggctgt ggaagaggag gctggtcata ttattgtgca ggactgaaaa aagttacaga    7860
agtgcgagga tacacaaaag gcggcccagg acatgaagaa acattggaga atcttcacca    7920
agcccaacag tggaagaaag cagaaccata agagtcttga agatggttga accatggcta    7980
aaaaataacc agttttgcat taaagtattg aaccctaca tgccaactgt gattgagcac    8040
ctagaaagac tacaaaggaa acatggagga atgcttgtga gaaatccact ctcacgaaac    8100
tccacgcacg aaatgtactg gatatctaat ggcacaggca atatcgtttc ttcagtcaac    8160
atggtatcca gattgctact taacagattc acaatgacac ataggagacc caccatagag    8220
aaagatgtgg atttaggagc ggggacccga catgtcaatg cggaaccaga aacacccaac    8280
atggatgtca ttggggaaag aataagaagg atcaaggagg agcatagttc aacatggcac    8340
tatgatgatg aaaatcctta taaaacgtgg gcttaccatg gatcctatga agttaaggcc    8400
acaggctcag cctcctccat gataaatgga gtcgtgaaac tcctcacgaa accatgggat    8460
gtggtgccca tggtgacaca gatggcaatg acggatacaa ccccattcgg ccagcaaagg    8520 gttttaaag agaagtggga caccaggaca cccagaccta tgccaggaac aagaaaggtt    8580
atggagatca cagcggaatg gctttggaga accctgggaa ggaacaaaag acccagatta    8640
tgtacgagag aggagttcac aaaaaaggtc agaaccaacg cagctatggg cgccgttttt    8700
acagaggaga ccaatgggca cagtgctaga gctgctgttg aggatgaaga attctggaaa    8760
ctcgtggaca gagaacgtga actccacaaa ttgggcaagt gtggaagctg cgtttacaac    8820
atgatgggca agagagagaa gaaacttgga gagtttggca aagcaaaagg cagtagagcc    8880
atatggtaca tgtggttggg agccagatac cttgagttcg aagcactcgg attcttaaat    8940
gaagaccatt ggttctcgcg tgaaaactct tacagtggag tagaaggaga aggactgcac    9000
aagctgggat acatcttaag agacatttcc aagatacccg gaggagctat gtatgctgat    9060
gacacagctg gttgggacac aagaataaca gaagatgacc tgcacaatga ggaaaaaatc    9120
acacagcaaa tggacctga acacaggcag ttagcaaacg ctatattcaa gctcacatac    9180
caaaacaaag tggtcaaagt tcaacgacca actccaaagg gcacggtaat ggacatcata    9240
tctaggaaag accaaagagg cagtggacag gtgggaactt atggtctgaa tacattcacc    9300
aacatggaag cccagttaat cagacaaatg gaaggagaag gtgtgttgtc gaaggcagac    9360
ctcgagaacc ctcatctgct agagaagaaa gttacacaat ggttggaaac aaaaggagtg    9420
gagaggttaa aaagaatggc catcagcggg gatgattgcg tggtgaaacc aattgatgac    9480
aggttcgcca atgccctgct tgccctgaat gacatgggaa agttaggaa ggacatacct    9540 caatggcagc catcaaggg atggcatgat tggcaacagg tccctttctg ctcccaccac    9600
tttcatgaat tgatcatgaa agatggaaga aagttggtag ttccctgcag acctcaggat    9660
gaattaatcg ggagagcgag aatctctcaa ggagcaggat ggagccttag agaaactgca    9720
tgcctaggga aagcctacgc ccaaatgtgg actctcatgt actttcacag aagagatctt    9780
agactagcat ccaacgccat atgttcagca gtaccagtcc attgggtccc cacaagcaga    9840
```

-continued

```
acgacgtggt ctattcatgc tcaccatcag tggatgacta cagaagacat gcttactgtt   9900
tggaacaggg tgtggataga ggataatcca tggatggaag acaaaactcc agtcaaaacc   9960
tgggaagatg ttccatatct agggaagaga gaagaccaat ggtgcggatc actcattggt  10020
ctcacttcca gagcaacctg ggcccagaac atacttacgg caatccaaca ggtgagaagc  10080
cttataggca atgaagagtt tctggactac atgccttcga tgaagagatt caggaaggag  10140
gaggagtcag agggagccat ttggtaaacg taggaagtga aaagaggca aactgtcagg   10200 ccaccttaag ccacagtacg gaagaagctg tgcagcctgt gagccccgtc caaggacgtt  10260
aaaagaagaa gtcaggccca aaagccacgg tttgagcaaa ccgtgctgcc tgtggctccg  10320
tcgtggggac gtaaaacctg ggaggctgca aactgtggaa gctgtacgca cggtgtagca  10380
gactagcggt tagaggagac ccctcccatg acacaacgca gcagcggggc ccgagctctg  10440
agggaagctg tacctccttg caaggacta gaggttagag gagaccccc gcaaataaaa    10500 acagcatatt gacgctggga gagaccagag atcctgctgt ctcctcagca tcattccagg  10560
cacagaacgc cagaaaatgg aatggtgctg ttgaatcaac aggttctggt accgtaggc   10620 atcgtggtgt cacgctcgtc gtttggtatg gcttcattca gctccggttc ccaacgatca  10680
aggcgagtta catgatcccc catgttgtgc aaaaaagcgg ttagctcctt cggtcctccg  10740
atcgttgtca gaagtaagtt ggccgcagtg ttatcactca tggttatggc agcactgcat  10800
aattctctta ctgtcatgcc atccgtaaga tgcttttctg tgactggtga gtactcaacc  10860
aagtcattct gagaatagtg tatgcggcga ccgagttgct cttgcccggc gtcaacacgg  10920
gataataccg cgccacatag cagaacttta aaagtgctca tcattggaaa acgttcttcg  10980
gggcgaaaac tctcaaggat cttaccgctg ttgagatcca gttcgatgta acccactcgt  11040
gcacccaact gatcttcagc atcttttact ttcaccagcg tttctgggtg agcaaaaaca  11100
ggaaggcaaa atgccgcaaa aaagggaata agggcgacac ggaaatgttg aatactcata  11160
ctcttccttt ttcaatatta ttgaagcatt tatcagggtt attgtctcat gagcggatac  11220
atatttgaat gtatttagaa aaataaacaa ataggggttc cgcgcacatt tccccgaaaa  11280
gtgccacctg acgtctaaga aaccattatt atcatgacat taacctataa aaataggcgt  11340
atcacgaggc cctttcgtct tcaagaattc tcatgtttga cagcttatca tcgataagct  11400
ttaatgcggt agtttatcac agttaaattg ctaacgcagt caggcaccgt gtatgaaatc  11460
taacaatgcg ctcatcgtca tcctcggcac cgtcaccctg gatgctgtag catagggctt  11520
ggttatgccg gtactgccgg gcctcttgcg ggatatcgtc cattccgaca gcatcgccag  11580
tcactatggc gtgctgctgg cgctatatgc gttgatgcaa tttctatgcg cacccgttct  11640
cggagcactg tccgaccgct ttggccgccg cccagtcctg ctcgcttcgc tacttggagc  11700
cactatcgac tacgcgatca tggcgaccac acccgtcctg tggatcctct acgccggacg  11760
catcgtggcc ggcatcaccg cgccacagg tgcggttgct ggcgcctata tcgccgacat   11820
caccgatggg gaagatcggg ctcgccactt cgggctcatg agcgcttgtt tcggcgtggg  11880
tatggtggca ggccccgtgg ccgggggact gttgggcgcc atctccttgc atgcaccatt  11940
ccttgcggcg gcggtgctca acggcctcaa cctactactg ggctgcttcc taatgcagga  12000
gtcgcataag ggagagcgtc gaccgatgcc cttgagagcc ttcaacccag tcagctcctt  12060
ccggtgggcg cggggcatga ctatcgtcgc cgcacttatg actgtcttct ttatcatgca  12120
actcgtagga caggtgccgg cagcgctctg ggtcattttc ggcgaggacc gctttcgctg  12180
gagcgcgacg atgatcggcc tgtcgcttgc ggtattcgga atcttgcacg ccctcgctca  12240
```

```
agccttcgtc actggtcccg ccaccaaacg tttcggcgag aagcaggcca ttatcgccgg    12300
catggcggcc gacgcgctgg gctacgtctt gctggcgttc gcgacgcgag gctggatggc    12360
cttccccatt atgattcttc tcgcttccgg cggcatcggg atgcccgcgt tgcaggccat    12420
gctgtccagg caggtagatg acgaccatca gggacagctt caaggatcgc tcgcggctct    12480
taccagccta acttcgatca ctggaccgct gatcgtcacg gcgatttatg ccgcctcggc    12540
gagcacatgg aacgggttgg catggattgt aggcgccgcc ctataccttg tctgcctccc    12600
cgcgttgcgt cgcggtgcat ggagccgggc cacctcgacc tgaatggaag ccggcggcac    12660
ctcgctaacg gattcaccac tccaagaatt ggagccaatc aattcttgcg agaactgtg    12720 aatgcgcaaa ccaacccttg gcagaacata tccatcgcgt ccgccatctc cagcagccgc    12780
acgcggcgca tctcgggcag cgttgggtcc tggccacggg tgcgcatgat cgtgctcctg    12840
tcgttgagga cccggctagg ctggcggggt tgccttactg gttagcagaa tgaatcaccg    12900
atacgcgagc gaacgtgaag cgactgctgc tgcaaaacgt ctgcgacctg agcaacaaca    12960
tgaatggtct tcggtttccg tgtttcgtaa agtctggaaa cgcggaagtc agcgccctgc    13020
accattatgt tccggatctg catcgcagga tgctgctggc taccctgtgg aacacctaca    13080
tctgtattaa cgaagcgctg gcattgaccc tgagtgattt ttctctggtc ccgccgcatc    13140
cataccgcca gttgtttacc ctcacaacgt tccagtaacc gggcatgttc atcatcagta    13200
acccgtatcg tgagcatcct ctctcgtttc atcggtatca ttaccccat gaacagaaat     13260 cccccttaca cggaggcatc agtgaccaaa caggaaaaaa ccgcccttaa catggcccgc    13320
tttatcagaa gccagacatt aacgcttctg gagaaactca acgagctgga cgcggatgaa    13380
caggcagaca tctgtgaatc gcttcacgac cacgctgatg agctttaccg cagctgcctc    13440
gcgcgtttcg gtgatgacgg tgaaaacctc tgacacatgc agctcccgga gacggtcaca    13500
gcttgtctgt aagcggatgc cgggagcaga caagcccgtc agggcgcgtc agcgggtgtt    13560
ggcgggtgtc ggggcgcagc catgacccag tcacgtagcg atagcggagt gtatactggc    13620
ttaactatgc ggcatcagag cagattgtac tgagagtgca ccatatgcgg tgtgaaatac    13680
cgcacagatg cgtaaggaga aaataccgca tcaggcgctc ttccgcttcc tcgctcactg    13740
actcgctgcg ctcggtcgtt cggctgcggc gagcggtatc agctcactca aaggcggtaa    13800
tacggttatc cacagaatca ggggataacg caggaaagaa catgtgagca aaaggccagc    13860
aaaaggccag gaaccgtaaa aaggccgcgt tgctggcgtt tttccatagg ctccgccccc    13920
ctgacgagca tcacaaaaat cgacgctcaa gtcagaggtg cgaaacccg acaggactat     13980 aaagatacca ggcgtttccc cctggaagct ccctcgtgcg ctctcctgtt ccgaccctgc    14040
cgcttaccgg atacctgtcc gcctttctcc cttcgggaag cgtggcgctt tctcatagct    14100
cacgctgtag gtatctcagt tcggtgtagg tcgttcgctc caagctgggc tgtgtgcacg    14160
aaccccccgt tcagcccgac cgctgcgcct tatccggtaa ctatcgtctt gagtccaacc    14220
cggtaagaca cgacttatcg ccactggcag cagccactgg taacaggatt agcagagcga    14280
ggtatgtagg cggtgctaca gagttcttga agtggtggcc taactacggc tacactagaa    14340
ggacagtatt tggtatctgc gctctgctga agccagttac cttcggaaaa agagttggta    14400
gctcttgatc cggcaaacaa accaccgctg gtagcggtgg tttttttgtt tgcaagcagc    14460
agattacgcg cagaaaaaaa ggatctcaag aagatccttt gatcttttct acggggtctg    14520
acgctcagtg gaacgaaaac tcacgttaag ggattttggt catgagatta tcaaaaagga    14580
```

```
tcttcaccta gatcctttta aattaaaaat gaagttttaa atcaatctaa agtatatatg    14640
agtaaacttg gtctgacagt taccaatgct taatcagtga ggcacctatc tcagcgatct    14700
gtctatttcg ttcatccata gttgcctgac tccccgtcgt gtagataact acgatacggg    14760
agggcttacc atctggcccc agtgctgcaa tgataccgcg agacccacgc tcaccggctc    14820
cagatttatc agcaataaac cagccagccg gaagggccga gcgcagaagt ggtcctgcaa    14880
ctttatccgc ctccatccag tctattaatt gttgccggga agctagagta agtagttcgc    14940
cagttaatag tttgcgcaac gttgttgcca ttgctgcaag atctggctag cgatgaccct    15000
gctgattggt tcgctgacca tttccgggcg cgccgattta ggtgacacta tag           15053
```

<210> SEQ ID NO 33
<211> LENGTH: 3390
<212> TYPE: PRT
<213> ORGANISM: Dengue 3 (Sleman/78)

<400> SEQUENCE: 33

```
Met Asn Asn Gln Arg Lys Lys Thr Gly Lys Pro Ser Ile Asn Met Leu
  1               5                  10                  15

Lys Arg Val Arg Asn Arg Val Ser Thr Gly Ser Gln Leu Ala Lys Arg
             20                  25                  30

Phe Ser Arg Gly Leu Leu Asn Gly Gln Gly Pro Met Lys Leu Val Met
         35                  40                  45

Ala Phe Ile Ala Phe Leu Arg Phe Leu Ala Ile Pro Pro Thr Ala Gly
     50                  55                  60

Val Leu Ala Arg Trp Gly Thr Phe Lys Lys Ser Gly Ala Ile Lys Val
 65                  70                  75                  80

Leu Arg Gly Phe Lys Lys Glu Ile Ser Asn Met Leu Ser Ile Ile Asn
                 85                  90                  95

Arg Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro Leu Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Lys Val Glu Thr Trp
225                 230                 235                 240

Ala Phe Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
```

```
                    290                 295                 300
Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                    325                 330                 335

Arg Lys Leu Cys Ile Glu Gly Lys Ile Thr Asn Val Thr Thr Asp Ser
                340                 345                 350

Arg Cys Pro Thr Gln Gly Glu Ala Ile Leu Pro Glu Glu Gln Asp Gln
                355                 360                 365

Asn His Val Cys Lys His Thr Tyr Val Asp Arg Gly Trp Gly Asn Gly
                370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
                420                 425                 430

Asn Glu Thr Gln Gly Val Thr Ala Glu Ile Thr Pro Gln Ala Ser Thr
                435                 440                 445

Val Glu Ala Ile Leu Pro Glu Tyr Gly Thr Leu Gly Leu Glu Cys Ser
450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Thr Glu Thr Pro Thr Trp Asn Lys Lys
                500                 505                 510

Glu Leu Leu Val Thr Phe Lys Asn Ala His Ala Lys Lys Gln Glu Val
                515                 520                 525

Val Val Leu Gly Ser Gln Glu Gly Ala Met His Thr Ala Leu Thr Gly
530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Asn Ala Phe Val Leu Lys Lys Glu Val Ser Glu
                580                 585                 590

Thr Gln His Gly Thr Ile Leu Ile Lys Val Glu Tyr Lys Gly Glu Asp
                595                 600                 605

Ala Pro Cys Lys Ile Pro Phe Ser Thr Glu Asp Gly Gln Gly Lys Ala
610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
                660                 665                 670

Gly Ser Ser Ile Gly Lys Met Phe Glu Ala Thr Ala Arg Gly Ala Arg
                675                 680                 685

Arg Met Ala Ile Leu Gly Asp Thr Ala Trp Asp Phe Gly Ser Val Gly
                690                 695                 700

Gly Val Leu Asn Ser Leu Gly Lys Met Val His Gln Ile Phe Gly Ser
705                 710                 715                 720
```

-continued

```
Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Val Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Ile Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Asn
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Met Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Leu Ile Glu
            980                 985                 990

Val Lys Thr Cys Thr Trp Pro Lys Ser His Thr Leu Trp Ser Asn Gly
        995                 1000                1005

Val Leu Glu Ser Asp Met Ile Ile Pro Lys Ser Leu Ala Gly Pro Ile
    1010                1015                1020

Ser Gln His Asn Tyr Arg Pro Gly Tyr His Thr Gln Thr Ala Gly Pro
1025                1030                1035                1040

Trp His Leu Gly Lys Leu Glu Leu Asp Phe Asn Tyr Cys Glu Gly Thr
                1045                1050                1055

Thr Val Val Ile Thr Glu Asn Cys Gly Thr Arg Gly Pro Ser Leu Arg
            1060                1065                1070

Thr Thr Thr Val Ser Gly Lys Leu Ile His Glu Trp Cys Cys Arg Ser
        1075                1080                1085

Cys Thr Leu Pro Pro Leu Arg Tyr Met Gly Glu Asp Gly Cys Trp Tyr
    1090                1095                1100

Gly Met Glu Ile Arg Pro Ile Asn Glu Lys Glu Glu Asn Met Val Lys
1105                1110                1115                1120

Ser Leu Val Ser Ala Gly Ser Gly Lys Val Asp Asn Phe Thr Met Gly
                1125                1130                1135
```

-continued

Val Leu Cys Leu Ala Ile Leu Phe Glu Val Met Arg Gly Lys Phe
              1140                1145                1150

Gly Lys Lys His Met Ile Ala Gly Val Leu Phe Thr Phe Val Leu Leu
        1155                1160                1165

Leu Ser Gly Gln Ile Thr Trp Arg Asp Met Ala His Thr Leu Ile Met
        1170                1175                1180

Ile Gly Ser Asn Ala Ser Asp Arg Met Gly Met Gly Val Thr Tyr Leu
1185                1190                1195                1200

Ala Leu Ile Ala Thr Phe Lys Ile Gln Pro Phe Leu Ala Leu Gly Phe
              1205                1210                1215

Phe Leu Arg Lys Leu Thr Ser Arg Glu Asn Leu Leu Gly Val Gly
              1220                1225                1230

Leu Ala Met Ala Thr Thr Leu Gln Leu Pro Glu Asp Ile Glu Gln Met
              1235                1240                1245

Ala Asn Gly Ile Ala Leu Gly Leu Met Ala Leu Lys Leu Ile Thr Gln
              1250                1255                1260

Phe Glu Thr Tyr Gln Leu Trp Thr Ala Leu Val Ser Leu Met Cys Ser
1265                1270                1275                1280

Asn Thr Ile Phe Thr Leu Thr Val Ala Trp Arg Thr Ala Thr Leu Ile
              1285                1290                1295

Leu Ala Gly Ile Ser Leu Leu Pro Val Cys Gln Ser Ser Met Arg
              1300                1305                1310

Lys Thr Asp Trp Leu Pro Met Ala Val Ala Ala Met Gly Val Pro Pro
              1315                1320                1325

Leu Pro Leu Phe Ile Phe Ser Leu Lys Asp Thr Leu Lys Arg Arg Ser
              1330                1335                1340

Trp Pro Leu Asn Glu Gly Val Met Ala Val Gly Leu Val Ser Ile Leu
1345                1350                1355                1360

Ala Ser Ser Leu Leu Arg Asn Asp Val Pro Met Ala Gly Pro Leu Val
              1365                1370                1375

Ala Gly Gly Leu Leu Ile Ala Cys Tyr Val Ile Thr Gly Thr Ser Ala
              1380                1385                1390

Asp Leu Thr Val Glu Lys Ala Ala Asp Val Thr Trp Glu Glu Glu Ala
              1395                1400                1405

Glu Gln Thr Gly Val Ser His Asn Leu Met Ile Thr Val Asp Asp Asp
              1410                1415                1420

Gly Thr Met Arg Ile Lys Asp Asp Glu Thr Glu Asn Ile Leu Thr Val
1425                1430                1435                1440

Leu Leu Lys Thr Ala Leu Leu Ile Val Ser Gly Ile Phe Pro Tyr Ser
              1445                1450                1455

Ile Pro Ala Thr Leu Leu Val Trp His Thr Trp Gln Lys Gln Thr Gln
              1460                1465                1470

Arg Ser Gly Val Leu Trp Asp Val Pro Ser Pro Glu Thr Gln Lys
              1475                1480                1485

Ala Glu Leu Glu Glu Gly Val Tyr Arg Ile Lys Gln Gln Gly Ile Phe
              1490                1495                1500

Gly Lys Thr Gln Val Gly Val Gly Val Gln Lys Glu Gly Val Phe His
1505                1510                1515                1520

Thr Met Trp His Val Thr Arg Gly Ala Val Leu Thr His Asn Gly Lys
              1525                1530                1535

Arg Leu Glu Pro Asn Trp Ala Ser Val Lys Lys Asp Leu Ile Ser Tyr
              1540                1545                1550

Gly Gly Gly Trp Lys Leu Ser Ala Gln Trp Gln Lys Gly Glu Glu Val

-continued

```
            1555                1560                1565

Gln Val Ile Ala Val Glu Pro Gly Lys Asn Pro Lys Asn Phe Gln Thr
        1570                1575                1580

Met Pro Gly Ile Phe Gln Thr Thr Thr Gly Glu Ile Gly Ala Ile Ala
1585                1590                1595                1600

Leu Asp Phe Lys Pro Gly Thr Ser Gly Ser Pro Ile Ile Asn Arg Glu
                1605                1610                1615

Gly Lys Val Leu Gly Leu Tyr Gly Asn Gly Val Val Thr Lys Asn Gly
            1620                1625                1630

Gly Tyr Val Ser Gly Ile Ala Gln Thr Asn Ala Glu Pro Asp Gly Pro
            1635                1640                1645

Thr Pro Glu Leu Glu Glu Met Phe Lys Lys Arg Asn Leu Thr Ile
        1650                1655                1660

Met Asp Leu His Pro Gly Ser Gly Lys Thr Arg Lys Tyr Leu Pro Ala
1665                1670                1675                1680

Ile Val Arg Glu Ala Ile Lys Arg Arg Leu Arg Thr Leu Ile Leu Ala
                1685                1690                1695

Pro Thr Arg Val Val Ala Ala Glu Met Glu Glu Ala Leu Lys Gly Leu
            1700                1705                1710

Pro Ile Arg Tyr Gln Thr Thr Ala Thr Lys Ser Glu His Thr Gly Arg
            1715                1720                1725

Glu Ile Val Asp Leu Met Cys His Ala Thr Phe Thr Met Arg Leu Leu
        1730                1735                1740

Ser Pro Val Arg Val Pro Asn Tyr Asn Leu Ile Ile Met Asp Glu Ala
1745                1750                1755                1760

His Phe Thr Asp Pro Ala Ser Ile Ala Ala Arg Gly Tyr Ile Ser Thr
                1765                1770                1775

Arg Val Gly Met Gly Glu Ala Ala Ala Ile Phe Met Thr Ala Thr Pro
            1780                1785                1790

Pro Gly Thr Ala Asp Ala Phe Pro Gln Ser Asn Ala Pro Ile Gln Asp
            1795                1800                1805

Glu Glu Arg Asp Ile Pro Glu Arg Ser Trp Asn Ser Gly Asn Glu Trp
        1810                1815                1820

Ile Thr Asp Phe Ala Gly Lys Thr Val Trp Phe Val Pro Ser Ile Lys
1825                1830                1835                1840

Ala Gly Asn Asp Ile Ala Asn Cys Leu Arg Lys Asn Gly Lys Lys Val
                1845                1850                1855

Ile Gln Leu Ser Arg Lys Thr Phe Asp Thr Glu Tyr Gln Lys Thr Lys
            1860                1865                1870

Leu Asn Asp Trp Asp Phe Val Val Thr Thr Asp Ile Ser Glu Met Gly
        1875                1880                1885

Ala Asn Phe Lys Ala Asp Arg Val Ile Asp Pro Arg Arg Cys Leu Lys
        1890                1895                1900

Pro Val Ile Leu Thr Asp Gly Pro Glu Arg Val Ile Leu Ala Gly Pro
1905                1910                1915                1920

Met Pro Val Thr Val Ala Ser Ala Ala Gln Arg Arg Gly Arg Val Gly
                1925                1930                1935

Arg Asn Pro Gln Lys Glu Asn Asp Gln Tyr Ile Phe Met Gly Gln Pro
            1940                1945                1950

Leu Asn Asn Asp Glu Asp His Ala His Trp Thr Glu Ala Lys Met Leu
        1955                1960                1965

Leu Asp Asn Ile Asn Thr Pro Glu Gly Ile Ile Pro Ala Leu Phe Glu
        1970                1975                1980
```

```
Pro Glu Arg Glu Lys Ser Ala Ile Asp Gly Glu Tyr Arg Leu Lys
1985                1990                1995                2000

Gly Glu Ser Arg Lys Thr Phe Val Glu Leu Met Arg Gly Asp Leu
            2005                2010                2015

Pro Val Trp Leu Ala His Lys Val Ala Ser Glu Gly Ile Lys Tyr Thr
        2020                2025                2030

Asp Arg Lys Trp Cys Phe Asp Gly Arg Asn Asn Gln Ile Leu Glu
            2035                2040                2045

Glu Asn Met Asp Val Glu Ile Trp Thr Lys Glu Gly Glu Lys Lys Lys
        2050                2055                2060

Leu Arg Pro Arg Trp Leu Asp Ala Arg Thr Tyr Ser Asp Pro Leu Ala
2065                2070                2075                2080

Leu Lys Glu Phe Lys Asp Phe Ala Ala Gly Arg Lys Ser Ile Ala Leu
            2085                2090                2095

Asp Leu Val Thr Glu Ile Gly Arg Val Pro Ser His Leu Ala His Arg
                2100                2105                2110

Thr Arg Asn Ala Leu Asp Asn Leu Val Met Leu His Thr Ser Glu His
                2115                2120                2125

Gly Gly Arg Ala Tyr Arg His Ala Val Glu Glu Leu Pro Glu Thr Met
    2130                2135                2140

Glu Thr Leu Leu Leu Leu Gly Leu Met Ile Leu Leu Thr Gly Gly Ala
2145                2150                2155                2160

Met Leu Phe Leu Ile Ser Gly Lys Gly Ile Gly Lys Thr Ser Ile Gly
                2165                2170                2175

Leu Ile Cys Val Ala Ala Ser Ser Gly Met Leu Trp Met Ala Asp Val
                2180                2185                2190

Pro Leu Gln Trp Ile Ala Ser Ala Ile Val Leu Glu Phe Phe Met Met
        2195                2200                2205

Val Leu Leu Ile Pro Glu Pro Glu Lys Gln Arg Thr Pro Gln Asp Asn
    2210                2215                2220

Gln Leu Ala Tyr Val Val Ile Gly Ile Leu Thr Leu Ala Ala Ile Val
2225                2230                2235                2240

Ala Ala Asn Glu Met Gly Leu Leu Glu Thr Thr Lys Arg Asp Leu Gly
                2245                2250                2255

Met Ser Lys Glu Pro Gly Val Val Ser Pro Thr Ser Tyr Leu Asp Val
            2260                2265                2270

Asp Leu His Pro Ala Ser Ala Trp Thr Leu Tyr Ala Val Ala Thr Thr
        2275                2280                2285

Val Ile Thr Pro Met Leu Arg His Thr Ile Glu Asn Ser Thr Ala Asn
    2290                2295                2300

Val Ser Leu Ala Ala Ile Ala Asn Gln Ala Val Val Leu Met Gly Leu
2305                2310                2315                2320

Asp Lys Gly Trp Pro Ile Ser Lys Met Asp Leu Gly Val Pro Leu Leu
            2325                2330                2335

Ala Leu Gly Cys Tyr Ser Gln Val Asn Pro Leu Thr Leu Thr Ala Ala
        2340                2345                2350

Val Leu Leu Leu Val Thr His Tyr Ala Ile Ile Gly Pro Gly Leu Gln
        2355                2360                2365

Ala Lys Ala Thr Arg Glu Ala Gln Lys Arg Thr Ala Ala Gly Ile Met
    2370                2375                2380

Lys Asn Pro Thr Val Asp Gly Ile Met Thr Ile Asp Leu Asp Pro Val
2385                2390                2395                2400
```

Ile Tyr Asp Ser Lys Phe Glu Lys Gln Leu Gly Gln Val Met Leu Leu
             2405                2410                2415

Val Leu Cys Ala Val Gln Leu Leu Met Arg Thr Ser Trp Ala Phe
2420                2425                2430

Cys Glu Ala Leu Thr Leu Ala Thr Gly Pro Ile Thr Thr Leu Trp Glu
             2435                2440                2445

Gly Ser Pro Gly Lys Phe Trp Asn Thr Thr Ile Ala Val Ser Met Ala
             2450                2455                2460

Asn Ile Phe Arg Gly Ser Tyr Leu Ala Gly Ala Gly Leu Ala Phe Ser
2465                2470                2475                2480

Ile Met Lys Ser Val Gly Thr Gly Lys Arg Gly Thr Gly Ser Gln Gly
             2485                2490                2495

Glu Thr Leu Gly Glu Lys Trp Lys Lys Leu Asn Gln Leu Pro Arg
             2500                2505                2510

Lys Glu Phe Asp Leu Tyr Lys Lys Ser Gly Ile Thr Glu Val Asp Arg
             2515                2520                2525

Thr Glu Ala Lys Glu Gly Leu Lys Arg Gly Glu Ile Thr His His Ala
             2530                2535                2540

Val Ser Arg Gly Ser Ala Lys Leu Gln Trp Phe Val Glu Arg Asn Met
2545                2550                2555                2560

Val Ile Pro Glu Gly Arg Val Ile Asp Leu Gly Cys Gly Arg Gly Gly
             2565                2570                2575

Trp Ser Tyr Tyr Cys Ala Gly Leu Lys Lys Val Thr Glu Val Arg Gly
             2580                2585                2590

Tyr Thr Lys Gly Gly Pro Gly His Glu Glu Pro Val Pro Met Ser Thr
             2595                2600                2605

Tyr Gly Trp Asn Ile Val Lys Leu Met Ser Gly Lys Asp Val Phe Tyr
             2610                2615                2620

Leu Pro Pro Glu Lys Cys Asp Thr Leu Leu Cys Asp Ile Gly Glu Ser
2625                2630                2635                2640

Ser Pro Ser Pro Thr Val Glu Glu Ser Arg Thr Ile Arg Val Leu Lys
             2645                2650                2655

Met Val Glu Pro Trp Leu Lys Asn Asn Gln Phe Cys Ile Lys Val Leu
             2660                2665                2670

Asn Pro Tyr Met Pro Thr Val Ile Glu His Leu Glu Arg Leu Gln Arg
             2675                2680                2685

Lys His Gly Gly Met Leu Val Arg Asn Pro Leu Ser Arg Asn Ser Thr
             2690                2695                2700

His Glu Met Tyr Trp Ile Ser Asn Gly Thr Gly Asn Ile Val Ser Ser
2705                2710                2715                2720

Val Asn Met Val Ser Arg Leu Leu Leu Asn Arg Phe Thr Met Thr His
             2725                2730                2735

Arg Arg Pro Thr Ile Glu Lys Asp Val Asp Leu Gly Ala Gly Thr Arg
             2740                2745                2750

His Val Asn Ala Glu Pro Glu Thr Pro Asn Met Asp Val Ile Gly Glu
             2755                2760                2765

Arg Ile Arg Arg Ile Lys Glu Glu His Ser Ser Thr Trp His Tyr Asp
             2770                2775                2780

Asp Glu Asn Pro Tyr Lys Thr Trp Ala Tyr His Gly Ser Tyr Glu Val
2785                2790                2795                2800

Lys Ala Thr Gly Ser Ala Ser Ser Met Ile Asn Gly Val Val Lys Leu
             2805                2810                2815

Leu Thr Lys Pro Trp Asp Val Val Pro Met Val Thr Gln Met Ala Met

```
               2820                2825                2830
Thr Asp Thr Thr Pro Phe Gly Gln Gln Arg Val Phe Lys Glu Lys Val
        2835                2840                2845

Asp Thr Arg Thr Pro Arg Pro Met Pro Gly Thr Arg Lys Val Met Glu
    2850                2855                2860

Ile Thr Ala Glu Trp Leu Trp Arg Thr Leu Gly Arg Asn Lys Arg Pro
2865                2870                2875                2880

Arg Leu Cys Thr Arg Glu Glu Phe Thr Lys Lys Val Arg Thr Asn Ala
            2885                2890                2895

Ala Met Gly Ala Val Phe Thr Glu Glu Asn Gln Trp Asp Ser Ala Arg
        2900                2905                2910

Ala Ala Val Glu Asp Glu Glu Phe Trp Lys Leu Val Asp Arg Glu Arg
    2915                2920                2925

Glu Leu His Lys Leu Gly Lys Cys Gly Ser Cys Val Tyr Asn Met Met
        2930                2935                2940

Gly Lys Arg Glu Lys Lys Leu Gly Glu Phe Gly Lys Ala Lys Gly Ser
2945                2950                2955                2960

Arg Ala Ile Trp Tyr Met Trp Leu Gly Ala Arg Tyr Leu Glu Phe Glu
            2965                2970                2975

Ala Leu Gly Phe Leu Asn Glu Asp His Trp Phe Ser Arg Glu Asn Ser
        2980                2985                2990

Tyr Ser Gly Val Glu Gly Glu Gly Leu His Lys Leu Gly Tyr Ile Leu
    2995                3000                3005

Arg Asp Ile Ser Lys Ile Pro Gly Gly Ala Met Tyr Ala Asp Asp Thr
        3010                3015                3020

Ala Gly Trp Asp Thr Arg Ile Thr Glu Asp Asp Leu His Asn Glu Glu
3025                3030                3035                3040

Lys Ile Thr Gln Gln Met Asp Pro Glu His Arg Gln Leu Ala Asn Ala
            3045                3050                3055

Ile Phe Lys Leu Thr Tyr Gln Asn Lys Val Val Lys Val Gln Arg Pro
        3060                3065                3070

Thr Pro Lys Gly Thr Val Met Asp Ile Ile Ser Arg Lys Asp Gln Arg
    3075                3080                3085

Gly Ser Gly Gln Val Gly Thr Tyr Gly Leu Asn Thr Phe Thr Asn Met
        3090                3095                3100

Glu Ala Gln Leu Ile Arg Gln Met Glu Gly Glu Gly Val Leu Ser Lys
3105                3110                3115                3120

Ala Asp Leu Glu Asn Pro His Leu Leu Glu Lys Lys Val Thr Gln Trp
            3125                3130                3135

Leu Glu Thr Lys Gly Val Glu Arg Leu Lys Arg Met Ala Ile Ser Gly
        3140                3145                3150

Asp Asp Cys Val Val Lys Pro Ile Asp Asp Arg Phe Ala Asn Ala Leu
        3155                3160                3165

Leu Ala Leu Asn Asp Met Gly Lys Val Arg Lys Asp Ile Pro Gln Trp
        3170                3175                3180

Gln Pro Ser Lys Gly Trp His Asp Trp Gln Gln Val Pro Phe Cys Ser
3185                3190                3195                3200

His His Phe His Glu Leu Ile Met Lys Asp Gly Arg Lys Leu Val Val
            3205                3210                3215

Pro Cys Arg Pro Gln Asp Glu Leu Ile Gly Arg Ala Arg Ile Ser Gln
        3220                3225                3230

Gly Ala Gly Trp Ser Leu Arg Glu Thr Ala Cys Leu Gly Lys Ala Tyr
        3235                3240                3245
```

```
Ala Gln Met Trp Thr Leu Met Tyr Phe His Arg Arg Asp Leu Arg Leu
    3250                3255                3260
Ala Ser Asn Ala Ile Cys Ser Ala Val Pro Val His Trp Val Pro Thr
3265                3270                3275                3280
Ser Arg Thr Thr Trp Ser Ile His Ala His His Gln Trp Met Thr Thr
                3285                3290                3295
Glu Asp Met Leu Thr Val Trp Asn Arg Val Trp Ile Glu Asp Asn Pro
            3300                3305                3310
Trp Met Glu Asp Lys Thr Pro Val Lys Thr Trp Glu Asp Val Pro Tyr
        3315                3320                3325
Leu Gly Lys Arg Glu Asp Gln Trp Cys Gly Ser Leu Ile Gly Leu Thr
    3330                3335                3340
Ser Arg Ala Thr Trp Ala Gln Asn Ile Leu Thr Ala Ile Gln Gln Val
3345                3350                3355                3360
Arg Ser Leu Ile Gly Asn Glu Glu Phe Leu Asp Tyr Met Pro Ser Met
                3365                3370                3375
Lys Arg Phe Arg Lys Glu Glu Glu Ser Glu Gly Ala Ile Trp
            3380                3385                3390

<210> SEQ ID NO 34
<211> LENGTH: 51
<212> TYPE: DNA
<213> ORGANISM: Artificial Sequence
<220> FEATURE:
<223> OTHER INFORMATION: Forward primer

<400> SEQUENCE: 34
tcaaaacaaa agaaaagatc tgcagtgacc ggaattgcag tcatgattgg c           51

<210> SEQ ID NO 35
<211> LENGTH: 51
<212> TYPE: DNA
<213> ORGANISM: Artificial Sequence
<220> FEATURE:
<223> OTHER INFORMATION: Forward primer

<400> SEQUENCE: 35
tcaaaacaaa agaaaagatc tgcagggacc ggaattgcag tcatgattgg c           51

<210> SEQ ID NO 36
<211> LENGTH: 51
<212> TYPE: DNA
<213> ORGANISM: Artificial Sequence
<220> FEATURE:
<223> OTHER INFORMATION: Forward primer

<400> SEQUENCE: 36
tcaaaacaaa agaaaagatc tgcagacacc ggaattgcag tcatgattgg c           51

<210> SEQ ID NO 37
<211> LENGTH: 64
<212> TYPE: DNA
<213> ORGANISM: Artificial Sequence
<220> FEATURE:
<223> OTHER INFORMATION: Reverse primer

<400> SEQUENCE: 37
ccgcaagaaa cgtcatagca attgacctgt cactcgagtt gattcccatc cacaacagaa  60
gagc                                                              64
```

CONSTRUCTION OF WEST NILE VIRUS AND DENGUE VIRUS CHIMERAS FOR USE IN A LIVE VIRUS VACCINE TO PREVENT DISEASE CAUSED BY WEST NILE VIRUS

RELATED APPLICATIONS

This application is a continuation and claims the benefit of priority of International Application No. PCT/US03/00594 filed Jan. 9, 2003, designating the United States of America and published in English on Jul. 24, 2003 as WO 03/059384, which claims the benefit of priority of U.S. Provisional Application No. 60/347,281 filed Jan. 10, 2002, both of which are hereby expressly incorporated by reference in their entireties.

FIELD OF THE INVENTION

The present invention relates to attenuated, immunogenic West Nile virus chimeras built on a dengue virus backbone for the production of immunogenic, live, attenuated West Nile virus vaccines.

BACKGROUND OF THE INVENTION

Beginning with FIG. 1A, the *flavivirus* genome is a single-stranded, positive-sense RNA approximately 11 kb in length, containing a 5' untranslated region (5' UTR); a coding region encoding the three viral structural proteins; seven nonstructural proteins, designated NS1, NS2A, NS2B, NS3, NS4A, NS4B, NS5; and a 3' untranslated region (3' UTR). The viral structural proteins include the capsid (C), premembrane/ membrane (prM) and envelope (E) proteins. The structural and nonstructural proteins are translated as a single polyprotein. The polyprotein is then processed by cellular and viral proteases.

West Nile virus (WN) belongs to the family Flaviviridae that comprises more than 60 viruses, many of which are important human pathogens. WN is a member of the Japanese encephalitis virus (JE) serocomplex of mosquito-borne flaviviruses that includes St. Louis encephalitis, JE, and Murray Valley encephalitis viruses (Calisher, C. H. et al. 1989 *J Gen Virol* 70:27-43; Burke, D. S. & Monath, T. P. 2001 in: *Fields Virology*, eds. Knipe, D. M. & Howley, P. M. Lippincott Williams and Wilkins, Philadelphia, 4-th ed., pp. 1043-1125). Like other members of the JE antigenic complex, WN is maintained in a natural cycle that involves mosquito vectors and birds, while humans and equines are usually incidental hosts. For many years WN has been recognized as one of the most widely distributed flaviviruses with a geographic range including Africa, Australia, Europe, the Middle East and West Asia (Burke, D. S. & Monath, T. P. 2001 in: *Fields Virology*, eds. Knipe, D. M. & Howley, P. M. Lippincott Williams and Wilkins, Philadelphia, 4-th ed., pp. 1043-1125; Hayes, C. G. 1989 in: The *Arboviruses: Epidemiology and Ecology*, ed. Monath T. P. Boca Raton, Fla. CRC Press, Volume V, pp. 59-88). During 1999 WN first established itself in the USA in the Northeast and Mid-Atlantic States and more recently this virus extended its range to include the Southeastern and Western States (Anderson, J. F. et al. 1999 *Science* 286:2331-2333; Lanciotti, R. S. et al. 1999 *Science* 286:2333-2337; Campbell, G. L. et al. 2002 *Lancet* 2:519-529). In endemic regions, most human WN infections are asymptomatic or cause mild illness with symptoms of low-grade fever, headache, body aches, rash, myalgia, and polyarthropathy. However, human epidemics with severe disease have been reported in Israel, France, Romania, and Russia. In acute severe illness, the virus can cause hepatitis, meningitis and encephalitis leading to paralysis, and coma resulting in death. The neuropathologic lesions are similar to those of JE, with diffuse CNS inflammation and neuronal degeneration. Virus is also found in the spleen, liver, lymph nodes, and lungs of infected individuals. During the 1999 outbreak of WN in the USA, more than 60 people became ill and 7 died, while during 2002, morbidity was 3873 cases and there were 246 deaths (CDC Report: West Nile Update Current case Count, Jan. 2, 2003). Because of the recent and unexpected spread of WN from the Northeast to the Southeast and the West of the USA, this virus is considered a significant emerging disease threat that has embedded itself over a considerable region of the country. Currently, a licensed human vaccine is not available for prevention of WN disease. Mosquito control is the only practical strategy to combat the spread of disease, but effective spraying is difficult to perform in urban areas. Clearly, an effective vaccine is needed to protect at-risk populations.

Dengue viruses are mosquito-borne pathogens of the genus *Flavivirus* (family Flaviviridae). Four serotypes of dengue virus (DEN) have been identified, including dengue type 1 virus (DEN1), dengue type 2 virus (DEN2), dengue type 3 virus (DEN3) and dengue type 4 virus (DEN4). Live, attenuated dengue viruses of all four serotypes have been developed at Mahidol University in Thailand by passaging the wild-type viruses in primary dog kidney cell culture (Sabchareon, A. et al. 2002 *Am J Trop Med Hyg* 66:264-272). These are currently the least promising live, attenuated vaccine candidates for immunization against dengue virus infection and/or disease because they are not well characterized as to the relative contributions of attenuation-associated mutations to the actual mechanism of attenuation nor as to the potential for reverse mutations to revert any of the vaccine candidates to the virulent biological phenotype of the wild-type dengue virus. These vaccine candidates have been designated by a combination of their dengue serotype, the cell line through which they were passaged and the number of times they were passaged. Thus, a dengue serotype 1 wild-type virus passaged in primary dog kidney (PDK) cells 13 times is designated as DEN1 PDK13 virus. Other vaccine candidates are DEN2 PDK53, DEN3 PGMK30/FRhL3 (thirty passages in primary green monkey kidney cells, followed by three passages in fetal rhesus lung cells) and DEN4 PDK48. These four candidate vaccine viruses were derived by tissue culture passage of wild-type parental DEN1 16007, DEN2 16681, DEN3 16562 and DEN4 1036 viruses, respectively.

Except for DEN2 PDK53 virus, the number and identity of the genetic mutations that accrued during multiple passages in cell culture and that are associated with the attenuation phenotype of the vaccine candidates are unknown. Neither the relative contributions of such attenuation-associated mutations to the actual mechanism of attenuation, nor the potential for reverse mutations to revert any of the vaccine candidates to the virulent biological phenotype of the wild-type dengue virus are known for any of these four vaccine candidates. An understanding of the characteristics of a vaccine candidate is critical for the prediction of its stability and safety.

Accordingly, there is a need for attenuated, yet immunogenic flaviviruses to be used in the development of *flavivirus* vaccines to confer protection against flaviviruses. What would be ideal is a vaccine that would simultaneously protect an individual against *flavivirus* disease and be sufficiently characterized so that stability and safety are predictable.

SUMMARY OF THE INVENTION

Chimeric flaviviruses that are attenuated and immunogenic are provided. Chimeric viruses containing the nonstructural protein genes of a dengue virus are used as a backbone into which the structural protein genes of a West Nile virus are substituted. These chimeric viruses exhibit pronounced immunogenicity in the absence of the accompanying clinical symptoms of viral disease. The attenuated chimeric viruses are effective as immunogens or vaccines and may be combined in a pharmaceutical composition to confer immunity against West Nile virus.

BRIEF DESCRIPTION OF THE DRAWINGS

FIG. 1B shows a strategy used to replace the genes for prM and E proteins of DEN4 with the corresponding genes of West Nile virus to produce WN/DEN4 chimeras that serve as candidate attenuated vaccine strains.

FIG. 2 shows the structure of portions of chimeric WN/DEN4 cDNAs. The top bar depicts the chimeric virus cDNA genome from the 5' terminus of the genome to the 3' terminus of the NS1 gene. The solid black boxes represent hydrophobic domains in the polyprotein. The vertical solid arrow indicates the position of a potential NS2B-NS3 protease cleavage site in the polyprotein between the C and prM proteins (the first junction in chimeric genome). Cleavage sites for cellular signalase are indicated by open triangles (∇). A restriction enzyme-cleaved WN cDNA fragment bearing the sequence for the WN premembrane (prM) and envelope glycoprotein (E) structural protein genes was inserted into DEN4 cDNA at PstI and XhoI sites, which are underlined. The second junction is located in the COOH-terminus of the WN E protein between the two hydrophobic domains. The amino acid and nucleotide sequences of WN are presented in bold letters, and nucleotide numbering system is from GenBank accession No. AF196835. Infectivity of RNA transcripts from full-length cDNA constructs was tested by transfecting simian Vero or C6/36 mosquito cells and evaluating cell cultures for evidence of infection by immunofluorescence assay. The two clones in group 4 sustained a mutation of the amino acid +6 downstream from the cleavage site from I (isoleucine) to T (threonine) during cloning of cDNA (represented in the figure). Only these two clones were viable, yielding infectious virus following transfection of full length RNA transcripts.

*Indicates amino acids in chimeric constructs that vary at the 3+ position downstream of protease cleavage site. **Not applicable. ⁺Two infectious chimeric WN/DEN4 viruses, namely clone 18 and 55 from group 4, were isolated.

| Table of Sequences from FIG. 2 | | |
| --- | --- | --- |
| SEQUENCE | SEQ ID NO | SOURCE |
| KKRGGRTGIA | 1 | WN |
| AAGAAAAGAGGAGGAAAGACCGGAATTGCA | 2 | WN |
| RKRSTITLLC | 3 | DEN4 |
| AGAAAAAGGTGAACGATAACATTGCTGTGC | 4 | DEN4 |
| RKRSAVTGIA | 5 | WN/DEN4 |
| AGAAAAAGGTCTGCAGTGACCGGAATTGCA | 6 | WN/DEN4 |
| RKRSAGTGIA | 7 | WN/DEN4 |
| AGAAAAAGGTCTGCAGGGACCGGAATTGCA | 8 | WN/DEN4 |
| RKRSADTGIA | 9 | WN/DEN4 |
| AGAAAAAGGTCTGCAGACACCGGAATTGCA | 10 | WN/DEN4 |
| RKRSADTGTA | 11 | WN/DEN4 |
| AGAAAAAGGTCTGCAGACACCGGAACTGCA | 12 | WN/DEN4 |
| INARD | 13 | WN |
| ATCAATGCTCGTGAT | 14 | WN |
| LNSRN | 15 | DEN4 |
| CTGAACTCGAGGAAC | 16 | DEN4 |
| INSRN | 17 | WN/DEN4 |
| ATCAACTCGAGGAAC | 18 | WN/DEN4 |

Figure 3:
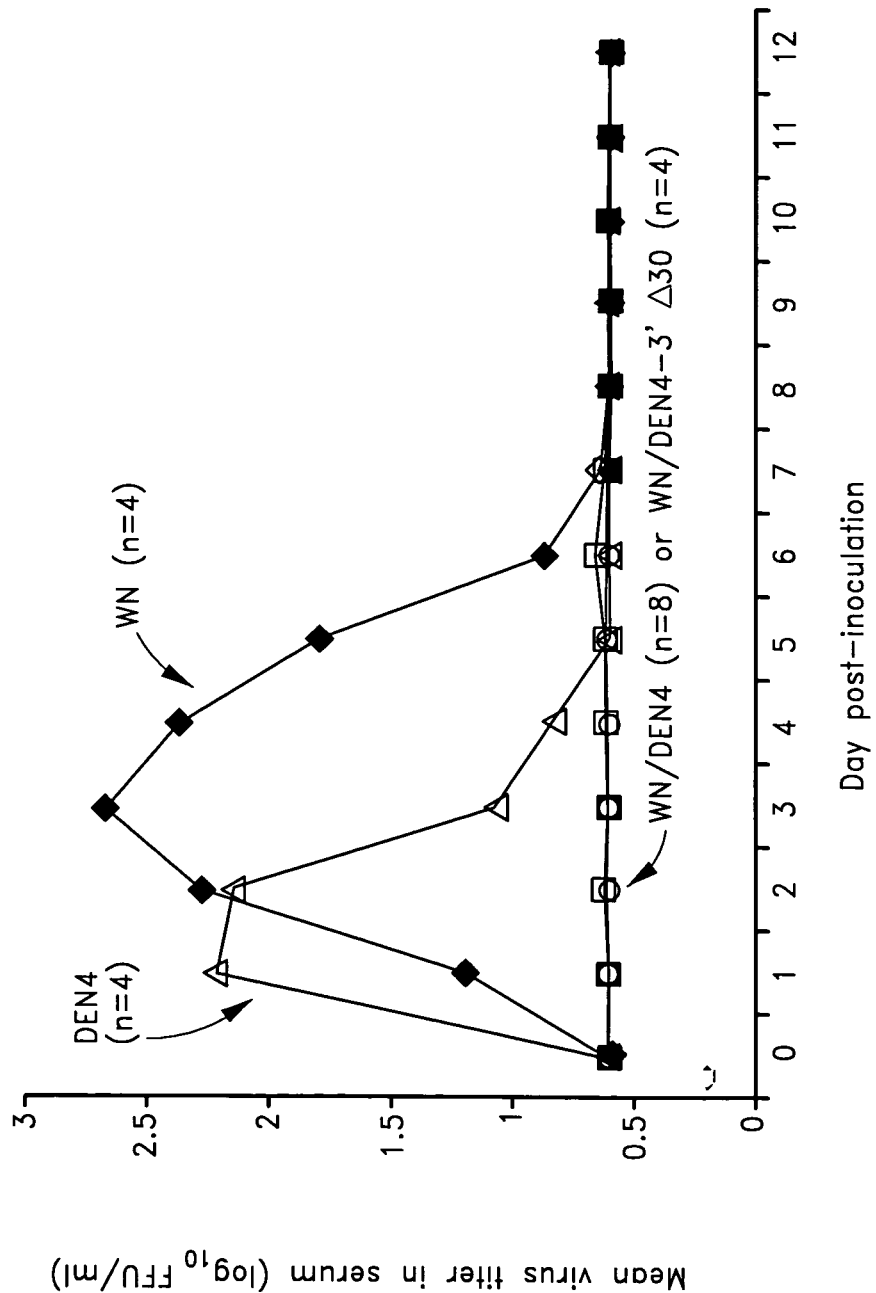

FIG. 3 shows the viremia of rhesus monkeys inoculated with parental WN or DEN4 virus or their WN/DEN4 chimera or its 3' deletion mutant WN/DEN4-3'Δ30. Twenty rhesus monkeys (*Maccaca mulatta*) in groups of 4 were inoculated subcutaneously (SC) with WN, DEN4, WN/DEN4 clone 18 or WN/DEN4-3'Δ30 clone 1. The quantity of virus in monkey serum was determined by direct titration in Vero cells using immunostaining focus-forming assay. Viremia was tested daily for 12 days post-inoculation for each monkey individually. Mean virus titer in serum of each monkey group shown; n is number of monkeys in group. The limit of detection of virus was $10^{0.7}$ FFU/ml, and the WN/DEN4 and WN/DEN4-3'Δ30 viruses were at or below the level of detection of virus in serum.

FIG. 4. A. The Δ30 mutation removes 30 contiguous nucleotides (shaded) from the 3' UTR of DEN4. Nucleotides are numbered from the 3' terminus. B. Nucleotide sequence alignment of the TL2 region of DEN4 and DEN1 and their Δ30 derivatives. Also shown is the corresponding region for each of the four DEN serotypes, with upper case letters indicating sequence homology among all 4 serotypes, underlining indicating nucleotide pairing to form the stem structure. C. Predicted secondary structure of the TL2 region of each DEN serotype. Nucleotides that are removed by the Δ30 mutation for the already constructed DEN1Δ30, DEN4Δ30, DEN2Δ30 viruses are indicated (boxed) on the left and the proposed DEN3Δ30 virus is on the right (DEN1—nts 10562-10591, DEN2 Tonga/74—nts 10541-10570, DEN3 Sleman/78—nts 10535-10565, and DEN4—nts 10478-10507).

Table of Sequences from FIG. 4

| SEQUENCE | SEQ ID NO | SOURCE |
|---|---|---|
| GGCCCGAAGCCAGGAGGAAGCUGUACUCCUGGUGGAAGGACUAGAGGUUAG | 19 | DEN4 |
| GGGGCCCGAAGCCAGGAGGAAGCUGUACUCCUGGUGGAAGGAGUAGA | 20 | DEN4 |
| GGGGCCCAAGACUAGA | 21 | DEN4Δ30 |
| GGGGCCCAACACCAGGGGAAGCUGUACCCUGGUGGUAAGGACUAGA | 22 | DEN1 |
| GGGGCCCAAGACUAGA | 23 | DEN1Δ30 |
| GGGGCCGAAGGUGAGAUGAAGCUGUAGUCUCACUGGAAGGACUAGA | 24 | DEN2 |
| GGGGCCCGAGCUCUGAGGGAAGCUGUACCUCCUUGCAAAGGACUAGA | 25 | DEN3 |
| GCAGCAGCGGGGCCCAACAGCAGGGGAAGCUGUACCCUGGUGGUAAGGACUAGAGGUUAGAGGAGACCCCCCGGAACAACAA | 26 | DEN1 |
| AGCAAAAGGGGGCCCGAAGCCAGGAGGAAGCUGUACUCCUGGUGGAAGGACUAGAGGUUAGAGGAGACCCCCCCAACACAAAA | 27 | DEN4 |
| AGCAACAAUGGGGCCCAAGGUGAGAUGAAGCUGUAGUCUCACUGGAAGGACUAGAGGUUAGAGGAGACCCCCCCAAAACAAAA | 28 | DEN2 |
| GCAGCAGGGGGCCCGAGCUCUGAGGGAAGCUGUACCUCCUUGCAAAGGACUAGAGGUUAGAGGAGACCCCCCGCAAAUAAAA | 29 | DEN3 |

Brief Description of the Sequences

GenBank Accession No. or description

| DEN1 | U88535 |
| DEN2 | Tonga/74 (SEQ ID No: 30 and 31)* |
| DEN3 | Sleman/78 (SEQ ID No: 32 and 33)** |
| DEN4 | AF326825 |

*DEN2 (Tonga/74) cDNA plasmid p2
Bases 1 to 10713: DEN2 virus genome cDNA:
Bases 97 to 10269: DEN2 polyprotein ORF
Bases 97 to 438: C protein ORF
Bases 439 to 936: prM protein ORF
Bases 937 to 2421: E protein ORF
Bases 2422 to 3477: NS1 protein ORF
Bases 3478 to 4131: NS2A protein ORF
Bases 4132 to 4521: NS2B protein ORF
Bases 4522 to 6375: NS3 protein ORF
Bases 6376 to 6756: NS4A protein ORF
Bases 6757 to 6825: 2K protein ORF
Bases 6826 to 7569: NS4B protein ORF
Bases 7570 to 10269: NS5 protein ORF
**DEN3 (Sleman/78) cDNA plasmid p3
Bases 1 to 10707: DEN3 virus genome cDNA
Bases 95 to 10264: DEN3 polyprotein ORF
Bases 95 to 436: C protein ORF
Bases 437 to 934: prM protein ORF
Bases 935 to 2413: E protein ORF
Bases 2414 to 3469: NS1 protein ORF
Bases 3470 to 4123: NS2A protein ORF
Bases 4124 to 4513: NS2B protein ORF
Bases 4514 to 6370: NS3 protein ORF
Bases 6371 to 6751: NS4A protein ORF
Bases 6752 to 6820: 2K protein ORF
Bases 6821 to 7564: NS4B protein ORF
Bases 7575 to 10264: NS5 protein ORF

DETAILED DESCRIPTION OF THE PREFERRED EMBODIMENT

Immunogenic WN/DEN *flavivirus* chimeras and methods for preparing the WN/DEN *flavivirus* chimeras are provided herein. The immunogenic WN/DEN *flavivirus* chimeras are useful, alone or in combination, in a pharmaceutically acceptable carrier as immunogenic compositions to immunize and protect individuals and animals against infection by West Nile virus.

Chimeras of the present invention comprise nucleotide sequences encoding the immunogenic structural proteins of a West Nile virus and further nucleotide sequences selected from the backbone of a dengue virus. Chimeric viruses derived from the nucleotide sequences can be used to induce an immunogenic response against West Nile virus.

In another embodiment, the preferred chimera is a nucleic acid chimera comprising a first nucleotide sequence encoding at least one structural protein from a West Nile virus, and a second nucleotide sequence encoding nonstructural proteins from a dengue virus. In another embodiment the dengue virus is attenuated. In another embodiment the dengue virus is DEN4. In another embodiment, the structural protein can be the C protein of a West Nile virus, the prM protein of a West Nile virus, the E protein of a West Nile virus, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:
   1) Alanine (A), Serine (S), Threonine (T);
   2) Aspartic acid (D), Glutamic acid (E);
   3) Asparagine (N), Glutamine (Q);
   4) Arginine (R), Lysine (K);
   5) Isoleucine (I), Leucine (L), Methionine (M), Valine (V); and
   6) Phenylalanine (F), Tyrosine (Y), Tryptophan (W).

As used herein, the terms "virus chimera," "chimeric virus," "*flavivirus* chimera" and "chimeric *flavivirus*" means an infectious construct of the invention comprising nucleotide sequences encoding the immunogenicity of a West Nile virus and further nucleotide sequences derived from the backbone of a dengue virus.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a West Nile virus and further nucleotide sequences derived from the backbone of a dengue virus. Correspondingly, any chimeric *flavivirus* or *flavivirus* chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Flavivirus Chimeras

West Nile virus and dengue virus are mosquito-borne *flavivirus* pathogens. The *flavivirus* genome contains a 5' untranslated region (5' UTR), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' untranslated region (3' UTR). The viral structural proteins are C, prM and E, and the nonstructural proteins are NS1-NS5. The structural and nonstructural proteins are translated as a single polyprotein and processed by cellular and viral proteases.

The *flavivirus* chimeras of the invention are constructs formed by fusing structural protein genes from a West Nile virus with non-structural protein genes from a dengue virus, e.g., DEN1, DEN2, DEN3, or DEN4.

The attenuated, immunogenic *flavivirus* chimeras provided herein contain one or more of the structural protein genes, or antigenic portions thereof, of the West Nile virus against which immunogenicity is to be conferred, and the nonstructural protein genes of a dengue virus.

The chimera of the invention contains a dengue virus genome as the backbone, in which the structural protein gene(s) encoding C, prM, or E protein(s) of the dengue genome, or combinations thereof, are replaced with the corresponding structural protein gene(s) from a West Nile virus that is to be protected against. The resulting chimeric virus has the properties, by virtue of being chimerized with the dengue virus, of attenuation and is therefore reduced in virulence, but expresses antigenic epitopes of the WN structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding nonstructural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 *J Virol* 70:3930-3933; Durbin et al. 2001 *Am J Trop Med* 65:405-413). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of *Flavivirus* Chimeras

The *flavivirus* chimeras described herein can be produced by substituting at least one of the structural protein genes of the West Nile virus against which immunity is desired into a dengue virus genome backbone, using recombinant engineering techniques well known to those skilled in the art, namely, removing a designated dengue virus gene and replacing it with the desired corresponding gene of West Nile virus. Alternatively, using the sequences provided in GenBank, the nucleic acid molecules encoding the *flavivirus* proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a West Nile virus structural protein. Preferably the West Nile virus gene to be inserted is a gene encoding a C protein, a prM protein and/or an E protein. The sequence inserted into the dengue virus backbone can encode both the prM and E structural proteins. The sequence inserted into the dengue virus backbone can encode the C, prM and E structural proteins. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a West Nile virus or the substituted gene(s) that encode the prM and/or E structural protein(s) of a West Nile virus. In a particular embodiment of this invention, the substituted gene that encodes the structural protein of a West Nile virus directs the synthesis of a prM protein that contains Asp and Thr, respectively, at a position 3 and 6 amino acids downstream of the cleavage site that separates the capsid protein of DEN and the premembrane protein of West Nile virus.

Suitable chimeric viruses or nucleic acid chimeras containing nucleotide sequences encoding structural proteins of West Nile virus can be evaluated for usefulness as vaccines by screening them for phenotypic markers of attenuation that indicate reduction in virulence with retention of immunogenicity. Antigenicity and immunogenicity can be evaluated using in vitro or in vivo reactivity with West Nile antibodies or immunoreactive serum using routine screening procedures known to those skilled in the art.

Flavivirus Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a West Nile virus in a wild-type or an attenuated dengue virus backbone. For example, the chimera may express the structural protein genes of a West Nile virus in either of a dengue virus or an attenuated dengue virus background.

The strategy described herein of using a genetic background that contains nonstructural regions of a dengue virus genome, and, by chimerization, the properties of attenuation, to express the structural protein genes of a West Nile virus has lead to the development of live, attenuated *flavivirus* vaccine candidates that express structural protein genes of desired immunogenicity. Thus, vaccine candidates for control of West Nile virus pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various *flavivirus* strains. The cloning of virus-specific cDNA fragments can also be accomplished, if desired. The cDNA fragments containing the structural protein or nonstructural protein genes are amplified by reverse transcriptase-polymerase chain reaction (RT-PCR) from *flavivirus* RNA with various primers. Amplified fragments are cloned into the cleavage sites of other intermediate clones. Intermediate, chimeric *flavivirus* clones are then sequenced to verify the sequence of the inserted *flavivirus*-specific cDNA.

Full genome-length chimeric plasmids constructed by inserting the structural or nonstructural protein gene region of flaviviruses into vectors are obtainable using recombinant techniques well known to those skilled in the art.

Method of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans or domestic animals, such as horses or birds, especially individuals travelling to regions where West Nile virus infection is present, and also to inhabitants of those regions. The optimal time for administration of the composition is about one to three months before the initial exposure to the West Nile virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of West Nile virus and dengue virus are useful for designing nucleic acid probes and primers for the detection of West Nile virus and dengue virus chimeras in a sample or specimen with high sensitivity and specificity. Probes or primers corresponding to West Nile virus and dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding West Nile virus and dengue virus or complementary sequences thereof. By "selective" or "selectively" is meant a sequence which does not hybridize with other nucleic acids to prevent adequate detection of the West Nile virus sequence and dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in *Molecular Cloning: A Laboratory Manual, 2nd* ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of West Nile virus and dengue virus, the degree of complementarity between the hybridizing nucleic acid (probe or primer) and the sequence to which it hybridizes is at least enough to distinguish hybridization with a nucleic acid from other organisms.

The nucleic acid sequences encoding West Nile virus and dengue virus can be inserted into a vector, such as a plasmid, and recombinantly expressed in a living organism to produce recombinant West Nile virus and dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT-PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer 1996 *Nature Biotechnology* 14:303-308). Molecular beacon assays employ quencher and reporter dyes that differ from those used in the TaqMan assay. These and other detection systems may used by one skilled in the art.

West Nile Virus/Dengue Type 4 Virus Chimeras that are Reduced in Neurovirulence and Peripheral Virulence without Loss of Immunogenicity or Protective Efficacy A candidate live attenuated vaccine strain was constructed for West Nile virus (WN), a neurotropic *flavivirus* that has recently emerged in the U.S. Considerable attenuation for mice was achieved by chimerization with dengue virus type 4 (DEN4). The genes for the structural premembrane (prM) and envelope (E) proteins of DEN4 present in a full-length infectious cDNA clone were replaced by the corresponding genes of WN strain NY99. Two of 18 full-length cDNA clones of a WN/DEN4 chimera yielded full-length RNA transcripts that were infectious when transfected into susceptible cells. The two infectious clones shared a motif in the transmembrane signal domain located immediately downstream of the NS2B-NS3 protease cleavage site that separates the DEN4 capsid protein and the WN premembrane protein of the chimera. This motif, Asp and Thr at a position 3 and 6 amino acids downstream of the cleavage site, respectively, was not present in the 16 non-infectious cDNA clones. The WN/DEN4 chimera was highly attenuated in mice compared to its WN parent; the chimera was at least 28,500 times less neurovirulent in suckling mice inoculated intracerebrally and at least 10,000 times less virulent in adult mice inoculated intraperitoneally. Nonetheless, the WN/DEN4 chimera and a deletion mutant derived from it, were immunogenic and provided complete protection against lethal WN challenge. These observations provide the basis for pursuing the development of a live attenuated WN vaccine.

Recent advances in recombinant DNA technology have allowed us to develop a novel approach for constructing live attenuated *flavivirus* vaccines (Pletnev, A. G. et al. 1992 *PNAS USA* 89:10532-10536; Pletnev, A. G. & Men, R. 1998 *PNAS USA* 95:1746-1751; Pletnev, A. G. et al. 2000 *Virology* 274:26-31; Pletnev, A. G. et al. 2001 *J Virol* 75:8259-8267). Our approach was made possible by the conservation among flaviviruses of genome organization, number of viral proteins, replicative strategy, gene expression, virion structure and morphogenesis (Lindenbach, B. D. & Rice, C. M. 2001 in: *Fields Virology*, eds. Knipe, D. M. & Howley, P. M. Lippincott Williams and Wilkins, Philadelphia, 4-th ed., pp. 1043-1125). All flaviviruses have a positive sense non-segmented RNA genome that encodes a single long polyprotein that is processed to yield capsid (C), premembrane (prM) and envelope glycoprotein (E) structural proteins followed by nonstructural proteins NS1, NS2A, NS2B, NS3, NS4A, NS4B, and NS5 in that order. These shared properties suggested that viable chimeric viruses could be produced by replacing the genes for the viral structural proteins in a full-length infectious cDNA clone of a *flavivirus* with the corresponding viral genes (in cDNA form) of another *flavivirus*. When tested, this strategy was successful for chimeras that contained the sequence for viral structural proteins prM and E of tick-borne encephalitis virus (TBEV) or tick-borne Langat virus (LGT), while all other sequences were derived from the full-length infectious cDNA of mosquito-borne dengue type 4 virus (DEN4). This indicated that viral structural proteins of a disparate *flavivirus*, TBEV or LGT, could function in the context of cis-acting 5' and 3' sequences and nonstructural proteins of DEN4. Significantly, both chimeras proved to be highly attenuated in mice with respect to peripheral virulence, namely, the ability of a virus to spread to the CNS from a peripheral site of inoculation and cause encephalitis. Nonetheless, the chimeras proved to be immunogenic and able to induce resistance in mice against challenge with TBEV or LGT (Pletnev, A. G. et al. 1992 *PNAS USA* 89:10532-10536; Pletnev, A. G. & Men, R. 1998 *PNAS USA* 95:1746-1751; Pletnev, A. G. et al. 2000 *Virology* 274:26-31). It appeared that a favorable balance between reduction in virus replication in vivo (attenuation) and induction of protective immunity had been achieved. We interpret this to mean that tick-borne *flavivirus* prM and E can interact in the context of DEN4 nonstructural proteins and cis-acting 5' and 3' sequences at a level sufficient for infectivity and induction of immunity but not sufficient for full expression of virulence that requires a high level of replication in vivo and ability to spread into the CNS.

Although a logical extension of this strategy was to construct WN/DEN4 chimeras, we realized that viability could not be predicted in advance because some *flavivirus* combinations such as some Langat virus(prM and E)/dengue virus chimeras, as well as dengue virus(prM and E)/Langat dengue virus chimeras, have not proven to be viable. Nevertheless, we were surprisingly successful in constructing viable WN/DEN4 chimeras in which the structural prM and E protein genes of the distantly related mosquito-borne WN were substituted for the corresponding genes of DEN4. We also generated a WN/DEN4 chimera with a 30 nucleotide deletion in the 3' untranslated region (3' UTR) that had previously been shown to render DEN4 safe but still immunogenic in adult volunteers (Durbin, A. P. et al. 2001 *Am J Trop Med Hyg* 65:405-413). Studies in mice were first performed to evaluate neurovirulence, peripheral virulence, immunogenicity, and protective efficacy of the newly constructed WN/DEN4 chimeric viruses.

Materials and Methods.

Cells and Viruses

Simian Vero cells (WHO seed passage 143) and mosquito C6/36 cells were obtained from Dr. L. Potash (Novavax Inc., Rockville, Md.). These Vero cells are qualified for use in production of candidate human vaccines. Simian LLCMK$_2$ cells were purchased from the American Type Culture Collection (Manassas, Va.). Starting with West Nile virus, the WN wild-type strain NY99-35262 used in this study was kindly provided by Dr. R. Lanciotti (Centers for Disease Control and Prevention, Fort Collins, Colo.). It was originally isolated from a Chilean flamingo at the Bronx Zoo (New York) in 1999 (Lanciotti, R. S. et al. 1999 *Science* 286:2333-2337). The sequence of WN NY99 genome is available as GenBank accession number AF196835, per Table 1, and other strains of WN may substitute for the sequence of WN NY99 genome. A virus suspension prepared in Vero cells had a titer of $2.6 \times 10^7$ focus-forming units per milliliter (FFU/ml) as determined with Vero cells using an immunostaining focus-forming assay (Pletnev, A. G. 2001 *Virology* 282:288-300) and WN-specific mouse antibodies. Turning to dengue virus, wild-type DEN4 Caribbean strain 814669 (GenBank accession number AF326573) was used, which replicated in Vero cells with a titer of $1.1 \times 10^8$ FFU/ml. The sequence of recombinant DEN4 genome is available as GenBank accession number AF326825, per Table 1, and other strains of DEN4 may substitute for the sequence of DEN4 genome. The sequence of DEN1 genome is available as GenBank accession number U88536, the sequence of DEN2 genome is available as GenBank accession number M19197, and the sequence of DEN3 genome is available as GenBank accession number M93130, and any of these sequences may substitute for the sequence of DEN4 genome.

Chimeric WN/DEN4 cDNA and Recovery of Infectious Virus.

Plasmid p2A(XhoI) (Bray, M. & Lai, C.-J. 1991 *PNAS USA* 88:10342-10346) containing the DEN4 full-length infectious cDNA, previously employed for recovery of chimeric TBEV/DEN4 and LGT/DEN4 viruses (Pletnev, A. G. et al. 1992 *PNAS USA* 89:10532-10536; Pletnev, A. G. & Men, R. 1998 *PNAS. USA* 95:1746-1751), was used for construction of WN/DEN4 cDNA. This was achieved by substituting cDNA of the WN prM and E protein genes for those of the corresponding DEN4 genes (FIG. 1B). The source of WN cDNA was a PCR product that included nucleotides (nts) 233 to 2758 of the WN strain NY99 genome. This was also kindly provided by Dr. R. Lanciotti (CDC). The nucleotide sequence of the structural protein genes in this PCR fragment was determined and compared with the published sequence of WN NY99 (GenBank accession number AF196835). Three nucleotide differences ($C_{1893} \rightarrow U$, $C_{2370} \rightarrow U$ and $C_{2385} \rightarrow A$) were identified in the E protein sequence, none of which resulted in an amino acid substitution.

Prior experience with construction and analysis of tick-borne/DEN4 chimeras indicated that we could not predict a priori the sequence of the DEN4 C protein/tick-borne *flavivirus* prM protein junction required for viability (Pletnev, A. G. et al. 1992 *PNAS USA* 89:10532-10536; Pletnev, A. G. & Men, R. 1998 *PNAS. USA* 95:1746-1751). For this reason, we adopted an empirical approach and tested several different C/prM junction sequences (FIG. 2). This was not necessary for the downstream junction because it was located within the COOH-terminal region of WN E. Initially, 3 sets of C/prM junctions were tested but only one yielded a viable WN/DEN4 chimera (FIG. 2). The primers employed for construction of the chimeras by PCR used oligonucleotide 5'-TCAAAACAAAAGAAAAGATCTGCAGT-GACCGGAATTGCAGTCATGATTGGC-3' (SEQ ID NO: 34), or 5'-TCAAAACAAAAGAAAAGATCTGCAGG-GACCGGAATTGCAGTCATGATTGGC-3' (SEQ ID NO: 35), or 5'-TCAAAACAAAAGAAAAGATCTGCAGA-CACCGGAATTGCAGTCATGATTGGC-3' (SEQ ID NO: 36) as a forward primer and oligonucleotide 5'-CCGCAA-GAAACGTCATAGCAATTGACCTGT-CACTCGAGTTGATTCCCATCCACAA CAGAAGAGC-3' (SEQ ID NO: 37) as a reverse primer. Stable full-length WN/DEN4 cDNA clones were identified after transformation of *E. coli* BD 1528 with a ligation mixture that contained the PCR product and the vector both of which were digested by PstI and XhoI (FIG. 2). Sequences at the junctions between WN and DEN4 genes in each chimeric plasmid were verified.

Plasmid DNA containing full-length WN/DEN4 cDNA was linearized with Asp718. In vitro RNA synthesis and transfection of cells with its RNA transcripts were performed as described previously (Pletnev, A. G. 2001 *Virology* 282: 288-300). Briefly, RNA transcripts of full-length WN/DEN4 constructs listed in FIG. 2 were used to transfect simian LLCMK$_2$, simian Vero cells or mosquito C6/36 cells in the presence of LipofectAmine 2000 reagent (GIBCO BRL, Gaithersburg, Md.) in a BSL-3 laboratory generously provided by Dr. L. Markoff (CBER, FDA). Transfected cells were examined by immunofluorescence assay (IFA) for the presence of WN or DEN4 proteins using a WN- or DEN4-specific hyperimmune mouse ascitic fluid (HMAF). Two infectious chimeric viruses containing WN/DEN4 group 4 junctions (FIG. 2), namely, WN/DEN4 clone 18 and 55, were isolated. The recovered chimeras were amplified once in simian Vero or mosquito C6/36 cells, viral RNA was isolated and then reverse transcribed into cDNA that was used for sequence analysis (Table 1). In a similar manner, the sequence of the Vero cell-derived WN/DEN4 clone 18 was determined after an additional purification by two rounds of terminal end-point dilution and amplification in Vero cells infected at a multiplicity of 0.01. The resulting virus suspension had a titer of $1.7 \times 10^6$ FFU/ml.

To introduce a deletion into the 3' untranslated region (UTR) of WN/DEN4 genome, the DNA fragment between the XhoI site (nt 2345 of DEN4 genome; GenBank accession number AF326827) and the Asp718 site at the 3' end of plasmid WN/DEN4-18 DNA was replaced with the corresponding XhoI-Asp718-fragment derived from full-length cDNA of a DEN4 mutant, clone p4Δ30 (Durbin et al. 2001 *Am. J. Trop Med. Hyg* 65:405-413). This mutant had 30 nts deleted from the 3' untranslated region (UTR) of the genome between nts 10478-10507. Full-length RNA generated by SP6 polymerase from 10 different plasmids was tested for infectivity by transfection of simian Vero cells. Two individual WN/DEN4-3'Δ30 cDNA clones were infectious. The rescued deletion mutants, WN/DEN4-3'Δ30 clone 1 and 78, were purified twice by terminal end-point dilution and amplified in Vero cells to a titer of $1.4 \times 10^5$ and $6 \times 10^4$ FFU/ml, respectively. Viral RNA was isolated, and complete sequence of the 3' deletion mutant genome was determined (Table 1).

Evaluation of Parental and Chimeric Viruses in Mice

Neurovirulence of Vero cell culture-propagated parental WN (strain NY99), parental DEN4 (strain 814669), chimeric WN/DEN4 (clone 18) and its deletion mutant (clone 1) was evaluated in a BSL-3 facility. Three-day-old Swiss Webster mice (Taconic Farms) in groups of 9 to 12 were inoculated by the intracerebral (IC) route with decimal dilutions ranging from 0.1 to $10^5$ FFU of virus in 0.03 ml of MEM/0.25% human serum albumin. Mice were observed for 21 days for development of fatal encephalitis. The 50% lethal dose (LD$_{50}$) of each virus was determined by the method of Reed and Muench (Reed, L. J. & Muench, H. 1938 *Am. J Hyg* 27:493-497). Parental and chimeric viruses were also analyzed for peripheral virulence by intraperitoneal (IP) inoculation of 3-week-old Swiss female mice in groups of 10. Mice were inoculated with decimal dilutions of virus ranging from 0.1 to $10^5$ FFU and observed for 28 days for fatal encephalitis. Moribund mice were humanely euthanized.

Mice that survived IP inoculation were bled on day 28 to evaluate the WN-specific neutralizing antibody response. Serum from mice in each group was pooled and the WN virus-neutralizing antibody titer of the serum pool was determined by FFU reduction assay in Vero cells as described previously (Pletnev, A. G. et al. 2001 *J Virol* 75:8259-8267; Pletnev, A. G. 2001 *Virology* 282:288-300). Briefly, a 1:10 dilution of pooled sera was prepared in MEM containing 2% fetal bovine serum (FBS) and then heat inactivated for 30 min at 56° C. Serial twofold dilutions of inactivated pooled sera were mixed with an equal volume of a virus suspension containing approximately 50 FFU of WN. The mixture was incubated for 30 min at 37° C., and 0.4 ml was then added to duplicate wells of Vero cells in a 6-well plate. After 1 h of absorption at 37° C., the inoculum was removed and cells were overlaid with MEM containing 2% FBS, 50 μg/ml gentamycin, 0.25 μg/ml fungizone, and 1% tragacanth gum. Antibody titer was determined after 2 days of incubation by an immunostaining focus-forming assay (Pletnev, A. G. 2001 *Virology* 282:288-300) that used WN-specific HMAF. Neutralizing antibody titer was the highest dilution of pooled sera that reduced focus formation 50% compared to sera collected from non-immunized mice.

The surviving mice were challenged IP on day 29 with 100 IP LD$_{50}$ ($10^3$ FFU) of parental WN virus and observed for fatal encephalitis for a period of 21 days. Moribund mice were humanely euthanized.

Results.

Construction and Recovery of Chimeric WN/DEN4 Viruses

In total we constructed 18 plasmids that contained full-length chimeric WN/DEN4 cDNA which included the structural prM and E protein genes of the WN strain NY99 with all other sequences derived from DEN4 (FIG. 2). Full-length RNA generated by SP6 RNA polymerase from only 2 of the 18 chimeric cDNAs was infectious when transfected into mosquito C6/36 or simian Vero cells. Evidence for virus infectivity was detected by IFA. In the case of the 2 viable chimeric viruses, 80-100% of transfected cells were infected by day 5 as indicated by IFA using WN-specific HMAF. The 2 viable chimeric viruses (WN/DEN4 clones 18 and 55) had the C/prM intergenic junction sequence of group 4 chimera shown in FIG. 2, i.e., +3 Asp and +6 Thr amino acids downstream of the cleavage site, respectively. The presence of this junction was confirmed by sequence analysis of the recovered chimeras. Also, the complete genomic sequence of the two chimeras rescued from cDNA in Vero cells was determined and compared with the consensus sequence of their parental WN NY99 and DEN4 viruses as well as the nucleotide sequence of the WN/DEN4 viral chimera insert in the plasmid-DNA from which infectious RNA transcripts were derived (Table 1). Analysis of plasmid DNAs revealed 4 differences in nucleotide sequence from the consensus WN sequence determined by RT-PCR of a high titered suspension of WN strain NY99. Three of these differences produced amino acid substitutions in prM (Ile$_6$→Thr and Ile$_{146}$→Val) and E (Thr$_{282}$→Ala). In addition, variability between (i) Glu$_{92}$ and Asp and (ii) Leu$_{112}$ and Ser was identified in the DEN4 NS3 and NS4B nonstructural proteins of the WN/DEN4 clone 55. Also, sequence of the Vero cell-grown WN/DEN4 clone 18 differed from its progenitor plasmid cDNA sequence in the DEN4 NS4B gene. A change U$_{7162}$→C that caused the substitution Leu$_{112}$→Ser was identified, which was observed previously (Blaney, J. E. et al. 2001 *J Virol* 75:9731-9740). Interestingly, a different substitution at this locus, Leu$_{112}$→Phe, was also previously observed by Blaney et al. upon passage of wild-type DEN4 in Vero cells.

Following our success in constructing full-length infectious WN/DEN4 cDNAs, we constructed chimeric virus mutants with a 30 nucleotide deletion in their 3' untranslated region (UTR). Two mutants, WN/DEN4-3'Δ30 clone 1 and clone 78, were recovered from transfected Vero cells. The complete sequence of both these clones was analyzed (Table 1). Sequence of clone 78 differed from the sequence of plasmid DNA from which its infectious RNA transcripts were derived. A change of C$_{7141}$→U produced an amino acid substitution Thr$_{105}$→Ile in the NS4B protein. The WN/DEN4-3'Δ30 clone 1 also exhibited only one nucleotide difference from the plasmid cDNA sequence. This resulted in the same NS4B amino acid change (Leu$_{112}$→Ser) that was observed in WN/DEN4 clone 18.

The WN/DEN4 chimera replicated more efficiently in Vero cells than did WN/DEN4-3'Δ30. The unmodified WN/DEN4 chimera reached a titer of $10^6$ FFU/ml on day 6 in cells infected with a multiplicity of infection of 0.01; this was approximately 10-fold higher than the titer attained by the deletion mutant by day 6. The titer of the unmodified chimera was nearly the same as that attained by parental DEN4 under the same conditions.

Mouse Neurovirulence.

Before evaluating chimeric viruses for virulence in mice, the Vero cell-rescued chimeric WN/DEN4 virus and its 3' deletion mutant were cloned biologically twice by terminal end-point dilution and then amplified in qualified Vero cells. The titer attained by the Vero cell-adapted WN/DEN4 clone 18 and WN/DEN4-3'Δ30 clone 1 was $1.7 \times 10^6$ FFU/ml and $1.4 \times 10^5$ FFU/ml, respectively.

Both chimeric WN/DEN4 virus and the deletion mutant WN/DEN4-3'Δ30 as well as parental WN strain NY99 and DEN4 strain 814669 viruses were evaluated in 3-day-old Swiss mice for neurovirulence by direct IC inoculation (Table 2). Wild-type WN NY99 grown in Vero cells was highly neurovirulent with an intracerebral LD$_{50}$ of 0.35 FFU in suckling Swiss mice. Wild-type DEN4 also grown in Vero cells was less neurovirulent with an IC LD$_{50}$ of 407 FFU. Both WN/DEN4 and WN/DEN4-3'Δ30 chimeric viruses exhibited a significant reduction in neurovirulence compared to their WN and DEN4 parents. All of the mice inoculated IC with $10^3$ FFU of WN/DEN4 or its 3' deletion mutant survived during a 21 day observation period. At a higher dose of $10^4$ FFU, only 4 of 11 mice inoculated with WN/DEN4 died. Thus, in suckling mice the WN/DEN4 chimera was more than 28,571 times less neurovirulent than its WN parent. The chimera with the 30 nt deletion was also significantly less neurovirulent than its WN parent. These observations are consistent with earlier observations that chimerization of TBEV or LGT with DEN4 significantly reduced their neurovirulence for mice (Pletnev, A. G. et al. 1992 *PNAS USA* 89:10532-10536; Pletnev, A. G. & Men, R. 1998 *PNAS. USA* 95:1746-1751; Pletnev, A. G., Bray, M. & Lai, C.-J. 1993 *J Virol* 67:4956-4963).

Peripheral Virulence in Mice

Subsequently, we evaluated the chimeric viruses for peripheral virulence, i.e., the ability of virus inoculated by the IP route to spread from a peripheral site to the central nervous system and cause encephalitis. Both chimeras were highly attenuated compared to their WN parent (Table 2 and 3). Notably, IP inoculation of $10^4$ FFU of the deletion mutant chimera or $10^5$ FFU of the unmodified chimera did not induce fatal encephalitis in any of the 3-week-old Swiss mice, whereas the IP LD$_{50}$ for the WN parent was 10 FFU.

The chimeras were also evaluated in adult SCID mice because previous studies of tick-borne flaviviruses and their DEN4 chimeras indicated that SCID mice were a more sensitive detector of peripheral virulence than immunocompetent mice. Intraperitoneal inoculation of the maximum quantity of chimera, $10^5$ FFU for WN/DEN4 and $10^4$ FFU for WN/DEN4-3'Δ30, did not produce encephalitis in any instance (Table 2). In contrast, the IP LD$_{50}$ for parental WN was 6 FFU. These observations confirmed that the ablation of peripheral virulence of the WN chimeras had been achieved.

Immunogenicity and Protective Efficacy of Chimeric Viruses in Mice

The two chimeras were immunogenic; a single IP inoculation of $10^2$ FFU of the WN/DEN4 chimera induced a moderate level of serum WN neutralizing antibodies (1:93), while a 10-fold higher concentration ($10^3$ FFU) induced a very high titer of WN neutralizing antibodies (1:1189) (Table 3). Also, $10^3$ FFU of the chimeric WN/DEN4-3'Δ30 deletion mutant stimulated a high level of such antibodies (1:292). Intraperitoneal challenge of the immunized mice on day 29 with 100 IP LD$_{50}$ ($10^3$ FFU) of parental WN indicated that the chimeras provided 90 to 100% protection against this high dose WN challenge (Table 3). There was a good correlation between the titer of serum WN neutralizing antibodies that developed in response to immunization and the degree of resistance induced. All unvaccinated control mice developed signs of CNS disease 7 to 13 days after challenge with 100 IP LD$_{50}$ of WN and these animals died shortly thereafter. To determine whether there was an age-related resistance of mice to WN, another group of 7-week-old mice also served as controls; they were the same age as immunized mice at time of challenge. This group of older control mice was challenged with one IP LD$_{50}$, determined in 3-week-old mice. Seven of eight mice died during the 21 day observation period. This indicated that age-dependent resistance of mice to WN was not a factor in the observed protective effect of immunization.

TABLE 1

Mutations that were identified in genome of the WN/DEN4 or WN/DEN4-3'Δ30 chimera during cloning and rescue of chimera from cDNA in simian Vero cells

| Virus | Region of genome | NT (position)* | WN/DEN4 | | | WN/DEN4-3'Δ30 | | | Amino acid change |
|---|---|---|---|---|---|---|---|---|---|
| | | | pDNA** | Recombinant virus | | pDNA+ | Recombinant virus | | |
| | | | | clone 55 | clone 18 | | clone 1 | clone 78 | |
| WN | prM | U$_{428}$ | C | C | C | C | C | C | Ile$_6$ → Thr |
| | | A$_{847}$ | G | G | G | G | G | G | Ile$_{146}$ → Val |
| | E | A$_{1566}$ | G | G | G | G | G | G | silent |
| | | A$_{1810}$ | G | G | G | G | G | G | Thr$_{282}$ → Ala |
| DEN4 | NS3 | A$_{4799}$ | A | C/a | A | A | A | A | Glu$_{92}$ → Asp |
| | NS4B | C$_{7141}$ | C | C | C | C | C | U | Thr$_{105}$ → Ile |
| | | U$_{7162}$ | U | C/u | C | U | C | U | Leu$_{112}$ → Ser |

*Numbering of nucleotide sequence of structural protein genes derived from the sequence of WN NY99 genome (GenBank accession number AF196835) and numbering of nucleotide sequence of nonstructural protein genes derived from the sequence of DEN4 genome (GenBank accession number AF326825).
**Plasmid DNA.
+Comparison of the pDNA for the parental cDNA clones used to derive the chimeric viruses are indicated in Durbin, A. et al. 2001 Am J Trop Med Hyg 65: 405–413

TABLE 2

Neurovirulence and peripheral virulence of parental West Nile virus (WN) or Dengue type 4 virus (DEN4) and their chimeric WN/DEN4 virus or its 3' deletion mutant WN/DEN4-3' Δ30 in mice as assayed by intracerebral (IC) or intraperitoneal (IP) inoculation

| | Neurovirulence: | | Peripheral virulence: | | |
|---|---|---|---|---|---|
| Virus | $LD_{50}$ (FFU) after IC inoculation of 3-day-old Swiss mice | Reduction from WN parent | $LD_{50}$ (FFU) after IP inoculation of 3-week-old Swiss mice | $LD_{50}$ (FFU) after IP inoculation of 3-week-old SCID mice | Reduction from WN parent |
| DEN4 | 407 | — | >100,000* | >100,000* | — |
| WN | 0.35 | — | 10 | 6.0 | — |
| WN/DEN4 Chimera (clone 18) | >10,000* | >28,571x | >100,000* | >100,000* | >10,000x |
| WN/DEN4-3' Δ30 Chimera (clone 1) | >1,000* | >2,857x | >10,000* | >10,000* | >1,000x |

Note:
Each decimal dilution was tested in 9 to 12 mice in group.
*Highest concentration tested.

TABLE 3

Peripheral virulence, antibody response and protective efficacy of parental (WN or DEN4) viruses and chimeric WN/DEN4 virus or its 3' deletion mutant WN/DEN4-3'Δ30 in 3-week-old Swiss mice

| Mice inoculated IP with | Dose (FFU*) inoculated | Mortality after IP inoculation | Mean titer of WN neutralizing antibody in pooled sera on day 28 | Mortality after survivors inoculated IP with 100 IP $LD_{50}$ of WN on day 29 |
|---|---|---|---|---|
| WN | 0.1 | 0/10 | <1:10 | 10/10 (100%) |
| | 1 | 0/10 | 1:24 | 10/10 (100%) |
| | 10 | 5/10 | 1:40 | 4/5 (80%) |
| | 100 | 10/10 | | |
| | 1,000 | 9/10 | | |
| | 10,000 | 10/10 | | |
| WN/DEN4 Chimera (clone 18) | 1 | 0/10 | 1:26 | 10/10 (100%) |
| | 10 | 0/10 | 1:21 | 9/10 (90%) |
| | 100 | 0/10 | 1:93 | 7/10 (70%) |
| | 1,000 | 0/10 | 1:1189 | 0/10 (0%) |
| | 10,000 | 0/10 | 1:585 | 0/9** (0%) |
| | 100,000 | 0/10 | 1:924 | 0/10 (0%) |
| WN/DEN4-3'Δ30 Chimera (clone 1) | 1 | 0/10 | 1:28 | 9/10 (90%) |
| | 10 | 0/10 | <1:10 | 9/10 (90%) |
| | 100 | 0/10 | 1:14 | 8/10 (80%) |
| | 1,000 | 0/10 | 1:292 | 1/10 (10%) |
| | 10,000 | 0/10 | 1:269 | 0/10 (0%) |
| DEN4 | 1,000 | 0/10 | <1:10 | 10/10 (100%) |
| | 10,000 | 0/10 | 1:13 | 8/10 (80%) |
| | 100,000 | 0/10 | 1:22 | 10/10 (100%) |
| Control | | | <1:10 | 10/10 (100%) |

*Focus forming unit.
**One of the 10 mice inoculated died as a result of trauma; WN virus was not detected in the brain by tissue culture (Vero cell) assay.

TABLE 4

Chimeric WN/DEN4 and its 3' deletion mutant WN/DEN4-3' Δ30 are attenuated in rhesus monkeys

| | | | Viremia | | |
|---|---|---|---|---|---|
| Virus inoculated subcutaneously | Dose of virus (FFU) | No. of monkeys inoculated | No. viremic | Mean duration (days) | Mean peak titer of viremia during 2 weeks post-inoculation $\log_{10}$ (FFU/ml)* |
| WN/DEN4 | $10^5$ | 4 | 3 | 1.5 | 0.78 |
| | $10^6$ | 4 | 2 | 0.5 | <0.7 |
| WN/DEN4-3' Δ30 | $10^5$ | 4 | 0 | 0 | <0.7 |
| WN | $10^5$ | 2 | 2 | 5.5 | 2.63 |
| | $10^6$ | 2 | 2 | 5.5 | 2.76 |
| DEN4 | $10^6$ | 4 | 4 | 3.8 | 2.23 |

*Tested daily for 10 days.
Note:
0.7 $\log_{10}$ (FFU/ml) is a lowest level of detectable viremia in serum. 0.6 log10 (FFU/ml) was used to calculate mean peak titer of viremia for animals that had no detectable viremia.

TABLE 5

Immunogenicity and protective efficacy of chimeric WN/DEN4 and its 3' deletion mutant WN/DEN4-3'Δ30 in rhesus monkeys

| Group of monkeys inoculated SC with | | | Geo. mean titer of WN serum neutralizing antibody on post immunization day 42 (range) | No. of monkeys viremic during 2 weeks post challenge with $10^5$ FFU of WN (Mean peak titer; $\log_{10}$ FFU/ml)* |
|---|---|---|---|---|
| Virus | Dose (FFU) | No. of monkeys | | |
| WN/DEN4 | $10^5$ | 4 | 1:661 (416-1126) | 0 |
|  | $10^6$ | 4 | 1:501 (270-727) | 0 |
| WN/DEN4-3'Δ30 | $10^5$ | 4 | 1:186 (109-247) | 0 |
| WN | $10^5$ | 2 | 1:1318 (1305-1324) | 0 |
|  | $10^6$ | 2 | 1:708 (599-842) | 0 |
| DEN4 | $10^6$ | 4 | <1:20 | 4 (2.04**) |

*Tested daily for 10 days.
**Mean duration of viremia was 3.75 days.

Attenuation, Immunogenicity and Protective Efficacy of West Nile/DEN4 Chimeras in Rhesus Monkeys It has been established that some non-human primates are readily infected with a number of flaviviruses by the peripheral route (Simmons et al. 1931 *Philipp J Sci* 44:1-247; Rosen, 1958 *Am J Trop Med Hyg* 7:406-410). Thus, infection of monkeys represents the closest experimental system to *flavivirus* infection of humans. The response of monkeys to *flavivirus* infection is similar to that of humans in that there is a four to six day viremia, although lower primates do not usually develop clinical *flavivirus* symptoms. The objectives of *flavivirus* studies in monkeys are: (1) to evaluate the immunogenicity of various candidate vaccines; (2) to evaluate the infectivity and virulence (attenuation phenotype) of candidate vaccines as measured by the duration of viremia in days and the peak virus titer in FFU/ml; and (3) to evaluate the protective efficacy of the candidate vaccines against challenge by wild-type *flavivirus*.

1) Inoculation: Each monkey is inoculated with a total of $10^5$ or $10^6$ FFU of virus diluted in L15 medium with SPG (Durbin, A. P. et al. 2001 *Am J Trop Med Hyg* 65:405-413). Normally, virus is inoculated by the subcutaneous route to anesthetized animals.

2) Blood collection: Following inoculation of virus, blood samples of 3.0 ml are taken daily for two weeks and 5.0 ml at 3 weeks, 4 weeks, 5 weeks, and 6 weeks.

3) Challenge with parental wild-type *flavivirus*: Where virus challenge is deemed appropriate to evaluate the protective efficacy, monkeys are inoculated with wild-type virus at $10^5$ FFU/dose in a 1.0 ml volume subcutaneously in the upper arm area.

4) Laboratory assays: Serum samples are collected to be used to determine: (a) the duration and level of viremia by direct viral plaque or FFU assay; and (b) the titer of neutralizing antibodies induced as measured by FFU reduction neutralization test, all tests well known to those skilled in the art of vaccine development.

Attenuation, immunogenicity, and protective efficacy of the West Nile/DEN4 chimeras were studied in 20 rhesus monkeys (Tables 4 and 5). Eight monkeys were inoculated subcutaneously (SC) with WN/DEN4 (clone 18); 4 animals received $10^5$ FFU, while the other 4 received $10^6$ FFU. Four monkeys were inoculated SC with $10^5$ FFU of WN/DEN4-3'Δ30 (clone 1). A group of 4 monkeys was inoculated SC with parental West Nile virus; 2 animals received $10^5$ FFU, while the other received $10^6$ FFU. Finally, another group of 4 monkeys was inoculated SC with $10^6$ of DEN4 (Table 4).

Each of the monkeys inoculated SC with $10^5$ or $10^6$ FFU of West Nile virus developed a viremia that lasted 5 to 6 days and attained a mean peak titer of 2.6 to 2.8 $\log_{10}$ (FFU/ml) (FIG. 3, Table 4). In contrast, WN/DEN4 induced viremia in only 5 of the 8 monkeys inoculated with $10^5$ or $10^6$ FFU. Viremia lasted only one to two days and attained a peak titer 100 fold lower than observed for WN infected monkeys. Significantly, each of the 4 monkeys inoculated SC with $10^5$ FFU of the WN/DEN4-3'Δ30 mutant failed to develop a detectable viremia.

Although the WN/DEN chimera and its deletion mutant were significantly attenuated for rhesus monkeys, these hybrid viruses induced a moderate to high level of serum WN neutralizing antibodies in each immunized animal (Table 5). The two chimeras also induced complete resistance to SC challenge with $10^5$ FFU of West Nile virus on day 42 post immunization. Viremia of WN was not detected in any of the 12 monkeys immunized with WN/DEN4 or its deletion mutant. The West Nile challenge virus replicated efficiently in monkeys previously infected with DEN4 virus. This indicates that the high level of protection against WN challenge afforded by infection with WN/DEN4 chimeric viruses is specified by the WN protective antigens in the chimera and not by the DEN4 component of the chimera.

Figure 4C:
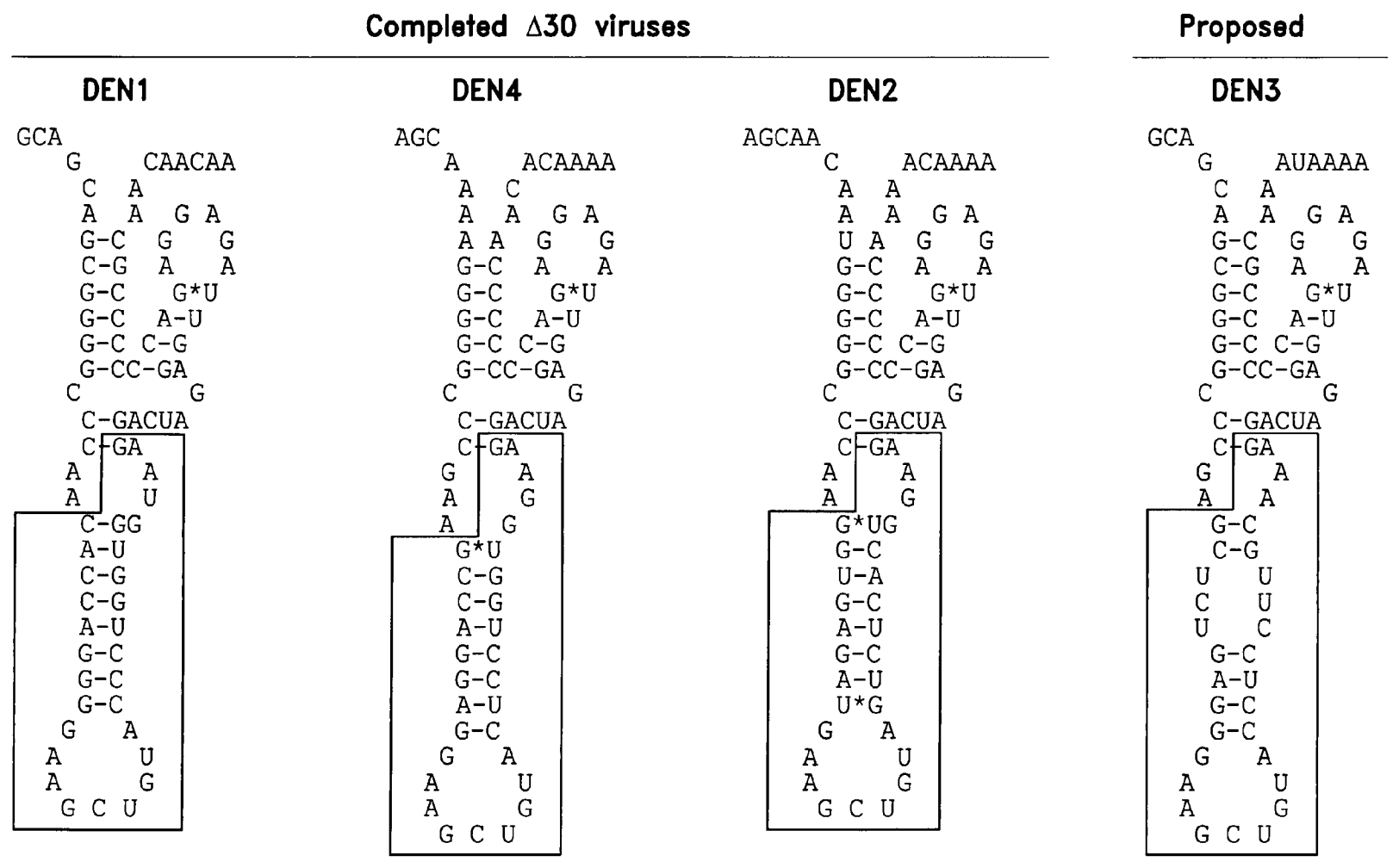

The Δ30 mutation was first described and characterized in the DEN4 virus (Men, R. et al. 1996 *J Virol* 70:3930-7). In DEN4, the mutation consists of the removal of 30 contiguous nucleotides comprising nucleotides 10478-10507 of the 3' UTR (FIG. 4A) which form a putative stem-loop structure referred to as TL2 (Proutski, V. et al. 1997 *Nucleic Acids Res* 25:1194-202). Among the flaviviruses, large portions of the UTR form highly conserved secondary structures (Hahn, C. S. et al. 1987 *J Mol Biol* 198:33-41; Proutski, V. et al. 1997 *Nucleic Acids Res* 25:1194-202). Although the individual nucleotides are not necessarily conserved in these regions, appropriate base pairing preserves the stem-loop structure in each serotype, a fact that is not readily apparent when only considering the primary sequence (FIG. 4B, C). We have demonstrated that the Δ30 mutation specifies an attenuation phenotype that is transportable to other DEN serotypes, DEN1 (Whitehead, S. S. et al. 2003 *J Virol* 77:1653-1657) and DEN2 (Tonga/74) (U.S. Provisional Application, filed Dec. 23, 2002, as NIH230.002PR). This indicates that the Δ30 mutation is expected to have a corresponding effect on DEN3 wild-type virus. We envision constructing this remaining virus by deletion of the TL2 region of the virus, e.g., DEN3 (Sleman/78) (FIG. 4C). These attenuated or wild type DEN1, DEN2, or DEN3 viruses could readily replace the DEN4 wild type or DEN4-3'Δ30 viruses presented in these examples.

These findings specifically identify two candidate WN live attenuated virus vaccines. The first, WN/DEN4, is about 100-fold attenuated in comparison to WN wild-type virus as indicated by the greatly restricted level of viremia. The second virus, WN/DEN4-3'Δ30, is more attenuated than WN/DEN4 as indicated by the absence of viremia in monkey serum and by the moderately decreased serum neutralizing antibody response. Thus, the methods and viruses taught provide live attenuated WN vaccines of differing levels of attenuation, each of which is highly protective against wild-type WN virus challenge. Similar attenuated WN/DEN chimeric viruses on a DEN1, DEN2, or DEN3 background are envisioned.

Further Attenuation of WN/DEN4 Chimeras by Introduction of Additional Mutations in the Genes for the Non-Structural Proteins of DEN4 that Serve as a Component of these Vaccine Candidates We contemplate achieving an increase in the level of attenuation of the candidate vaccine WN/DEN4 or WN/DEN4-3'Δ30 chimera if need be by adding one or more attenuation mutations to the DEN4 component of the chimeras. A large set of mutations that attenuate DEN4 in mice (Blaney, et al. 2001 *J Virol* 75:9731-9740; Blaney, et al. 2002 *Virology* 300:125-139; Hanley, et al. 2002 *J Virol* 76:525-31) has been identified in the part of the DEN4 genome included in the WN/DEN4 chimeric viruses. Members from this set of attenuating mutations can be introduced in the WN/DEN4 chimeric virus to further attenuate these viruses. For example, it might be necessary to further attenuate the WN/DEN4 virus, which possesses some residual neurovirulence as indicated above. The feasibility of this approach to achieve further attenuation is exemplified by introducing a viable mutation that specifies a temperature sensitive phenotype as well as a phenotype of growth restriction in suckling mouse brain into the non-structural protein 3 (NS3) of the DEN4 component of the WN/DEN4 chimera. Mutation 4891 (isoleucine→threonine) had previously been identified at nucleotide 4891 of the NS3 gene of DEN4 (Blaney, et al. 2002 *Virology* 300:125-139). Mutation 4891 specified two desirable phenotypes, i.e., temperature sensitivity and growth restriction in brain tissue. Similarly, mutation 4995 (serine→proline), also in NS3, specified the same two desirable phenotypes (Blaney, et al. 2001 *J Virology* 75:9731-9740, 2001). The 4891 and 4995 mutations also increase replication fitness of DEN4 in Vero cells, i.e., they are Vero cell adaptation mutations. The wild type amino acid residue at DEN4 4891 (isoleucine) is conserved in DEN2 Tonga/74 and DEN3 Sleman/78, but not DEN1 West Pacific. The wild type amino acid residue at DEN4 4995 (serine) is conserved in DEN1 West Pacific, DEN2 Tonga/74, but not DEN3 Sleman. One or both of these mutations may also be included in a WN/DEN1, 2, or 3 chimera. Thus, their inclusion in WN/DEN4 virus is contemplated as achieving an increase in replication of the virus in Vero cells or the genetic stability of the mutation during manufacture in Vero cells.

Discussion.

Initially, we demonstrated that although prM and E proteins of distantly related tick-borne and mosquito-borne flaviviruses are highly divergent, these proteins could be interchanged in some instances without loss of virus viability (Pletnev, A. G. et al. 1992 *PNAS USA* 89:10532-10536; Pletnev, A. G. & Men, R. 1998 *PNAS USA* 95:1746-1751). This approach has been used to create new chimeric flaviviruses (Bray, M., Men, R. & Lai, C.-J. 1996 *J. Virol.* 70:4162-4166; Chambers, T. J. et al. 1999 *J Virol* 73:3095-3101; Guirakhoo, F. et al. 2000 *J Virol* 74:5477-5485; Huang, C. Y. et al. 2000 *J Virol* 74:3020-3028; Van Der Most, R. G. et al. 2000 *J Virol* 74:8094-8101; Caufour, P. S. et al. 2001 *Virus Res* 79:1-14).

Previously, we succeeded in constructing and recovering viable tick-borne/DEN4 chimeras (Pletnev, A. G. et al. 1992 *PNAS USA* 89:10532-10536; Pletnev, A. G. & Men, R. 1998 *PNAS USA* 95:1746-1751; Pletnev, A. G., Bray, M. & Lai, C.-J. 1993 *J Virol* 67:4956-4963). In these instances, the tick-borne *flavivirus* parent was tick-borne encephalitis virus, a highly virulent virus, or Langat virus, a naturally attenuated tick-borne virus. Thus, the two components of these chimeras had disparate vector hosts, namely ticks and in the case of DEN4, mosquitoes. Decreased efficiency of gene product interactions in the chimeras was thought to be the basis for the marked attenuation exhibited by these hybrid viruses. Nonetheless, although highly attenuated in mice, the TBEV/DEN4 and LGT/DEN4 chimeras were immunogenic and provided considerable protection against their parental tick-borne *flavivirus*. In the present instance, both virus parents of the WN/DEN4 chimeras are transmitted by mosquitoes. However, vector preference differs, *Aedes* for DEN4 and *Culex* for WN (Burke, D. S. & Monath, T. P. 2001 in *Fields Virology*, eds. Knipe, D. M. & Howley, P. M. Lippincott Williams and Wilkins, Philadelphia, 4-th ed., pp. 1043-1125; Hayes, C. G. 1989 in *The Arboviruses: Epidemiology and Ecology*, ed. Monath T. P. Boca Raton, F. L.: CRC Press, Volume V, pp. 59-88).

Figure 1A:
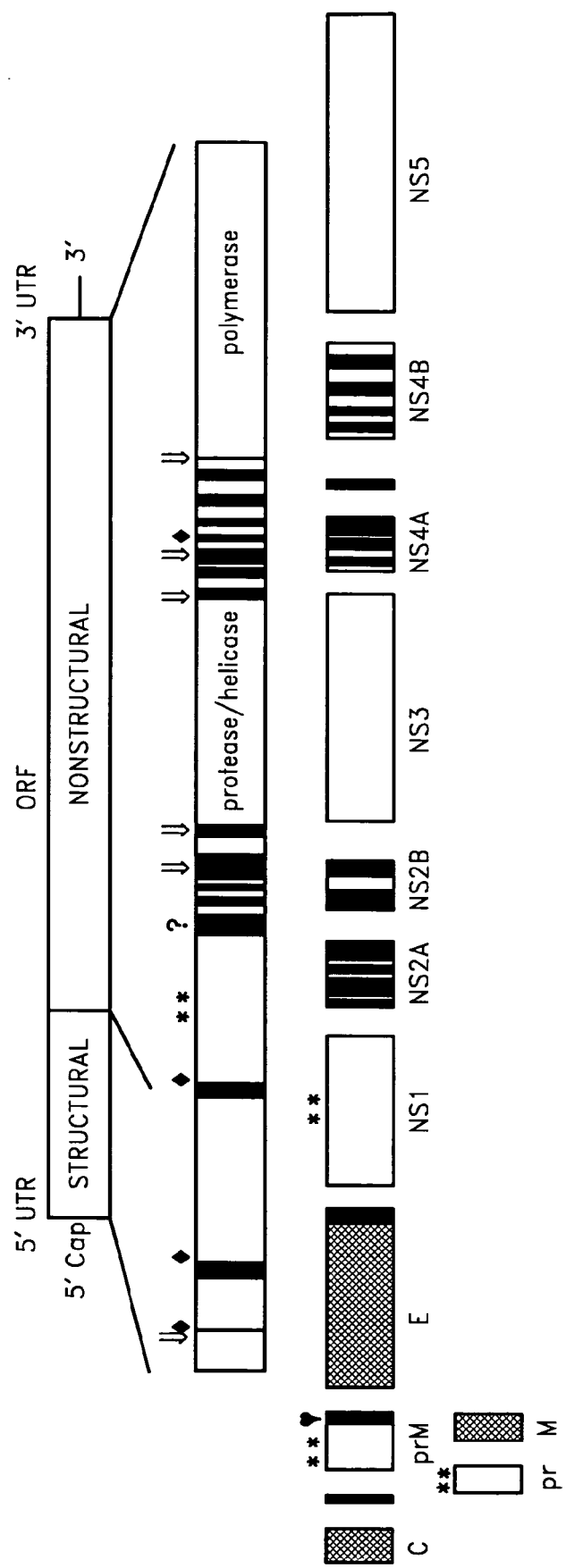
FIG. 1A shows the translation and processing of the *flavivirus* polyprotein. At the top is depicted the viral genome with the structural and nonstructural protein coding regions, the 5' cap, and the 5' and 3' untranslated regions (UTRs) indicated. Boxes below the genome indicate precursors and mature proteins generated by the proteolytic processing cascade. Mature structural proteins are indicated by shaded boxes and the nonstructural proteins and structural protein precursors by open boxes. Contiguous stretches of uncharged amino acids are shown by black bars. Asterisks denote proteins with N-linked glycans but do not necessarily indicate the position or number of sites utilized. Cleavage sites for host signalase (♦), the viral serine protease (⇓), furin or other Golgi-localized protease (♥), or unknown proteases (?) are indicated. Taken from Field's Virology, 2001 Fourth Edition, B. D. Lindenbach and C. M. Rice, page 998, Chapter 32.

In the present study, we constructed viable WN/DEN4 chimeras that contained a DEN4 genome whose genes for structural prM and E proteins were replaced by the corresponding genes of WN strain NY99. Among flaviviruses, the hydrophobic domain between C and prM ("transmembrane signal domain") varies in sequence and also varies in length from 14 to 20 amino acids (Stocks, C. E. & Lobigs, M. 1998 *J Virol* 72:2141-2149). It acts as a signal sequence for translocation of prM protein into the endoplasmic reticulum lumen where post-translation maturation of this protein occurs (Lindenbach, B. D. & Rice, C. M. 2001 in *Fields Virology*, eds. Knipe, D. M. & Howley, P. M. Lippincott Williams and Wilkins, Philadelphia, 4-th ed., pp. 1043-1125). This signal peptide is flanked at its $NH_2$-terminal region by the viral protease NS2B-NS3 cleavage site and at its COOH-terminal region by a cellular signalase cleavage site. Four different junctions at the protease cleavage site between DEN4 C and WN prM protein were introduced separately in chimeric constructs (FIG. 2). The C/prM fusion sequence at the viral protease cleavage site (KR↓S) in the chimeras was constructed to be similar to that of the DEN4 parent, which provides its NS2B-NS3 protease for the processing of the chimeric polyprotein. However, each of the chimeric constructs of group 1 and 2 chimeras contain a unique substitution in the transmembrane signal sequence at the third amino acid position downstream of the protease cleavage site, while another sequence is shared by group 3 and group 4 chimeras (FIG. 1A, FIG. 2). Thus, the transmembrane signal of the constructs is similar in length but exhibits polymorphism for group 1, group 2 and groups 3 and 4 together. This occurs at the third amino acid position downstream of the protease cleavage site. Viable WN/DEN4 virus was recovered only when construct number 4 (FIG. 2) was employed to prepare RNA transcripts for transfection. Infectious virus was recovered from 2 of 5 separate clones that encoded Asp in the 3+ amino acid position. And only the 2 clones that also contained a second-site mutation at the 6+ amino acid position downstream of the protease cleavage site that substituted Thr for Ile were infectious; this mutation occurred during cloning of cDNA in bacteria (FIG. 2, Table 1). In contrast, none of the 13 clones that encoded Gly or Val at the 3+ amino acid position produced infectious virus following transfection. This suggests that the transmembrane signal sequence between C and prM is a determinant of viability in the context of a WN/DEN4 chimera. This is consistent with an earlier observation made with yellow fever virus that the transmembrane signal sequence between C and prM protein plays a role in viability and neurovirulence (Lee, E. et al. 2000 *J. Virol.* 74:24-32).

The +3 and +6 Asp and Thr motif at the capsid protein-preM protein cleavage site that was required for viability of the chimera could not be predicted from the sequence of either parent, i.e., DEN4 and West Nile virus, because neither parent had this +3 and +6 motif. Success was achieved by testing a number of disparate sequences at the cleavage site and this led to the identification of the +3 and +6 Asp and Thr motif that was required for viability. For this reason, we advocate an empirical approach that embraces testing several different C/prM junction sequences for identification of other motifs that produce equally viable chimeric virus.

The WN strain NY99 exhibited considerable virulence in Swiss mice; its IC $LD_{50}$ was 0.35 FFU for suckling mice and its IP $LD_{50}$ was 10 FFU for 3-week-old Swiss mice (Table 2). Nearly the same level of neurovirulence was observed for a wild-type strain of WN isolated in Israel that was evaluated in CD-1 (ICR) mice: IC $LD_{50}$ and IP $LD_{50}$ were estimated to be 1.1 and 4.3 PFU, respectively (Halevy, M. et al. 1994 *Arch Virol* 137:355-370). In addition, a high degree of genomic similarity (>99.8%) between the WN NY99 and the WN Israel-1998 was recently confirmed by sequence analysis (Lanciotti, R. S. et al. 1999 *Science* 286:2333-2337) indicating that both highly pathogenic strains of WN, representing North American and Middle Eastern viruses, are closely related. Wild-type DEN4 Caribbean strain 814669 was moderately neurovirulent for suckling mice with an IC $LD_{50}$ of 407 FFU, and it was approximately 20 times more virulent than its cDNA cloned virus (Pletnev, A. G. & Men, R. 1998 *PNAS USA* 95:1746-1751). In contrast, the WN/DEN4 chimera and its 3' deletion mutant were significantly less neurovirulent than their wild-type DEN4 or WN parent. Only at a high dose of $10^4$ FFU did a minority of mice, inoculated IC with WN/DEN4 chimera, die. Also, the WN/DEN4 chimera inoculated IC at this dose caused death of suckling mice later than parental WN virus: 4-5 days post-infection for wild-type WN compared to 9-13 days post-infection for the chimera. Additional methods and procedures are taught that allow further attenuation of the IC virulence of the WN/DEN4 chimeric virus by the introduction of mutations that are known to attenuate DEN4 virus for the brain of mice. In addition, we also contemplate achieving further attenuation of WN/DEN4-3'Δ30 by the incorporation of additional attenuating mutations.

Despite the high peripheral virulence of wild-type WN strain NY99 (IP $LD_{50}$ of 10 FFU), chimerization of WN with DEN4 completely ablated this property of its WN parent. Thus, 3-week-old Swiss mice survived IP inoculation of $10^4$ or $10^5$ FFU of chimeric virus. Our observations are consistent with earlier findings that a similar large reduction of peripheral neurovirulence of TBEV or LGT occurs following chimerization with DEN4 (Pletnev, A. G. et al. 1992 *PNAS USA* 89:10532-10536; Pletnev, A. G. & Men, R. 1998 *PNAS. USA* 95:1746-1751; Pletnev, A. G., Bray, M. & Lai, C.-J. 1993 *J Virol* 67:4956-4963). Similar observations were made when the WN/DEN4 chimeras were tested in SCID mice for peripheral virulence (Table 2).

Although highly attenuated, the WN/DEN4 chimeras stimulated a moderate to high level of serum neutralizing antibodies against WN NY99 (Table 3). There was a strong correlation between the level of neutralizing antibodies to WN induced by immunization and resistance to subsequent lethal WN challenge. The immune response of mice inoculated with the chimeras was dose-dependent and indicated that the unmodified WN/DEN4 chimera was slightly more immunogenic than the corresponding 3' deletion mutant. However, 90 to 100% protection against WN challenge was achieved when a single $10^3$ FFU dose of WN/DEN4 chimera or its 3' deletion mutant was used for immunization. A higher dose ($10^4$ FFU) of either chimera provided complete protection to WN challenge. The WN/DEN4 and WN/DEN4-3'Δ30 were also highly attenuated, immunogenic, and protective against WN virus challenge in non-human primates (rhesus monkeys). Thus, the WN prM and E proteins of the chimeric viruses represent effective antigens able to induce complete protection to challenge with highly virulent WN in both mice and monkeys. Our observations concerning safety, immunogenicity, and protective efficacy of the chimeric WN/DEN4 vaccine candidates in mice and monkeys provide a basis for extending our evaluation of the vaccine candidates to humans and to domestic animals, such as horses or birds, which are at high risk. In this way, the use of the WN/DEN4 chimeras as vaccines is envisioned for humans and domestic animals, such as horses or birds.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An attenuated West Nile virus and dengue type 4 virus chimera comprising a first nucleotide sequence encoding a premembrane/membrane (prM) protein and an envelope (E) protein from a West Nile virus and a second nucleotide sequence encoding a capsid (C) protein, the nonstructural proteins from dengue type 4 virus and the 3' untranslated region of the dengue type 4 genome comprising a deletion of about 30 nucleotides between nucleotides 10478-10507 corresponding to the TL2 stem-loop structure.

2. The attenuated West Nile virus and dengue type 4 virus chimera of claim 1, wherein the West Nile virus and dengue type 4 virus chimera comprises a cleavage site joining a dengue virus capsid protein and the West Nile virus prM protein, and wherein the West Nile virus prM protein contains aspartic acid (Asp) at a position 3 amino acids downstream of the cleavage site and contains threonine (Thr) at a position 6 amino acids downstream of the cleavage site.

3. An immunogenic composition comprising an attenuated West Nile virus and dengue type 4 virus chimera of claim 1 and a pharmaceutically acceptable carrier.

4. A vaccine composition comprising an attenuated West Nile virus and dengue type 4 virus chimera of claim 1 and a pharmaceutically acceptable carrier.

5. The vaccine composition of claim 4, wherein the vaccine provides protection against West Nile virus challenge in monkeys.

6. The vaccine of claim 4, wherein the vaccine provides protection against West Nile virus challenge in mice.

* * * * *